(12) United States Patent
Aissaoui et al.

(10) Patent No.: US 7,994,336 B2
(45) Date of Patent: Aug. 9, 2011

(54) AZETIDINE COMPOUNDS AS OREXIN RECEPTOR ANTAGONISTS

(75) Inventors: Hamed Aissaoui, Pulversheim (FR); Christoph Boss, Allschwil (CH); Markus Gude, Allschwil (CH); Ralf Koberstein, Lorrach (DE); Thierry Sifferlen, Wentzwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 83 days.

(21) Appl. No.: 12/377,349

(22) PCT Filed: Aug. 15, 2007

(86) PCT No.: PCT/IB2007/053244
§ 371 (c)(1),
(2), (4) Date: Feb. 12, 2009

(87) PCT Pub. No.: WO2008/020405
PCT Pub. Date: Feb. 21, 2008

(65) Prior Publication Data
US 2010/0222600 A1    Sep. 2, 2010

(30) Foreign Application Priority Data

Aug. 15, 2006  (WO) ................. PCT/IB2006/052814

(51) Int. Cl.
*C07D 513/04* (2006.01)
*C07D 277/00* (2006.01)
*C07D 205/00* (2006.01)
*A61K 31/427* (2006.01)
*A61K 31/431* (2006.01)
*A61K 31/337* (2006.01)

(52) U.S. Cl. ........ 548/155; 548/201; 548/950; 548/953; 514/368; 514/365; 514/210.18

(58) Field of Classification Search ........................ None
See application file for complete search history.

(56) References Cited

U.S. PATENT DOCUMENTS

| 4,267,339 | A | 5/1981 | Tedeschi | |
|---|---|---|---|---|
| 2008/0139575 | A1* | 6/2008 | Lu et al. | ................... 514/254.01 |

FOREIGN PATENT DOCUMENTS

| DE | 2505068 | | 8/1975 |
|---|---|---|---|
| EP | 310096 | A2 | 9/1988 |
| GB | 1493048 | A | 2/1975 |
| WO | WO 94/19344 | | 9/1994 |
| WO | WO 95/29922 | | 11/1995 |
| WO | WO 00/51608 | | 9/2000 |
| WO | WO 01/96302 | | 12/2001 |
| WO | WO01/96302 | | 12/2001 |
| WO | WO 02/46158 | A2 | 6/2002 |
| WO | WO 03/000649 | | 1/2003 |
| WO | WO2004/026866 | | 4/2004 |
| WO | WO 2004/026866 | A1 | 4/2004 |
| WO | WO 2004/081010 | | 9/2004 |

OTHER PUBLICATIONS

International Search Report for WO2008/020405 A3, PCT/IB2007/053244.
Ceccarelli, S. et al., "Rational design, synthesis, and structure-activity relationship of benzoxazolones: New potent mglu5 receptor antagonists based on the fenobam structure", Bioorganic & Medicinal Chemistry Letters, (2007), 17, 5, pp. 1302-1306.
Chemelli, R.M. et al., "Narcolepsy in orexin knockout mice: molecular genetics of sleep regulation", Cell, (1999), 98, pp. 437-451.
Eicher, T. et al., "The Chemistry of Heterocycles: Structure, Reactions, Syntheses, and Applications". $2^{nd}$ Edition, (2003), Wiley, ISBN 978-3-527-30720-6.
Eissenstat, M.A. et al., "Aminoalkylindoles: Structure-Activity Relationships of Novel Cannabinoid Mimetics", J. Med. Chem., (1995), 38, (16), pp. 3094-3105.
Goldstein, S.W. et al., "A Facile Synthesis of Methyl 2-Substituted-4-benzoxazolecarboxylates", Journal of Heterocyclic Chemistry, (1990), 27, pp. 335-336.
Hamamoto, H. et al., "Chemoenzymatic synthesis of the C-13 side chain of paclitaxel (Taxol) and docetaxel (Taxotere)", Tetrahedron Asymmetry, (2000), 11, pp. 4485-4497.
Hrib, N.J. et al., "Benzisoxazole- and Benzisothiazole-3-carboxamides as Potential Atypical Antipsychotic Agents", Journal of Medicinal Chemistry, (1994), 37, (15), pp. 2308-2314.
Ishikawa, T. et al., "Cesium Fluoride-Mediated Claisen Rearrangements of Phenyl Propargyl Ethers: Effect of a Substituent on the Phenyl Ring on the Rearrangement[1]", Heterocycles, (1994), 39, No. 1, pp. 371-380.
Kawakita, T. et al., "Synthesis and Pharmacology of 3,4-Dihydro-3-oxo-1,4-benzoxazine-8-carboxamide Derivatives, a New Class of Potent Serotonin-3 ($5-HT_3$) Receptor Antagonists", Chemical & Pharmaceutical Bulletin, (1992), 40, (3), pp. 624-630.
Kochergin, P.M. et al., "VIII. Synthesis of Some Derivatives of Imidazolecarboxylic and Imidazo-(2,1-b)-Thiazolecarboxylic Acids", Journal of General Chemistry, USSR, (1960), 30. pp. 1542-1547.
Kuroita, T. et al., "Design and Synthesis of 6-Chloro-3,4-dihydro-4-methyl-2H-1,4-benzoxazine-8-carboxamide Derivatives as Potent Serotonin-3 ($5-HT_3$) Receptor Antagonists", Chemical Pharmaceutical Bulletin, (1996), 44, (4), pp. 756-764.

(Continued)

*Primary Examiner* — Kamal Saeed
*Assistant Examiner* — Nyeemah Grazier
(74) *Attorney, Agent, or Firm* — Hoxie & Assoicates LLC; Brittany La

(57) ABSTRACT

The invention relates to novel azetidine compounds of formula (I), wherein $R^1$, $R^2$, and X are as described in the description and their use as orexin receptor antagonists.

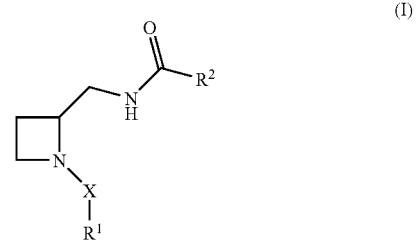

(I)

15 Claims, No Drawings

OTHER PUBLICATIONS

Mazur, I.A. et al., "XLV. Synthesis of Imidazo[2,1-b]thiazole and Some of its Alky, Aryl, and 5,6-Dihydro Derivatives", Chemistry of Heterocyclic Compounds, (1970), 6, pp. 470-473.

Moazzam, M. et al., "Syntheses of Trifluoromethyl Heterocycles", Indian Journal of Chemistry: Section B, (1988), 27B(11), pp. 1051-1053.

Muchmore, S.W. et al., "The Use of Three-Dimensional Shape and Electrostatic Similarity Searching in the Identification of a Melanin-Concentrating Hormone Receptor 1 Antagonist", Chemical Biology & Drug Design, (2006), 67, pp. 174-176.

"Protective Groups in Organic Synthesis", T.W. Greene, P.G.M. Wuts, Wiley-Interscience, (1999).

Remington, The Science and Practice of Pharmacy, $21^{st}$ Edition, (2005), Part 5, "Pharmaceutical Manufacturing" [published by Lippincott Williams & Wilkins].

Sakurai, T. et al., "Orexins and orexin receptors: a family of hypothalamic neuropeptides and G protein-coupled receptors that regulate feeding behavior", Cell, (1998), 92, pp. 573-585.

"Salt selection for basic drugs", Int. J. Pharm. (1986), 33, pp. 201-217.

* cited by examiner

AZETIDINE COMPOUNDS AS OREXIN RECEPTOR ANTAGONISTS

CROSS REFERENCE TO RELATED APPLICATIONS

This application is a 35 U.S.C. §371 National Phase Application of PCT Application No. PCT/IB2007/053244, filed on Aug. 15, 2007, which claims the benefit of PCT/IB2006/052814, filed on Aug. 15, 2006, the contents of each of which are incorporated herein by reference in their entirety.

The present invention relates to novel azetidine compounds of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies such as dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions.

The present invention provides azetidine derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Piperidine derivatives useful as orexin receptor antagonists are disclosed in WO01/96302. An azetidine compound has been described as melanin-concentrating hormone receptor 1 antagonist in Muchmore S. W. et al Chemical Biology & Drug Design 2006, 67, 2, 174-176. The present invention describes for the first time azetidine compounds as orexin antagonists.

i) A first aspect of the invention consists of azetidine derivatives of the formula (I)

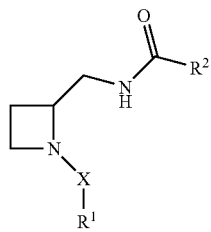

Formula (I)

wherein
X represents C(O) or $SO_2$;
$R^1$ represents aryl, wherein the aryl is unsubstituted, or mono-, di-, or tri-substituted, wherein the substituents are independently selected from the group consisting of $(C_{1-4})$alkyl, $(C_{1-4})$alkoxy, trifluoromethyl, trifluoromethoxy, $NR^3R^4$, $N(R^3)C(O)R^4$, $C(O)NR^3R^4$ and unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy;
or $R^1$ represents heteroaryl (especially five-membered heteroaryl), wherein the heteroaryl is unsubstituted, or mono-, di-, or tri-substituted (especially mono-, or di-substituted), wherein the substituents are independently selected from the group consisting of $(C_{1-4})$alkyl, $(C_{1-4})$alkoxy, trifluoromethoxy, $NR^3R^4$, $N(R^3)C(O)R^4$, $C(O)NR^3R^4$, and unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy;
$R^2$ represents aryl, wherein the aryl is unsubstituted, or mono-, di-, or tri-substituted wherein the substituents are independently selected from the group consisting of $(C_{1-4})$alkyl, $(C_{1-4})$alkoxy, halogen, cyano, trifluoromethyl, trifluoromethoxy, $NR^3R^4$, $N(R^3)C(O)R^4$, and $C(O)NR^3R^4$;
heteroaryl, wherein the heteroaryl is unsubstituted, or mono-, di-, or tri-substituted wherein the substituents are independently selected from the group consisting of $(C_{1-4})$alkyl, $(C_{1-4})$alkoxy, halogen, cyano, trifluoromethyl, trifluoromethoxy, $NR^3R^4$, $N(R^3)C(O)R^4$, and $C(O)NR^3R^4$;
or $R^2$ represents heterocyclyl, wherein heterocyclyl means a phenyl ring fused to a 5- or 6-membered saturated or unsaturated non-aromatic ring containing 1 or 2 heteroatoms independently selected from oxygen and nitrogen, wherein said heterocyclyl is unsubstituted, or mono-substituted with $(C_{1-4})$alkyl or oxo;
$R^3$ represents hydrogen or $(C_{1-4})$alkyl; and
$R^4$ represents hydrogen or $(C_{1-4})$alkyl.

The compounds of formula (I) may contain one or more stereogenic or asymmetric centers, such as one or more asymmetric carbon atoms. Substituents at a double bond may be present in the Z- or E-configuration unless indicated otherwise. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference to a compound of formula (I) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The following paragraphs provide definitions of the various chemical moieties for the compounds according to the invention and are intended to apply uniformly throughout the specification and claims, unless an otherwise expressly set out definition provides a broader or narrower definition.

The term "halogen" means fluorine, chlorine, or bromine, preferably fluorine or chlorine.

The term "$(C_{1-4})$alkyl", alone or in combination, means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl or tert.-butyl. Preferred are methyl and ethyl. Most preferred is methyl.

The term "$(C_{1-4})$alkoxy", alone or in combination, means a group of the formula $(C_{1-4})$alkyl-O— in which the term "$(C_{1-4})$alkyl" has the previously given significance, such as methoxy, ethoxy, n-propoxy, isopropoxy, n-butoxy, isobutoxy, sec.-butoxy or tert.-butoxy. Preferred are methoxy and ethoxy. Most preferred is methoxy.

The term "aryl", alone or in combination, means a phenyl or a naphthyl group. Preferred is a phenyl group. The aryl group is unsubstituted, or mono-, di-, or tri-substituted wherein the substituents are independently selected from the group consisting of $(C_{1-4})$alkyl, $(C_{1-4})$alkoxy, halogen, cyano, trifluoromethyl, trifluoromethoxy, $NR^3R^4$, $N(R^3)C(O)R^4$, $C(O)NR^3R^4$, and unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy.

In case $R^1$ represents "aryl" the term preferably means the above-mentioned groups which are unsubstituted, or mono-, di-, or tri-substituted, wherein the substituents are independently selected from the group consisting of $(C_{1-4})$alkyl, $(C_{1-4})$alkoxy, trifluoromethyl, trifluoromethoxy, $NR^3R^4$, $N(R^3)C(O)R^4$, $C(O)NR^3R^4$ and unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy. Especially, the substituents are independently selected from the group consisting of $(C_{1-4})$alkyl, $(C_{1-4})$alkoxy, trifluoromethoxy, $NR^3R^4$, $N(R^3)C(O)R^4$, $C(O)NR^3R^4$ and unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy.

Examples of aryl groups as used for the substituent $R^1$ are biphenyl (especially biphen-2-yl), 2-trifluoromethoxyphenyl, 2-methoxyphenyl, 3-trifluoromethyl-phenyl, naphthalene-1-yl, 2'-fluoro-biphen-2-yl, 3'-fluoro-biphen-2-yl, 4'-fluoro-biphen-2-yl, 2'-methyl-biphen-2-yl, 3'-methyl-biphen-2-yl, 4'-methyl-biphen-2-yl, 3',4'-dimethyl-biphen-2-yl, and 3'-trifluoromethyl-biphen-2-yl. Preferred examples are biphen-2-yl, 2'-fluoro-biphen-2-yl, 3'-fluoro-biphen-2-yl, 4'-fluoro-biphen-2-yl, 2'-methyl-biphen-2-yl, 3'-methyl-biphen-2-yl, 4'-methyl-biphen-2-yl, 3',4'-dimethyl-biphen-2-yl, and 3'-trifluoromethyl-biphen-2-yl. Most preferred examples are biphen-2-yl, and 3',4'-dimethyl-biphen-2-yl.

In case $R^2$ represents "aryl" the term preferably means the above-mentioned groups which are unsubstituted, or mono-, di-, or tri-substituted wherein the substituents are independently selected from the group consisting of $(C_{1-4})$alkyl, $(C_{1-4})$alkoxy, halogen, cyano, trifluoromethyl, trifluoromethoxy, $NR^3R^4$, $N(R^3)C(O)R^4$, and $C(O)NR^3R^4$ (preferably substituents are selected from $(C_{1-4})$alkyl, $(C_{1-4})$alkoxy, and halogen). Examples of aryl groups as used for the substituent $R^2$ are 3-chloro-2-methyl-phenyl, 2-methoxy-phenyl, or 2-bromo-5-methyl-phenyl.

The term "heteroaryl", alone or in combination, means a 5- to 10-membered monocyclic or bicyclic aromatic ring containing 1, 2 or 3 heteroatoms independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, and imidazo[2,1-b]thiazole. The above-mentioned heteroaryl groups are unsubstituted, or mono-, di-, or tri-substituted wherein the substituents are independently selected from the group consisting of $(C_{1-4})$alkyl, $(C_{1-4})$alkoxy, halogen, cyano, trifluoromethyl, trifluoromethoxy, $NR^3R^4$, $N(R^3)C(O)R^4$, $C(O)NR^3R^4$, and unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy.

In case $R^1$ represents "heteroaryl" the term preferably means a five-membered monocyclic aromatic ring containing 1, 2 or 3 heteroatoms independently selected from oxygen, nitrogen and sulfur. Examples of such heteroaryl groups as used for the substituent $R^1$ are oxazolyl, and thiazolyl. The above-mentioned heteroaryl groups as used for the substituent $R^1$ are unsubstituted, or mono-, di-, or tri-substituted (preferred mono- or disubstituted; more preferred disubstituted) wherein the substituents are independently selected from the group consisting of $(C_{1-4})$alkyl, $(C_{1-4})$alkoxy, trifluoromethoxy, $NR^3R^4$, $N(R^3)C(O)R^4$, $C(O)NR^3R^4$, and unsubstituted, or mono-, di-, or tri-substituted phenyl (preferred mono- or disubstituted phenyl) wherein the substituents are independently selected from the group consisting of $(C_{1-4})$alkyl, $(C_{1-4})$alkoxy, halogen, cyano, trifluoromethyl and trifluoromethoxy.

In case $R^2$ represents "heteroaryl" the term means the above-mentioned groups, preferably it means a 8- to 10-membered bicyclic aromatic ring containing 1, 2 or 3 heteroatoms, each independently selected from oxygen, nitrogen and sulfur. Examples of such heteroaryl groups as used for the substituent $R^2$ are indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, cinnolinyl, or imidazo[2,1-b]thiazolyl (especially imidazo[2,1-b]thiazolyl). Particular examples of such heteroaryl groups as used for the substituent $R^2$ are indol-3-yl, indol-4-yl, indol-7-yl, indazol-3-yl, indazol-4-yl, indazol-7-yl, benzofuran-4-yl, benzofuran-7-yl, benzisoxazol-3-yl, benzisoxazol-4-yl, benzisoxazol-7-yl, benzoxazol-4-yl, benzoxazol-7-yl, benzoxadiazol-4-yl, benzoxadiazol-7-yl, benzothiophene-3-yl, benzothiophene-4-yl, benzothiophene-7-yl, benzthiazol-4-yl, benzthiazol-7-yl, benzoisothiazol-3-yl, benzoisothiazol-4-yl, benzoisothiazol-7-yl, benzothiadiazol-4-yl, benzothiadiazol-7-yl, benzimidazol-4-yl, benzimidazol-7-yl, imidazo[2,1-b]thiazol-2-yl, imidazo[2,1-b]thiazol-3-yl, imidazo[2,1-b]thiazol-5-yl, and imidazo[2,1-b]thiazol-6-yl. The above-mentioned heteroaryl groups as used for the substituent $R^2$ are unsubstituted, or mono-, di-, or tri-substituted (preferred unsubstituted, or mono-substituted) wherein the substituents are independently selected from the group consisting of ($C_{1-4}$)alkyl, ($C_{1-4}$)alkoxy, halogen, cyano, trifluoromethyl, trifluoromethoxy, $NR^3R^4$, $N(R^3)C(O)R^4$, and $C(O)NR^3R^4$ (preferred from ($C_{1-4}$)alkyl, and halogen, more preferred from ($C_{1-4}$)alkyl).

The term "heterocyclyl", alone or in combination, means a phenyl ring fused to a 5- or 6-membered saturated or unsaturated non-aromatic ring containing 1 or 2 heteroatoms independently selected from oxygen and nitrogen. Examples of heterocyclyl groups as used for the substituent $R^2$ are 3,4-dihydro-2H-benzo[1,4]oxazinyl, 2,3-dihydro-benzofuranyl, benzo[1,3]dioxolyl, 2,3-dihydro-benzo[1,4]dioxinyl, 4H-benzo[1,3]dioxinyl, chromanyl, and chromenyl (especially 3,4-dihydro-2H-benzo[1,4]oxazinyl). The above-mentioned heterocyclyl groups are unsubstituted, or mono-substituted with ($C_{1-4}$)alkyl or oxo. 2,3-Dihydro-benzofuranyl, benzo[1,3]dioxolyl, 2,3-dihydro-benzo[1,4]dioxinyl, 4H-benzo[1,3]dioxinyl, chromanyl, and chromenyl groups are preferably unsubstituted.

The term "$NR^3R^4$" means for example $NH_2$, or $N(CH_3)_2$ (especially $NH_2$).

The term "$N(R^3)C(O)R^4$" means for example $N(CH_3)C(O)CH_3$.

The term "$C(O)NR^3R^4$" means for example $C(O)N(CH_3)_2$.

ii) A further embodiment of the invention relates to azetidine derivatives according to embodiment i), wherein the azetidine moiety has the (S)-configuration:

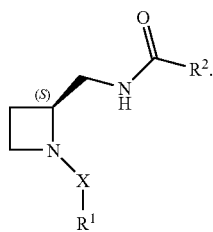

iii) A further embodiment of the invention relates to azetidine derivatives according to embodiments i) and ii), wherein X represents C(O).

iv) A further embodiment of the invention relates to azetidine derivatives according to any one of embodiments i) to iii), wherein
$R^1$ represents aryl, wherein the aryl is unsubstituted, or mono-, di-, or tri-substituted, wherein the substituents are independently selected from the group consisting of ($C_{1-4}$)alkyl, ($C_{1-4}$)alkoxy, trifluoromethyl, trifluoromethoxy, $NR^3R^4$, $N(R^3)C(O)R^4$, $C(O)NR^3R^4$ and unsubstituted, or mono-, di-, or tri-substituted phenyl wherein the substituents are independently selected from the group consisting of ($C_{1-4}$)alkyl, ($C_{1-4}$)alkoxy, halogen, cyano, trifluoromethyl and trifluoromethoxy.

v) A further embodiment of the invention relates to azetidine derivatives according to any one of embodiments i) to iii), wherein
$R^1$ represents heteroaryl (especially five-membered heteroaryl), wherein the heteroaryl is unsubstituted, or mono-, di-, or tri-substituted (especially mono-, or di-substituted), wherein the substituents are independently selected from the group consisting of ($C_{1-4}$)alkyl, ($C_{1-4}$)alkoxy, trifluoromethoxy, $NR^3R^4$, $N(R^3)C(O)R^4$, $C(O)NR^3R^4$, and unsubstituted, or mono-, di-, or tri-substituted phenyl wherein the substituents are independently selected from the group consisting of ($C_{1-4}$)alkyl, ($C_{1-4}$)alkoxy, halogen, cyano, trifluoromethyl and trifluoromethoxy.

vi) A further embodiment of the invention relates to azetidine derivatives according to any one of embodiments i) to iii), wherein
$R^1$ represents mono-substituted aryl, wherein the substituent is selected from the group consisting of ($C_{1-4}$)alkoxy, trifluoromethyl, trifluoromethoxy, and unsubstituted, or mono-, or di-substituted phenyl wherein the substituents are independently selected from the group consisting of ($C_{1-4}$)alkyl, halogen and trifluoromethyl (preferred ($C_{1-4}$) alkyl); or
$R^1$ represents di-substituted five-membered heteroaryl, wherein the substituents are independently selected from the group consisting of ($C_{1-4}$)alkyl, —$NH_2$, and unsubstituted, or mono-, di-, or tri-substituted (preferred mono- or disubstituted) phenyl wherein the substituents are independently selected from the group consisting of ($C_{1-4}$)alkyl, ($C_{1-4}$)alkoxy, halogen, cyano, trifluoromethyl and trifluoromethoxy (preferably from ($C_{1-4}$)alkyl, ($C_{1-4}$)alkoxy, halogen, and trifluoromethyl).

vii) A further embodiment of the invention relates to azetidine derivatives according to any one of embodiments i) to vi), wherein
$R^2$ represents heteroaryl, wherein the heteroaryl is unsubstituted, or mono-, di-, or tri-substituted wherein the substituents are independently selected from the group consisting of ($C_{1-4}$) alkyl, ($C_{1-4}$)alkoxy, halogen, cyano, trifluoromethyl, trifluoromethoxy, $NR^3R^4$, $N(R^3)C(O)R^4$, and $C(O)NR^3R^4$; or
$R^2$ represents heterocyclyl, wherein heterocyclyl means a phenyl ring fused to a 5- or 6-membered saturated or unsaturated non-aromatic ring containing 1 or 2 heteroatoms independently selected from oxygen and nitrogen, wherein said heterocyclyl is unsubstituted, or mono-substituted with ($C_{1-4}$)alkyl or oxo.

viii) A further embodiment of the invention relates to azetidine derivatives according to any one of embodiments i) to vi), wherein
$R^2$ represents heteroaryl, wherein the heteroaryl is unsubstituted, or mono-, di-, or tri-substituted wherein the substituents are independently selected from the group consisting of ($C_{1-4}$) alkyl, ($C_{1-4}$)alkoxy, halogen, cyano, trifluoromethyl, trifluoromethoxy, $NR^3R^4$, $N(R^3)C(O)R^4$, and $C(O)NR^3R^4$.

ix) A further embodiment of the invention relates to azetidine derivatives according to any one of embodiments i) to vi), wherein
$R^2$ represents heterocyclyl, wherein heterocyclyl means a phenyl ring fused to a 5- or 6-membered saturated or unsaturated non-aromatic ring containing 1 or 2 heteroatoms independently selected from oxygen and nitrogen, wherein said heterocyclyl is unsubstituted, or mono-substituted with ($C_{1-4}$)alkyl or oxo.

x) A further embodiment of the invention relates to azetidine derivatives according to any one of embodiments i) to vi), wherein
$R^2$ represents heteroaryl, wherein the heteroaryl is unsubstituted, or mono-, or di-substituted wherein the substituents are independently selected from the group consisting of ($C_{1-4}$)alkyl, and halogen; or
$R^2$ represents heterocyclyl, wherein heterocyclyl means a phenyl ring fused to a 5- or 6-membered saturated or unsaturated non-aromatic ring containing 1 or 2 heteroatoms independently selected from oxygen and nitrogen, wherein said heterocyclyl is unsubstituted, or mono-substituted with ($C_{1-4}$)alkyl or oxo.

xi) A further embodiment of the invention relates to azetidine derivatives according to any one of embodiments i) to iii), wherein R$^1$ represents aryl or heteroaryl, wherein the aryl or heteroaryl is unsubstituted or independently mono-, di-, or trisubstituted, wherein the substituents are independently selected from the group consisting of (C$_{1-4}$)alkyl, (C$_{1-4}$)alkoxy, trifluoromethoxy, NR$^3$R$^4$, N(R$^3$)C(O)R$^4$, C(O)NR$^3$R$^4$ and unsubstituted or independently mono-, di-, or trisubstituted phenyl wherein the substituents are independently selected from the group consisting of (C$_{1-4}$)alkyl, (C$_{1-4}$)alkoxy, halogen, cyano, trifluoromethyl and trifluoromethoxy; and R$^2$ represents aryl or heteroaryl, wherein the aryl or heteroaryl is unsubstituted or independently mono-, di-, or trisubstituted wherein the substituents are independently selected from the group consisting of (C$_{1-4}$)alkyl, (C$_{1-4}$)alkoxy, halogen, cyano, trifluoromethyl, trifluoromethoxy, NR$^3$R$^4$, N(R$^3$)C(O)R$^4$, and C(O)NR$^3$R$^4$.

xii) A further embodiment of the invention relates to azetidine derivatives according to any one of embodiments i) to iv) and vii) to xi), wherein, in case R$^1$ represents aryl, said aryl is mono-substituted phenyl, wherein the substituent is selected from the group consisting of (C$_{1-4}$)alkoxy, trifluoromethoxy, and unsubstituted, or mono-, di-, or tri-substituted phenyl wherein the substituents are independently selected from the group consisting of (C$_{1-4}$)alkyl, (C$_{1-4}$)alkoxy, halogen, cyano, trifluoromethyl and trifluoromethoxy (especially the substituent is unsubstituted phenyl, or mono-, or di-substituted phenyl wherein the substituents are independently selected from (C$_{1-4}$)alkyl, halogen and trifluoromethyl).

xiii) A further embodiment of the invention relates to azetidine derivatives according to any one of embodiments i) to iv) and vii) to xi), wherein, in case R$^1$ represents aryl, said aryl is mono-substituted phenyl, wherein the substituent is unsubstituted, or mono-, di-, or tri-substituted phenyl wherein the substituents are independently selected from the group consisting of (C$_{1-4}$)alkyl, (C$_{1-4}$)alkoxy, halogen, cyano, trifluoromethyl and trifluoromethoxy (especially the substituent is unsubstituted phenyl, or mono-, or di-substituted phenyl wherein the substituents are independently selected from methyl).

xiv) A further embodiment of the invention relates to azetidine derivatives according to any one of embodiments i) to iv) and vi) to xi), wherein, in case R$^1$ represents aryl, said aryl is phenyl which is mono-substituted in position 2, wherein the substituent is unsubstituted, or mono-, or di-substituted phenyl wherein the substituents are independently selected from the group consisting of (C$_{1-4}$)alkyl, halogen, and trifluoromethyl (especially the substituent is unsubstituted phenyl, or mono-, or di-substituted phenyl wherein the substituents are independently selected from methyl).

xv) A further embodiment of the invention relates to azetidine derivatives according to any one of embodiments i) to iv) and vi) to xi), wherein, in case R$^1$ represents aryl, said aryl is a group selected from biphen-2-yl, 2-trifluoromethoxyphenyl, 2-methoxyphenyl, 3-trifluoromethyl-phenyl, naphthalene-1-yl, 2'-fluoro-biphen-2-yl, 3'-fluoro-biphen-2-yl, 4'-fluoro-biphen-2-yl, 2'-methyl-biphen-2-yl, 3'-methyl-biphen-2-yl, 4'-methyl-biphen-2-yl, 3',4'-dimethyl-biphen-2-yl, and 3'-trifluoromethyl-biphen-2-yl.

xvi) A further embodiment of the invention relates to azetidine derivatives according to any one of embodiments i) to iii), v) and vii) to xv), wherein, in case R$^1$ represents heteroaryl, said heteroaryl is unsubstituted, mono-, di-, or tri-substituted (preferred mono- or disubstituted; more preferred disubstituted), wherein the substituents are independently selected from the group consisting of (C$_{1-4}$)alkyl, NR$^3$R$^4$, and unsubstituted, or mono-, di-, or tri-substituted (preferred mono- or disubstituted) phenyl wherein the substituents are independently selected from the group consisting of (C$_{1-4}$)alkyl, (C$_{1-4}$)alkoxy, halogen, cyano, trifluoromethyl and trifluoromethoxy (preferred (C$_{1-4}$)alkyl, (C$_{1-4}$)alkoxy, halogen and trifluoromethyl).

xvii) A further embodiment of the invention relates to azetidine derivatives according to any one of embodiments i) to iii) and v) to xv), wherein, in case R$^1$ represents heteroaryl, said heteroaryl is thiazolyl which is disubstituted, wherein the substituents are independently selected from (C$_{1-4}$) alkyl, and unsubstituted, or mono-, di-, or tri-substituted (preferred mono- or disubstituted) phenyl wherein the substituents are independently selected from the group consisting of (C$_{1-4}$)alkyl, (C$_{1-4}$)alkoxy, halogen, cyano, trifluoromethyl and trifluoromethoxy.

xviii) A further embodiment of the invention relates to azetidine derivatives according to any one of embodiments i) to iii) and v) to xv), wherein, in case R$^1$ represents heteroaryl, said heteroaryl is thiazolyl which is disubstituted, wherein the substituents are independently selected from the group consisting of methyl and unsubstituted, or mono-, di-, or tri-substituted (preferred mono- or disubstituted) phenyl wherein the substituents are independently selected from the group consisting of methyl, ethyl, fluorine and trifluoromethyl.

xix) A further embodiment of the invention relates to azetidine derivatives according to any one of embodiments i) to iii) and v) to xv), wherein, in case R$^1$ represents heteroaryl, said heteroaryl is thiazol-4-yl, which is di-substituted in positions 2 and 5, wherein the substituent in position 2 is selected from (C$_{1-4}$)alkyl and —NH$_2$ and the substituent in position 5 is unsubstituted, or mono-, or di-substituted phenyl, wherein the substituents are independently selected from the group consisting of (C$_{1-4}$)alkyl, (C$_{1-4}$) alkoxy, halogen, cyano, trifluoromethyl and trifluoromethoxy (preferred (C$_{1-4}$)alkyl, halogen and trifluoromethyl).

xx) A further embodiment of the invention relates to azetidine derivatives according to any one of embodiments i) to iii) and v) to xv), wherein, in case R$^1$ represents heteroaryl, said heteroaryl is a group selected from:

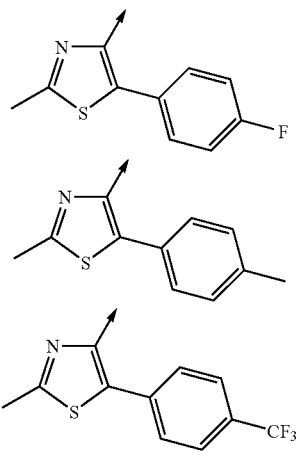

xxi) A further embodiment of the invention relates to azetidine derivatives according to any one of embodiments i) to iii) and v) to xv), wherein, in case R¹ represents heteroaryl, said heteroaryl is a group selected from:

-continued

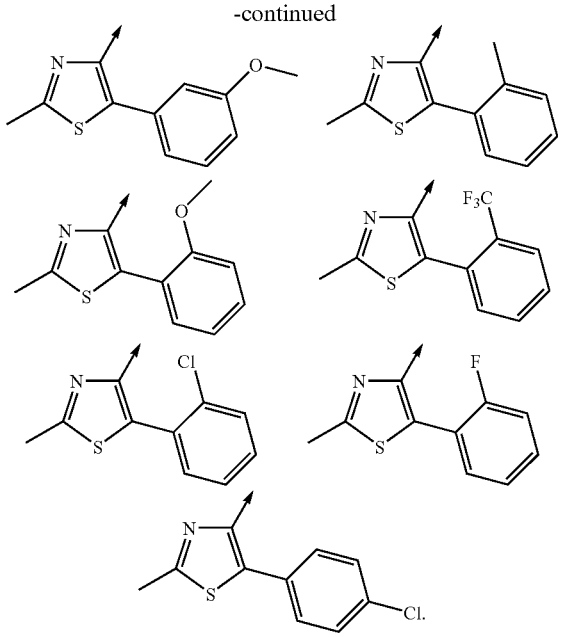

xxxii) A further embodiment of the invention relates to azetidine derivatives according to any one of embodiments i) to viii) and x) to xxi), wherein, in case $R^2$ represents heteroaryl, said heteroaryl is unsubstituted, or mono-, or di-substituted, wherein the substituents are independently selected from halogen (especially chloro) and $(C_{1-4})$alkyl (especially the substituents are selected from $(C_{1-4})$alkyl).

xxiii) A further embodiment of the invention relates to azetidine derivatives according to any one of embodiments i) to viii) and x) to xxi), wherein, in case $R^2$ represents heteroaryl, said heteroaryl is unsubstituted, or mono-substituted with methyl.

xxiv) A further embodiment of the invention relates to azetidine derivatives according to any one of embodiments i) to viii) and x) to xxi), wherein, in case $R^2$ represents heteroaryl, said heteroaryl is a group selected from benzofuran-4-yl, 2-methyl-benzofuran-4-yl, 2-methyl-benzofuran-3-yl, benzoxazol-4-yl, imidazo[2,1-b]-thiazole-5-yl, 6-methyl-imidazo[2,1-b]-thiazole-5-yl, 6-chloro-imidazo[2,1-b]-thiazole-5-yl, 3-methyl-imidazo[2,1-b]-thiazole-2-yl, 3,5-dimethyl-imidazo[2,1-b]-thiazole-6-yl, and 3-methyl-imidazo[2,1-b]thiazol-5-yl.

xxv) A further embodiment of the invention relates to azetidine derivatives according to any one of embodiments i) to viii) and x) to xxi), wherein, in case $R^2$ represents heteroaryl, said heteroaryl is a group selected from benzofuran-4-yl, imidazo[2,1-b]-thiazole-5-yl, 6-chloro-imidazo[2,1-b]-thiazole-5-yl, and 6-methyl-imidazo[2,1-b]-thiazole-5-yl (preferred benzofuran-4-yl, and 6-methyl-imidazo[2,1-b]-thiazole-5-yl; more preferred 6-methyl-imidazo[2,1-b]-thiazole-5-yl).

xxvi) A further embodiment of the invention relates to azetidine derivatives according to any one of embodiments i) to vii), ix), x) and xii) to xxv), wherein, in case $R^2$ represents heterocyclyl, said heterocyclyl is a group selected from 3,4-dihydro-2H-benzo[1,4]oxazine-5-yl, 3,4-dihydro-2H-benzo[1,4]oxazine-8-yl, 4-methyl-3,4-dihydro-2H-benzo[1,4]oxazine-5-yl, 4-methyl-3,4-dihydro-2H-benzo[1,4]oxazine-8-yl, 3-oxo-3,4-dihydro-2H-benzo[1,4]oxazine-5-yl, 4-methyl-3-oxo-3,4-dihydro-2H-benzo[1,4]oxazine-5-yl, 4-methyl-3-oxo-3,4-dihydro-2H-benzo[1,4]oxazine-8-yl, 2,3-dihydro-benzofuran-7-yl, chroman-8-yl, chroman-5-yl, and 2H-chromene-5-yl.

xxvii) A further embodiment of the invention relates to azetidine derivatives according to any one of embodiments i) to vii), ix), x) and xii) to xxv), wherein, in case $R^2$ represents heterocyclyl, said heterocyclyl is a group selected from 3,4-dihydro-2H-benzo[1,4]oxazine-5-yl, 4-methyl-3,4-dihydro-2H-benzo[1,4]oxazine-8-yl, 3-oxo-3,4-dihydro-2H-benzo[1,4]oxazine-5-yl, 4-methyl-3-oxo-3,4-dihydro-2H-benzo[1,4]oxazine-8-yl, chroman-8-yl, chroman-5-yl, and 2H-chromene-5-yl (especially 3,4-dihydro-2H-benzo[1,4]oxazine-5-yl, 4-methyl-3,4-dihydro-2H-benzo[1,4]oxazine-8-yl, 3-oxo-3,4-dihydro-2H-benzo[1,4]oxazine-5-yl, and 4-methyl-3-oxo-3,4-dihydro-2H-benzo[1,4]oxazine-8-yl).

xxviii) Examples of azetidine derivatives of formula (I) according to embodiment i) are selected from the group consisting of:

Benzofuran-4-carboxylic acid [1-(biphenyl-2-carbonyl)-azetidin-2-ylmethyl]-amide;

(2S)-Benzofuran-4-carboxylic acid [1-(biphenyl-2-carbonyl)-azetidin-2-ylmethyl]-amide;

Benzofuran-4-carboxylic acid [1-(biphenyl-2-sulfonyl)-azetidin-2-ylmethyl]-amide;

(2S)-Benzofuran-4-carboxylic acid [1-(biphenyl-2-sulfonyl)-azetidin-2-ylmethyl]-amide;

(2S)-Benzofuran-4-carboxylic acid [1-(2-trifluoromethoxy-benzenesulfonyl)-azetidin-2-ylmethyl]-amide;

(2S)-Benzofuran-4-carboxylic acid [1-(2-methoxy-benzenesulfonyl)-azetidin-2-ylmethyl]-amide;

Benzofuran-4-carboxylic acid {1-(4-fluoro-phenyl)-2-methyl-thiazole-4-carbonyl]-azetidin-2-ylmethyl}-amide;

6-Methyl-imidazo[2,1-b]thiazole-5-carboxylic acid [1-(2-methyl-5-p-tolyl-thiazole-4-carbonyl)-azetidin-2-ylmethyl]-amide;

6-Methyl-imidazo[2,1-b]thiazole-5-carboxylic acid{1-[5-(4-fluoro-phenyl)-2-methyl-thiazole-4-carbonyl]-azetidin-2-ylmethyl}-amide;

6-Methyl-imidazo[2,1-b]thiazole-5-carboxylic acid [1-(2-methyl-5-m-tolyl-thiazole-4-carbonyl)-azetidin-2-ylmethyl]-amide;

6-Methyl-imidazo[2,1-b]thiazole-5-carboxylic acid{1-[5-(3-fluoro-phenyl)-2-methyl-thiazole-4-carbonyl]-azetidin-2-ylmethyl}-amide;

6-Methyl-imidazo[2,1-b]thiazole-5-carboxylic acid{1-[5-(4-trifluoromethyl-phenyl)-2-methyl-thiazole-4-carbonyl]-azetidin-2-ylmethyl}-amide;

6-Methyl-imidazo[2,1-b]thiazole-5-carboxylic acid{1-[5-(4-ethyl-phenyl)-2-methyl-thiazole-4-carbonyl]-azetidin-2-ylmethyl}-amide;

(2S)-Benzofuran-4-carboxylic acid [1-(3-trifluoromethyl-benzoyl)-azetidin-2-ylmethyl]-amide;

(2S)-Benzofuran-4-carboxylic acid [1-(3',4'-dimethyl-biphenyl-2-carbonyl)-azetidin-2-ylmethyl]-amide;

(2S)-Benzofuran-4-carboxylic acid{1-[5-(4-fluoro-phenyl)-2-methyl-thiazole-4-carbonyl]-azetidin-2-ylmethyl}-amide;

(2S)-6-Methyl-imidazo[2,1-b]thiazole-5-carboxylic acid{1-[5-(3,4-dimethyl-phenyl)-2-methyl-thiazole-4-carbonyl]-azetidin-2-ylmethyl}-amide;

(2S)-6-Methyl-imidazo[2,1-b]thiazole-5-carboxylic acid [1-(2-methyl-5-m-tolyl-thiazole-4-carbonyl)-azetidin-2-ylmethyl]-amide;

(2S)-6-Methyl-imidazo[2,1-b]thiazole-5-carboxylic acid [1-(3',4'-dimethyl-biphenyl-2-carbonyl)-azetidin-2-ylmethyl]-amide;

(2S)-6-Methyl-imidazo[2,1-b]thiazole-5-carboxylic acid [1-(2-amino-5-m-tolyl-thiazole-4-carbonyl)-azetidin-2-ylmethyl]-amide;

(2S)-6-Chloro-imidazo[2,1-b]thiazole-5-carboxylic acid [1-(2-methyl-5-m-tolyl-thiazole-4-carbonyl)-azetidin-2-ylmethyl]-amide;

(2S)-6-Chloro-imidazo[2,1-b]thiazole-5-carboxylic acid [1-(2-amino-5-m-tolyl-thiazole-4-carbonyl)-azetidin-2-ylmethyl]-amide;

Benzofuran-4-carboxylic acid [1-(3',4'-dimethyl-biphenyl-2-carbonyl)-azetidin-2-ylmethyl]-amide;

6-Methyl-imidazo[2,1-b]thiazole-5-carboxylic acid {1-[5-(3,4-dimethyl-phenyl)-2-methyl-thiazole-4-carbonyl]-azetidin-2-ylmethyl}-amide;

6-Methyl-imidazo[2,1-b]thiazole-5-carboxylic acid {1-[5-(3-methoxy-phenyl)-2-methyl-thiazole-4-carbonyl]-azetidin-2-ylmethyl}-amide;

6-Methyl-imidazo[2,1-b]thiazole-5-carboxylic acid {1-[5-(3-chloro-phenyl)-2-methyl-thiazole-4-carbonyl]-azetidin-2-ylmethyl}-amide;

6-Methyl-imidazo[2,1-b]thiazole-5-carboxylic acid {1-[2-methyl-5-(3-trifluoromethyl-phenyl)-thiazole-4-carbonyl]-azetidin-2-ylmethyl}-amide;

6-Methyl-imidazo[2,1-b]thiazole-5-carboxylic acid {1-[5-(4-methoxy-phenyl)-2-methyl-thiazole-4-carbonyl]-azetidin-2-ylmethyl}-amide;

6-Methyl-imidazo[2,1-b]thiazole-5-carboxylic acid {1-[5-(3,5-difluoro-phenyl)-2-methyl-thiazole-4-carbonyl]-azetidin-2-ylmethyl}-amide;

6-Methyl-imidazo[2,1-b]thiazole-5-carboxylic acid {1-[5-(3-bromo-4-fluoro-phenyl)-2-methyl-thiazole-4-carbonyl]-azetidin-2-ylmethyl}-amide;

6-Methyl-imidazo[2,1-b]thiazole-5-carboxylic acid {1-[5-(4-chloro-phenyl)-2-methyl-thiazole-4-carbonyl]-azetidin-2-ylmethyl}-amide;

6-Methyl-imidazo[2,1-b]thiazole-5-carboxylic acid {1-[5-(3,4-dichloro-phenyl)-2-methyl-thiazole-4-carbonyl]-azetidin-2-ylmethyl}-amide;

6-Chloro-imidazo[2,1-b]thiazole-5-carboxylic acid {1-[5-(3,4-dimethyl-phenyl)-2-methyl-thiazole-4-carbonyl]-azetidin-2-ylmethyl}-amide;

6-Chloro-imidazo[2,1-b]thiazole-5-carboxylic acid [1-(2-methyl-5-m-tolyl-thiazole-4-carbonyl)-azetidin-2-ylmethyl]-amide;

2-Methyl-benzofuran-4-carboxylic acid [1-(2-methyl-5-m-tolyl-thiazole-4-carbonyl)-azetidin-2-ylmethyl]-amide;

2H-Chromene-5-carboxylic acid [1-(2-methyl-5-m-tolyl-thiazole-4-carbonyl)-azetidin-2-ylmethyl]-amide;

Benzooxazole-4-carboxylic acid [1-(2-methyl-5-m-tolyl-thiazole-4-carbonyl)-azetidin-2-ylmethyl]-amide;

Benzofuran-3-carboxylic acid [1-(2-methyl-5-m-tolyl-thiazole-4-carbonyl)-azetidin-2-ylmethyl]-amide;

2-Methyl-benzofuran-3-carboxylic acid [1-(2-methyl-5-m-tolyl-thiazole-4-carbonyl)-azetidin-2-ylmethyl]-amide;

3,5-Dimethyl-imidazo[2,1-b]thiazole-6-carboxylic acid [1-(2-methyl-5-m-tolyl-thiazole-4-carbonyl)-azetidin-2-ylmethyl]-amide;

3,4-Dihydro-2H-benzo[1,4]oxazine-5-carboxylic acid [1-(2-methyl-5-m-tolyl-thiazole-4-carbonyl)-azetidin-2-ylmethyl]-amide;

5-Methyl-imidazo[2,1-b]thiazole-6-carboxylic acid [1-(2-methyl-5-m-tolyl-thiazole-4-carbonyl)-azetidin-2-ylmethyl]-amide;

4-Methyl-3-oxo-3,4-dihydro-2H-benzo[1,4]oxazine-8-carboxylic acid [1-(2-methyl-5-m-tolyl-thiazole-4-carbonyl)-azetidin-2-ylmethyl]-amide;

Imidazo[2,1-b]thiazole-5-carboxylic acid [1-(2-methyl-5-m-tolyl-thiazole-4-carbonyl)-azetidin-2-ylmethyl]-amide;

Imidazo[2,1-b]thiazole-5-carboxylic acid [1-(3',4'-dimethyl-biphenyl-2-carbonyl)-azetidin-2-ylmethyl]-amide;

3-Methyl-imidazo[2,1-b]thiazole-5-carboxylic acid [1-(3',4'-dimethyl-biphenyl-2-carbonyl)-azetidin-2-ylmethyl]-amide;

3,5-Dimethyl-imidazo[2,1-b]thiazole-6-carboxylic acid [1-(3',4'-dimethyl-biphenyl-2-carbonyl)-azetidin-2-ylmethyl]-amide;

6-Chloro-imidazo[2,1-b]thiazole-5-carboxylic acid [1-(3',4'-dimethyl-biphenyl-2-carbonyl)-azetidin-2-ylmethyl]-amide;

6-Methyl-imidazo[2,1-b]thiazole-5-carboxylic acid [1-(biphenyl-2-sulfonyl)-azetidin-2-ylmethyl]-amide;

6-Trifluoromethyl-imidazo[2,1-b]thiazole-5-carboxylic acid [1-(2-methyl-5-m-tolyl-thiazole-4-carbonyl)-azetidin-2-ylmethyl]-amide;

6-Methyl-imidazo[2,1-b]thiazole-5-carboxylic acid [1-(2-methyl-5-phenyl-thiazole-4-carbonyl)-azetidin-2-ylmethyl]-amide;

3,4-Dihydro-2H-benzo[1,4]oxazine-5-carboxylic acid [1-(2-amino-5-m-tolyl-thiazole-4-carbonyl)-azetidin-2-ylmethyl]-amide;

3-Methyl-imidazo[2,1-b]thiazole-2-carboxylic acid [1-(3',4'-dimethyl-biphenyl-2-carbonyl)-azetidin-2-ylmethyl]-amide;

4-Methyl-3,4-dihydro-2H-benzo[1,4]oxazine-8-carboxylic acid [1-(2-methyl-5-m-tolyl-thiazole-4-carbonyl)-azetidin-2-ylmethyl]-amide;

3-Methyl-imidazo[2,1-b]thiazole-2-carboxylic acid [1-(2-methyl-5-m-tolyl-thiazole-4-carbonyl)-azetidin-2-ylmethyl]-amide;

Chroman-5-carboxylic acid [1-(2-methyl-5-m-tolyl-thiazole-4-carbonyl)-azetidin-2-ylmethyl]-amide;

Chroman-8-carboxylic acid [1-(2-methyl-5-m-tolyl-thiazole-4-carbonyl)-azetidin-2-ylmethyl]-amide;

3-Oxo-3,4-dihydro-2H-benzo[1,4]oxazine-5-carboxylic acid [1-(2-methyl-5-m-tolyl-thiazole-4-carbonyl)-azetidin-2-ylmethyl]-amide;

2-Methyl-imidazo[2,1-b]thiazole-5-carboxylic acid [1-(3',4'-dimethyl-biphenyl-2-carbonyl)-azetidin-2-ylmethyl]-amide;

6-Methyl-imidazo[2,1-b]thiazole-5-carboxylic acid {1-[5-(2,4-dimethyl-phenyl)-2-methyl-thiazole-4-carbonyl]-azetidin-2-ylmethyl}-amide;

3-Methyl-imidazo[2,1-b]thiazole-5-carboxylic acid [1-(2-methyl-5-m-tolyl-thiazole-4-carbonyl)-azetidin-2-ylmethyl]-amide;

2-Methyl-benzooxazole-4-carboxylic acid [1-(2-methyl-5-m-tolyl-thiazole-4-carbonyl)-azetidin-2-ylmethyl]-amide;

3,6-Dimethyl-imidazo[2,1-b]thiazole-5-carboxylic acid [1-(3',4'-dimethyl-biphenyl-2-carbonyl)-azetidin-2-ylmethyl]-amide;

6-Methyl-imidazo[2,1-b]thiazole-5-carboxylic acid {1-[5-(2-fluoro-phenyl)-2-methyl-thiazole-4-carbonyl]-azetidin-2-ylmethyl}-amide; and (2S)-Benzofuran-4-carboxylic acid [1-(naphthalene-1-sulfonyl)-azetidin-2-ylmethyl]-amide.

xxix) In another embodiment, examples of compounds of formula (I) according to embodiment i) are selected from the group consisting of:

(2R)-Benzofuran-4-carboxylic acid [1-(biphenyl-2-carbonyl)-azetidin-2-ylmethyl]-amide;

(2S)-Benzofuran-4-carboxylic acid [1-(biphenyl-2-carbonyl)-azetidin-2-ylmethyl]-amide;

(2R)-Benzofuran-4-carboxylic acid [1-(biphenyl-2-sulfonyl)-azetidin-2-ylmethyl]-amide;
(2S)-Benzofuran-4-carboxylic acid [1-(biphenyl-2-sulfonyl)-azetidin-2-ylmethyl]-amide;
(2R)-6-Methyl-imidazo[2,1-b]thiazole-5-carboxylic acid{1-[5-(4-fluoro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(4-fluoro-phenyl)-2-methyl-thiazole-4-carbonyl]-azetidin-2-ylmethyl}-amide;
(2R)-Benzofuran-4-carboxylic acid {1-[5-(4-fluoro-phenyl)-2-methyl-thiazole-4-carbonyl]-azetidin-2-ylmethyl}-amide;
(2S)-Benzofuran-4-carboxylic acid {1-[5-(4-fluoro-phenyl)-2-methyl-thiazole-4-carbonyl]-azetidin-2-ylmethyl}-amide;
(2R)-6-Methyl-imidazo[2,1-b]thiazole-5-carboxylic acid [1-(2-methyl-5-p-tolyl-thiazole-4-carbonyl)-azetidin-2-ylmethyl]-amide;
(2S)-6-Methyl-imidazo[2,1-b]thiazole-5-carboxylic acid [1-(2-methyl-5-p-tolyl-thiazole-4-carbonyl)-azetidin-2-ylmethyl]-amide;
(2S)-Benzofuran-4-carboxylic acid [1-(biphenyl-2-carbonyl)-azetidine-2-ylmethyl]-amide;
(2S)-Benzofuran-4-carboxylic acid [1-(2-trifluoromethoxy-benzenesulfonyl)-azetidin-2-ylmethyl]-amide;
(2S)-Benzofuran-4-carboxylic acid [1-(biphenyl-2-sulfonyl)-azetidin-2-ylmethyl]-amide;
(2S)-Benzofuran-4-carboxylic acid [1-(2-methoxy-benzoyl)-azetidin-2-ylmethyl]-amide;
(2R)-6-Methyl-imidazo[2,1-b]thiazole-5-carboxylic acid [1-(2-methyl-5-m-tolyl-thiazole-4-carbonyl)-azetidin-2-ylmethyl]-amide;
(2S)-6-Methyl-imidazo[2,1-b]thiazole-5-carboxylic acid [1-(2-methyl-5-m-tolyl-thiazole-4-carbonyl)-azetidin-2-ylmethyl]-amide;
(2R)-6-Methyl-imidazo[2,1-b]thiazole-5-carboxylic acid{1-[5-(3-fluoro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3-fluoro-phenyl)-2-methyl-thiazole-4-carbonyl]-azetidin-2-ylmethyl}-amide;
(2R)-6-Methyl-imidazo[2,1-b]thiazole-5-carboxylic acid {1-[2-methyl-5-(4-trifluoromethyl-phenyl)-thiazole-4-carbonyl]-azetidin-2-ylmethyl}-amide;
(2S)-6-Methyl-imidazo[2,1-b]thiazole-5-carboxylic acid {1-[2-methyl-5-(4-trifluoromethyl-phenyl)-thiazole-4-carbonyl]-azetidin-2-ylmethyl}-amide;
(2R)-6-Methyl-imidazo[2,1-b]thiazole-5-carboxylic acid{1-[5-(4-ethyl-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(4-ethyl-phenyl)-2-methyl-thiazole-4-carbonyl]-azetidin-2-ylmethyl}-amide;
(2S)-Benzofuran-4-carboxylic acid [1-(3-trifluoromethyl-benzoyl)-azetidin-2-ylmethyl]-amide;
(2S)-Benzofuran-4-carboxylic acid [1-(3',4'-dimethyl-biphenyl-2-carbonyl)-azetidin-2-ylmethyl]-amide;
(2S)-Benzofuran-4-carboxylic acid{1-[5-(4-fluoro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3,4-dimethyl-phenyl)-2-methyl-thiazole-4-carbonyl]-azetidin-2-ylmethyl}-amide;
(2S)-6-Methyl-imidazo[2,1-b]thiazole-5-carboxylic acid [1-(2-methyl-5-m-tolyl-thiazole-4-carbonyl)-azetidin-2-ylmethyl]-amide;
(2S)-6-Methyl-imidazo[2,1-b]thiazole-5-carboxylic acid [1-(3',4'-dimethyl-biphenyl-2-carbonyl)-azetidin-2-ylmethyl]-amide;
(2S)-6-Methyl-imidazo[2,1-b]thiazole-5-carboxylic acid [1-(2-amino-5-m-tolyl-thiazole-4-carbonyl)-azetidin-2-ylmethyl]-amide;
(2S)-6-Chloro-imidazo[2,1-b]thiazole-5-carboxylic acid [1-(2-methyl-5-m-tolyl-thiazole-4-carbonyl)-azetidin-2-ylmethyl]-amide;
(2S)-6-Chloro-imidazo[2,1-b]thiazole-5-carboxylic acid [1-(2-amino-5-m-tolyl-thiazole-4-carbonyl)-azetidin-2-ylmethyl]-amide;
(2R)-Benzofuran-4-carboxylic acid [1-(3',4'-dimethyl-biphenyl-2-carbonyl)-azetidin-2-ylmethyl]-amide;
(2S)-Benzofuran-4-carboxylic acid [1-(3',4'-dimethyl-biphenyl-2-carbonyl)-azetidin-2-ylmethyl]-amide;
(2R)-6-Methyl-imidazo[2,1-b]thiazole-5-carboxylic acid{1-[5-(3,4-dimethyl-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3,4-dimethyl-phenyl)-2-methyl-thiazole-4-carbonyl]-azetidin-2-ylmethyl}-amide;
(2R)-6-Methyl-imidazo[2,1-b]thiazole-5-carboxylic acid{1-[5-(3-methoxy-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3-methoxy-phenyl)-2-methyl-thiazole-4-carbonyl]-azetidin-2-ylmethyl}-amide;
(2R)-6-Methyl-imidazo[2,1-b]thiazole-5-carboxylic acid{1-[5-(3-chloro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3-chloro-phenyl)-2-methyl-thiazole-4-carbonyl]-azetidin-2-ylmethyl}-amide;
(2R)-6-Methyl-imidazo[2,1-b]thiazole-5-carboxylic acid{1-[2-methyl-5-(3-trifluoromethyl-phenyl)-thiazole-4-carbonyl]-azetidin-2-ylmethyl}-amide;
(2S)-6-Methyl-imidazo[2,1-b]thiazole-5-carboxylic acid{1-[2-methyl-5-(3-trifluoromethyl-phenyl)-thiazole-4-carbonyl]-azetidin-2-ylmethyl}-amide;
(2R)-6-Methyl-imidazo[2,1-b]thiazole-5-carboxylic acid{1-[5-(4-methoxy-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(4-methoxy-phenyl)-2-methyl-thiazole-4-carbonyl]-azetidin-2-ylmethyl}-amide;
(2R)-6-Methyl-imidazo[2,1-b]thiazole-5-carboxylic acid{1-[5-(3,5-difluoro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3,5-difluoro-phenyl)-2-methyl-thiazole-4-carbonyl]-azetidin-2-ylmethyl}-amide;
(2R)-6-Methyl-imidazo[2,1-b]thiazole-5-carboxylic acid{1-[5-(3-bromo-4-fluoro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3-bromo-4-fluoro-phenyl)-2-methyl-thiazole-4-carbonyl]-azetidin-2-ylmethyl}-amide;
(2R)-6-Methyl-imidazo[2,1-b]thiazole-5-carboxylic acid{1-[5-(4-chloro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(4-chloro-phenyl)-2-methyl-thiazole-4-carbonyl]-azetidin-2-ylmethyl}-amide;
(2R)-6-Methyl-imidazo[2,1-b]thiazole-5-carboxylic acid{1-[5-(3,4-dichloro-phenyl)-2-methyl-thiazole-4-carbonyl]-azetidin-2-ylmethyl}-amide;

(2S)-6-Methyl-imidazo[2,1-b]thiazole-5-carboxylic acid{1-[5-(3,4-dichloro-phenyl)-2-methyl-thiazole-4-carbonyl]-azetidin-2-ylmethyl}-amide;
(2R)-6-Chloro-imidazo[2,1-b]thiazole-5-carboxylic acid{1-[5-(3,4-dimethyl-phenyl)-2-methyl-thiazole-4-carbonyl]-azetidin-2-ylmethyl}-amide;
(2S)-6-Chloro-imidazo[2,1-b]thiazole-5-carboxylic acid{1-[5-(3,4-dimethyl-phenyl)-2-methyl-thiazole-4-carbonyl]-azetidin-2-ylmethyl}-amide;
(2R)-6-Chloro-imidazo[2,1-b]thiazole-5-carboxylic acid [1-(2-methyl-5-m-tolyl-thiazole-4-carbonyl)-azetidin-2-ylmethyl]-amide;
(2S)-6-Chloro-imidazo[2,1-b]thiazole-5-carboxylic acid [1-(2-methyl-5-m-tolyl-thiazole-4-carbonyl)-azetidin-2-ylmethyl]-amide;
(2R)-2-Methyl-benzofuran-4-carboxylic acid [1-(2-methyl-5-m-tolyl-thiazole-4-carbonyl)-azetidin-2-ylmethyl]-amide;
(2S)-2-Methyl-benzofuran-4-carboxylic acid [1-(2-methyl-5-m-tolyl-thiazole-4-carbonyl)-azetidin-2-ylmethyl]-amide;
(2R)-2H-Chromene-5-carboxylic acid [1-(2-methyl-5-m-tolyl-thiazole-4-carbonyl)-azetidin-2-ylmethyl]-amide;
(2S)-2H-Chromene-5-carboxylic acid [1-(2-methyl-5-m-tolyl-thiazole-4-carbonyl)-azetidin-2-ylmethyl]-amide;
(2R)-Benzooxazole-4-carboxylic acid [1-(2-methyl-5-m-tolyl-thiazole-4-carbonyl)-azetidin-2-ylmethyl]-amide;
(2S)-Benzooxazole-4-carboxylic acid [1-(2-methyl-5-m-tolyl-thiazole-4-carbonyl)-azetidin-2-ylmethyl]-amide;
(2R)-Benzofuran-3-carboxylic acid [1-(2-methyl-5-m-tolyl-thiazole-4-carbonyl)-azetidin-2-ylmethyl]-amide;
(2S)-Benzofuran-3-carboxylic acid [1-(2-methyl-5-m-tolyl-thiazole-4-carbonyl)-azetidin-2-ylmethyl]-amide;
(2R)-2-Methyl-benzofuran-3-carboxylic acid [1-(2-methyl-5-m-tolyl-thiazole-4-carbonyl)-azetidin-2-ylmethyl]-amide;
(2S)-2-Methyl-benzofuran-3-carboxylic acid [1-(2-methyl-5-m-tolyl-thiazole-4-carbonyl)-azetidin-2-ylmethyl]-amide;
(2R)-3,5-Dimethyl-imidazo[2,1-b]thiazole-6-carboxylic acid [1-(2-methyl-5-m-tolyl-thiazole-4-carbonyl)-azetidin-2-ylmethyl]-amide;
(2S)-3,5-Dimethyl-imidazo[2,1-b]thiazole-6-carboxylic acid [1-(2-methyl-5-m-tolyl-thiazole-4-carbonyl)-azetidin-2-ylmethyl]-amide;
(2R)-3,4-Dihydro-2H-benzo[1,4]oxazine-5-carboxylic acid [1-(2-methyl-5-m-tolyl-thiazole-4-carbonyl)-azetidin-2-ylmethyl]-amide;
(2S)-3,4-Dihydro-2H-benzo[1,4]oxazine-5-carboxylic acid [1-(2-methyl-5-m-tolyl-thiazole-4-carbonyl)-azetidin-2-ylmethyl]-amide;
(2R)-5-Methyl-imidazo[2,1-b]thiazole-6-carboxylic acid [1-(2-methyl-5-m-tolyl-thiazole-4-carbonyl)-azetidin-2-ylmethyl]-amide;
(2S)-5-Methyl-imidazo[2,1-b]thiazole-6-carboxylic acid [1-(2-methyl-5-m-tolyl-thiazole-4-carbonyl)-azetidin-2-ylmethyl]-amide;
(2R)-4-Methyl-3-oxo-3,4-dihydro-2H-benzo[1,4]oxazine-8-carboxylic acid [1-(2-methyl-5-m-tolyl-thiazole-4-carbonyl)-azetidin-2-ylmethyl]-amide;
(2S)-4-Methyl-3-oxo-3,4-dihydro-2H-benzo[1,4]oxazine-8-carboxylic acid [1-(2-methyl-5-m-tolyl-thiazole-4-carbonyl)-azetidin-2-ylmethyl]-amide;
(2R)-Imidazo[2,1-b]thiazole-5-carboxylic acid [1-(2-methyl-5-m-tolyl-thiazole-4-carbonyl)-azetidin-2-ylmethyl]-amide;
(2S)-Imidazo[2,1-b]thiazole-5-carboxylic acid [1-(2-methyl-5-m-tolyl-thiazole-4-carbonyl)-azetidin-2-ylmethyl]-amide;
(2R)-Imidazo[2,1-b]thiazole-5-carboxylic acid [1-(3',4'-dimethyl-biphenyl-2-carbonyl)-azetidin-2-ylmethyl]-amide;
(2S)-Imidazo[2,1-b]thiazole-5-carboxylic acid [1-(3',4'-dimethyl-biphenyl-2-carbonyl)-azetidin-2-ylmethyl]-amide;
(2R)-3-Methyl-imidazo[2,1-b]thiazole-5-carboxylic acid [1-(3',4'-dimethyl-biphenyl-2-carbonyl)-azetidin-2-ylmethyl]-amide;
(2S)-3-Methyl-imidazo[2,1-b]thiazole-5-carboxylic acid [1-(3',4'-dimethyl-biphenyl-2-carbonyl)-azetidin-2-ylmethyl]-amide;
(2R)-3,5-Dimethyl-imidazo[2,1-b]thiazole-6-carboxylic acid [1-(3',4'-dimethyl-biphenyl-2-carbonyl)-azetidin-2-ylmethyl]-amide;
(2S)-3,5-Dimethyl-imidazo[2,1-b]thiazole-6-carboxylic acid [1-(3',4'-dimethyl-biphenyl-2-carbonyl)-azetidin-2-ylmethyl]-amide;
(2R)-6-Chloro-imidazo[2,1-b]thiazole-5-carboxylic acid [1-(3',4'-dimethyl-biphenyl-2-carbonyl)-azetidin-2-ylmethyl]-amide;
(2S)-6-Chloro-imidazo[2,1-b]thiazole-5-carboxylic acid [1-(3',4'-dimethyl-biphenyl-2-carbonyl)-azetidin-2-ylmethyl]-amide;
(2R)-6-Methyl-imidazo[2,1-b]thiazole-5-carboxylic acid [1-(biphenyl-2-sulfonyl)-azetidin-2-ylmethyl]-amide;
(2S)-6-Methyl-imidazo[2,1-b]thiazole-5-carboxylic acid [1-(biphenyl-2-sulfonyl)-azetidin-2-ylmethyl]-amide;
(2R)-6-Trifluoromethyl-imidazo[2,1-b]thiazole-5-carboxylic acid [1-(2-methyl-5-m-tolyl-thiazole-4-carbonyl)-azetidin-2-ylmethyl]-amide;
(2S)-6-Trifluoromethyl-imidazo[2,1-b]thiazole-5-carboxylic acid [1-(2-methyl-5-m-tolyl-thiazole-4-carbonyl)-azetidin-2-ylmethyl]-amide;
(2R)-6-Methyl-imidazo[2,1-b]thiazole-5-carboxylic acid [1-(2-methyl-5-phenyl-thiazole-4-carbonyl)-azetidin-2-ylmethyl]-amide;
(2S)-6-Methyl-imidazo[2,1-b]thiazole-5-carboxylic acid [1-(2-methyl-5-phenyl-thiazole-4-carbonyl)-azetidin-2-ylmethyl]-amide;
(2R)-3,4-Dihydro-2H-benzo[1,4]oxazine-5-carboxylic acid [1-(2-amino-5-m-tolyl-thiazole-4-carbonyl)-azetidin-2-ylmethyl]-amide;
(2S)-3,4-Dihydro-2H-benzo[1,4]oxazine-5-carboxylic acid [1-(2-amino-5-m-tolyl-thiazole-4-carbonyl)-azetidin-2-ylmethyl]-amide;
(2R)-3-Methyl-imidazo[2,1-b]thiazole-2-carboxylic acid [1-(3',4'-dimethyl-biphenyl-2-carbonyl)-azetidin-2-ylmethyl]-amide;
(2S)-3-Methyl-imidazo[2,1-b]thiazole-2-carboxylic acid [1-(3',4'-dimethyl-biphenyl-2-carbonyl)-azetidin-2-ylmethyl]-amide;
(2R)-4-Methyl-3,4-dihydro-2H-benzo[1,4]oxazine-8-carboxylic acid [1-(2-methyl-5-m-tolyl-thiazole-4-carbonyl)-azetidin-2-ylmethyl]-amide;
(2S)-4-Methyl-3,4-dihydro-2H-benzo[1,4]oxazine-8-carboxylic acid [1-(2-methyl-5-m-tolyl-thiazole-4-carbonyl)-azetidin-2-ylmethyl]-amide;
(2R)-3-Methyl-imidazo[2,1-b]thiazole-2-carboxylic acid [1-(2-methyl-5-m-tolyl-thiazole-4-carbonyl)-azetidin-2-ylmethyl]-amide;
(2S)-3-Methyl-imidazo[2,1-b]thiazole-2-carboxylic acid [1-(2-methyl-5-m-tolyl-thiazole-4-carbonyl)-azetidin-2-ylmethyl]-amide;

(2R)-Chroman-5-carboxylic acid [1-(2-methyl-5-m-tolyl-thiazole-4-carbonyl)-azetidin-2-ylmethyl]-amide;
(2S)-Chroman-5-carboxylic acid [1-(2-methyl-5-m-tolyl-thiazole-4-carbonyl)-azetidin-2-ylmethyl]-amide;
(2R)-Chroman-8-carboxylic acid [1-(2-methyl-5-m-tolyl-thiazole-4-carbonyl)-azetidin-2-ylmethyl]-amide;
(2S)-Chroman-8-carboxylic acid [1-(2-methyl-5-m-tolyl-thiazole-4-carbonyl)-azetidin-2-ylmethyl]-amide;
(2R)-3-Oxo-3,4-dihydro-2H-benzo[1,4]oxazine-5-carboxylic acid [1-(2-methyl-5-m-tolyl-thiazole-4-carbonyl)-azetidin-2-ylmethyl]-amide;
(2S)-3-Oxo-3,4-dihydro-2H-benzo[1,4]oxazine-5-carboxylic acid [1-(2-methyl-5-m-tolyl-thiazole-4-carbonyl)-azetidin-2-ylmethyl]-amide;
(2R)-2-Methyl-imidazo[2,1-b]thiazole-5-carboxylic acid [1-(3',4'-dimethyl-biphenyl-2-carbonyl)-azetidin-2-ylmethyl]-amide;
(2S)-2-Methyl-imidazo[2,1-b]thiazole-5-carboxylic acid [1-(3',4'-dimethyl-biphenyl-2-carbonyl)-azetidin-2-ylmethyl]-amide;
(2R)-6-Methyl-imidazo[2,1-b]thiazole-5-carboxylic acid{1-[5-(2,4-dimethyl-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(2,4-dimethyl-phenyl)-2-methyl-thiazole-4-carbonyl]-azetidin-2-ylmethyl}-amide;
(2R)-3-Methyl-imidazo[2,1-b]thiazole-5-carboxylic acid [1-(2-methyl-5-m-tolyl-thiazole-4-carbonyl)-azetidin-2-ylmethyl]-amide;
(2S)-3-Methyl-imidazo[2,1-b]thiazole-5-carboxylic acid [1-(2-methyl-5-m-tolyl-thiazole-4-carbonyl)-azetidin-2-ylmethyl]-amide;
(2R)-2-Methyl-benzooxazole-4-carboxylic acid [1-(2-methyl-5-m-tolyl-thiazole-4-carbonyl)-azetidin-2-ylmethyl]-amide;
(2S)-2-Methyl-benzooxazole-4-carboxylic acid [1-(2-methyl-5-m-tolyl-thiazole-4-carbonyl)-azetidin-2-ylmethyl]-amide;
(2R)-3,6-Dimethyl-imidazo[2,1-b]thiazole-5-carboxylic acid [1-(3',4'-dimethyl-biphenyl-2-carbonyl)-azetidin-2-ylmethyl]-amide;
(2S)-3,6-Dimethyl-imidazo[2,1-b]thiazole-5-carboxylic acid [1-(3',4'-dimethyl-biphenyl-2-carbonyl)-azetidin-2-ylmethyl]-amide;
(2R)-6-Methyl-imidazo[2,1-b]thiazole-5-carboxylic acid{1-[5-(2-fluoro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(2-fluoro-phenyl)-2-methyl-thiazole-4-carbonyl]-azetidin-2-ylmethyl}-amide; and
(2S)-Benzofuran-4-carboxylic acid [1-(naphthalene-1-sulfonyl)-azetidin-2-ylmethyl]-amide.

The compounds of formula (I) and their pharmaceutically acceptable salts can be used as medicaments, e.g. in the form of pharmaceutical compositions for enteral or parental administration.

A further aspect of the invention is a pharmaceutical composition containing at least one compound according to formula (I) and a pharmaceutically acceptable carrier material.

The present invention also concerns a process for the preparation of a pharmaceutical composition comprising a compound of general formula (I) by mixing one or more active ingredients according to formula (I) with a carrier material in a manner known per se.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I).

The compounds according to formula (I) may be used for the preparation of a medicament and are suitable for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

The compounds according to formula (I) may be used for the preparation of a medicament and are suitable for the prevention or treatment of diseases selected from the group consisting of dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions. Compounds of formula (I) are particularly suitable for use in the treatment of diseases or disorders selected from the group consisting of eating or drinking disorders, all types of sleep disorders, or cognitive dysfunctions in the healthy population and in psychiatric and neurologic disorders.

Another aspect of the present invention is a method for the treatment or prophylaxis of diseases, which are related to the orexin receptors such as eating disorders or sleep disorders comprising the administration to a patient a therapeutically effective amount of a compound of formula (I).

Compounds of formula (I) may be used for the preparation of a medicament and are particularly suitable for the prevention or treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders.

In another preferred embodiment of the invention compounds of formula (I) may be used for the preparation of a medicament and are particularly suitable for the preparation of a medicament for the treatment of diseases or disorders selected from the group consisting of eating disorders that comprise metabolic dysfunction; dysregulated appetite control; compulsive obesities; emeto-bulimia or anorexia nervosa.

Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake.

In a further preferred embodiment of the invention compounds of formula (I) may be used for the preparation of a medicament and are particularly suitable for the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components.

In another preferred embodiment of the invention compounds of formula (I) may be used for the preparation of a medicament and are particularly suitable for the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of formula (I) may be used for the preparation of a medicament and are particularly suitable for the treatment of diseases or disorders selected from the group consisting of psychoactive substance use and abuse that comprise all types of psychological or physical addictions and their related tolerance and dependence components.

A further aspect of the invention is a process for the preparation of compounds of formula (I). Compounds according to formula (I) of the present invention can be prepared according to the general sequence of reactions outlined in the schemes below wherein X, $R^1$, $R^2$, $R^3$, and $R^4$ are as defined in the description of formula (I). Substituents R and R' which are attached to an aryl, a phenyl, or a heteroaryl group as used in the schemes below represent the respective substituents as defined for the corresponding group in the definitions above. Other abbreviations used are defined in the experimental section. In some instances the generic groups X, $R^1$, $R^2$, $R^3$, and $R^4$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as are necessary are in place. The compounds obtained may also be converted into pharmaceutically acceptable salts thereof in a manner known per se.

The compounds of formula (I) may be prepared by reaction commercially available 2-(N-Boc-aminomethyl)azetidine (1) with the respective carboxylic acid derivative $R^1$—$CO_2H$ in the presence of a coupling reagent such as PyBOP leading to amide intermediates (2), wherein X represents C(O). Alternatively, coupling with the respective commercially available sulfonyl chloride $R^1$—$SO_2Cl$ under basic reaction conditions leads to the corresponding sulfonamide intermediates (2), wherein X represents $SO_2$. The resulting intermediates (2) are transformed to compounds of formula (I) by cleavage of the Boc protecting group under acidic conditions such as TFA followed by amide formation with the respective carboxylic acid $R^2$—$CO_2H$ as shown in scheme 1.

Scheme 1: Synthesis of compounds of formula (I)

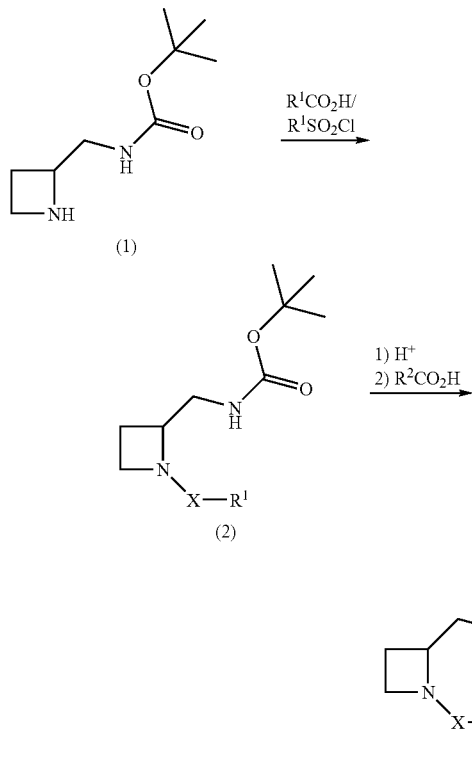

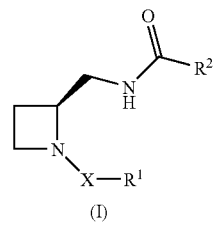

Esterification of (3) followed by treatment with ammonia in MeOH leads to the primary amide (4). Reduction by reaction with $BH_3$ in THF followed by coupling with the respective carboxylic acid $R^2$—$CO_2H$ in the presence of a coupling reagent such as TBTU leads to the amide intermediate (5). Subsequent cleavage of the Boc protecting group under acidic condition followed by coupling with the respective carboxylic acid derivative $R^1$—$CO_2H$ in the presence of a coupling reagent such as TBTU, or the respective sulfonyl chloride $R^1$—$SO_2Cl$ in presence of a base such as DIEA, provides the desired compounds of formula (I) as shown in scheme 2.

Preparation of Carboxylic Acids $R^1$—COOH

Carboxylic acid derivatives $R^1$—COOH wherein $R^1$ represents a 5-phenyl-thiazole-4-yl derivative are commercially available or can be synthesised according to scheme 3.

Scheme 3: Synthesis of carboxylic acids $R^1$—COOH wherein $R^1$ represents a 5-phenylthiazole-4-yl derivative

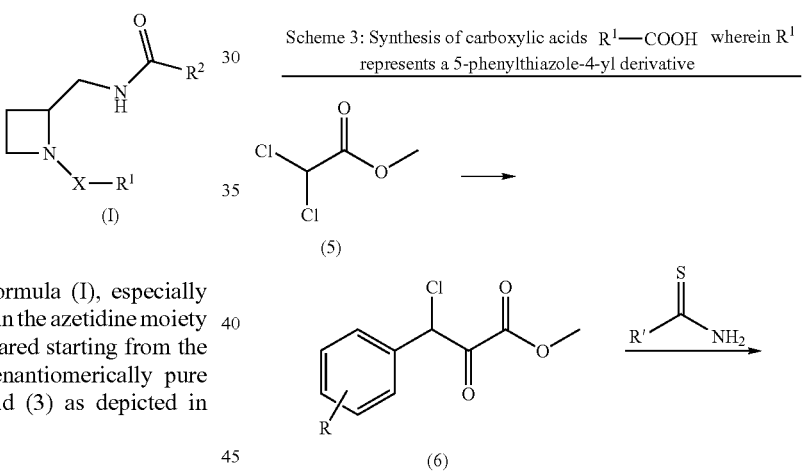

Alternatively, the compounds of formula (I), especially those compounds of formula (I), wherein the azetidine moiety has the (S)-configuration may be prepared starting from the commercially available racemic or enantiomerically pure (2S)-1-Boc-azetidine-2-carboxylic acid (3) as depicted in scheme 2.

Scheme 2: Alternative synthesis of compounds of formula (I)

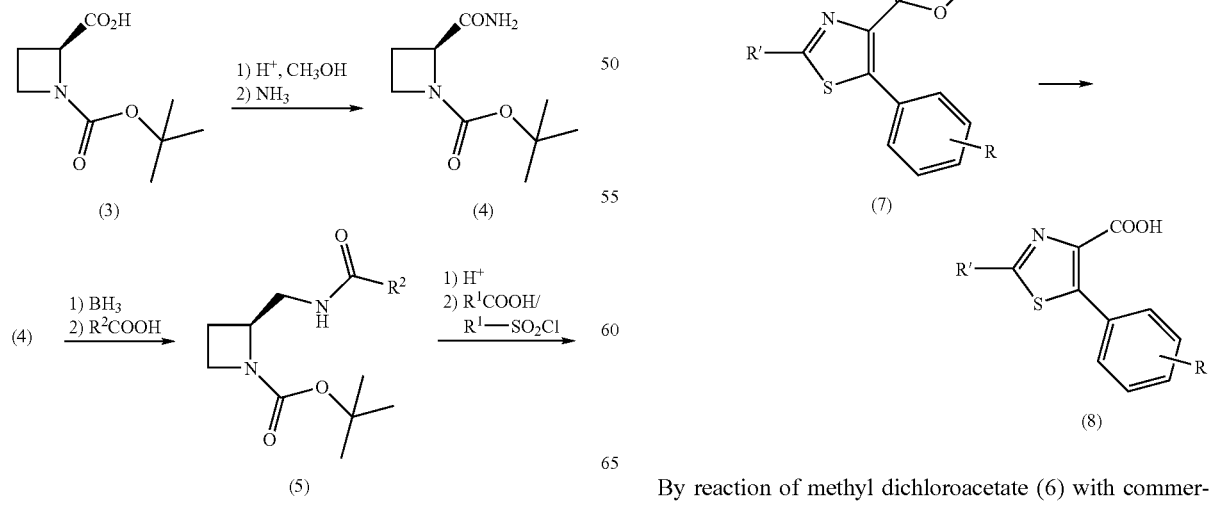

By reaction of methyl dichloroacetate (6) with commercially available benzaldehyde derivatives in the presence of a base such as KOtBu in an aprotic polar solvent such as THF at RT 3-chloro-2-oxo-propionic acid ester derivatives (7) are obtained (Hamamoto H. et al Tetrahedron *Asymmetry* 2000, 11, 4485-4497). Compounds of structure (7) can be transformed by reaction with commercially available thioamides or thioureas R'—C(S)—NH$_2$ at RT in solvents such as MeCN to provide thiazol-4-carboxylic acid ester derivatives (8) (U.S. Pat. No. 3,282,927). 5-Phenyl-thiazol-4-carboxylic acid ester derivatives (8), R' being —NH$_2$, can be transformed into compounds (8), R' being bromo, via Sandmeyer reaction. Saponification of the ester function using methods known in the art such as treatment with a base such as NaOH in a solvent such as MeOH provides the corresponding 5-phenyl-thiazol-4-carboxylic acid derivatives (9). The respective benzaldehydes are commercially available or well known in the art. Thioamides of formula R'—C(S)—NH$_2$, wherein R' represents (C$_{1-4}$)alkyl are commercially available or, alternatively, can be synthesized from commercially available carboxamides with Lawesson's reagent.

Carboxylic acid derivatives R$^1$—COOH wherein R$^1$ represents a 4-phenyl-thiazole-5-yl derivative are commercially available or synthesised according to scheme 4.

Scheme 4: Synthesis of carboxylic acids R$^1$—COOH wherein R$^1$ represents a 4-phenylthiazole-5-yl derivative

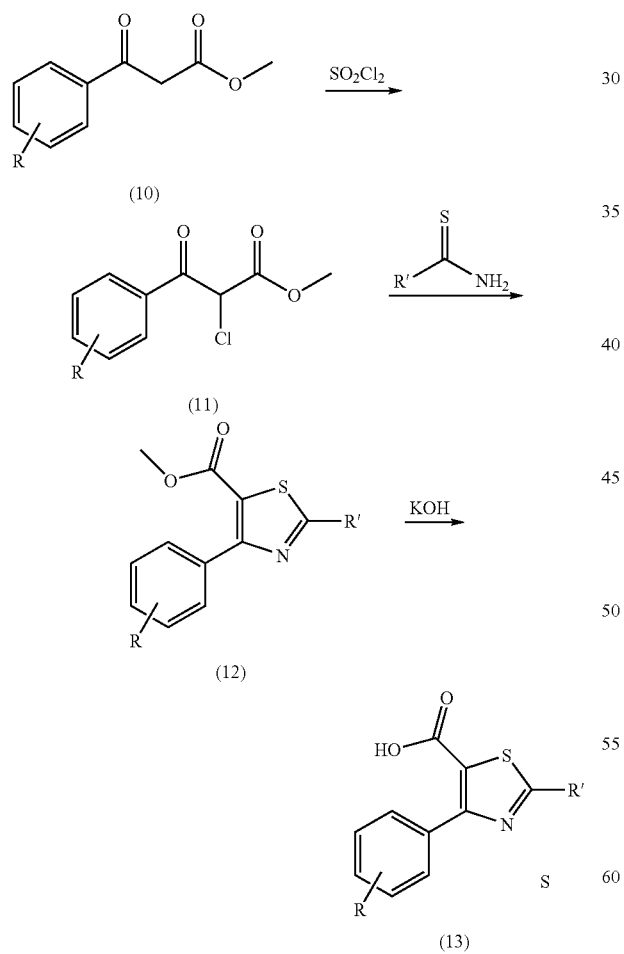

By refluxing a commercially available 3-oxo-propionic acid ester derivative (10) with SO$_2$Cl$_2$ in a solvent such as CHCl$_3$ the corresponding 2-chloro-3-oxo-propionic acid ester derivatives (11) can be obtained. Compounds of structure (11) can be transformed by reaction with commercially available thioamides R'—C(S)—NH$_2$ at reflux temperature in solvents such as THF in presence of a base such as NaHCO$_3$ to the corresponding thiazol-5-carboxylic acid ester derivatives (12). Saponification of the ester function using methods known in the art such as treatment with a base such as KOH in a solvent such as ethanol provides the corresponding 4-phenyl-thiazol-5-carboxylic acid derivatives (13).

Carboxylic acid derivatives R$^1$—COOH wherein R$^1$ represents a 2-methyl-5-phenyl-oxazole-4-yl derivative are commercially available or synthesised according to scheme 5.

Scheme 5: Synthesis of carboxylic acid R$^1$—COOH wherein R$^1$ represents a 2-methyl-5-phenyl-oxazole-4-yl derivative

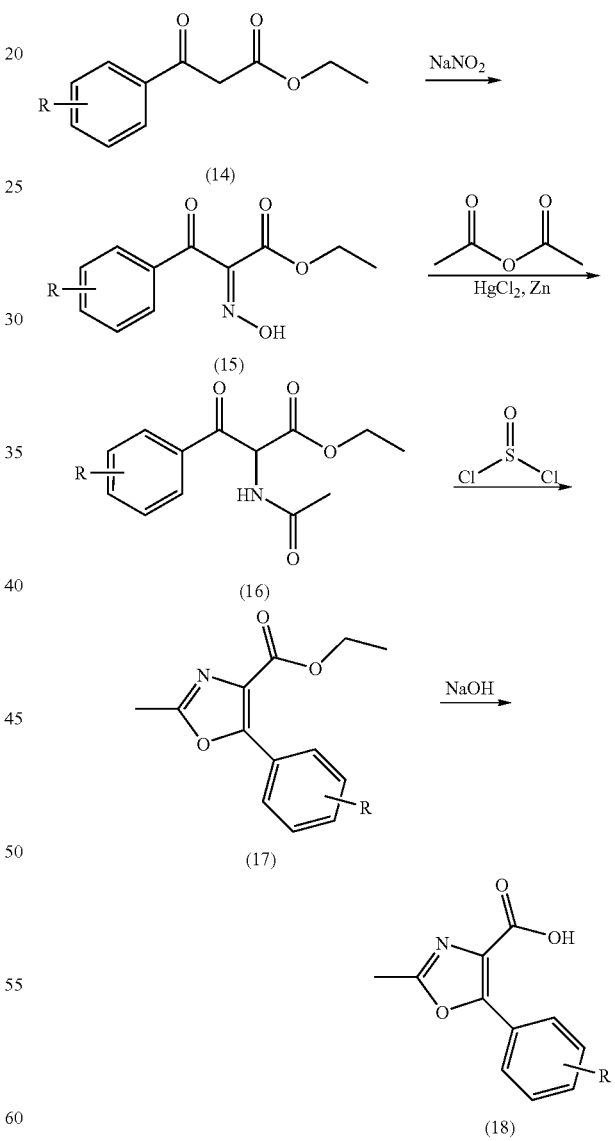

By reaction of a commercially available 3-oxo-propionic acid ester derivative (14) with an aqueous solution sodium nitrite in presence of an acid such as glacial acetic acid the corresponding oxime derivative (15) can be obtained. The 2-acetamido-3-oxo-propionic acid ester derivative (16) can be synthesized from compounds of structure (15) using acetic anhydride in presence of an acid such as glacial acetic acid and catalytic amounts of metal chlorides such as mercury chloride and zinc powder. Cyclization to the corresponding 2-methyl-5-phenyl-oxazole-4 carboxylic acid ester derivative (17) can be achieved under dehydrating conditions such as thionyl chloride in chloroform. Saponification of the ester function using methods known in the art such as treatment with a base such as NaOH in solvent mixtures such as ethanol/water provides the corresponding 2-methyl-5-phenyl-oxazole-4 carboxylic acid derivative (18).

Carboxylic acid derivatives $R^1$—COOH wherein $R^1$ represents a biphen-2-yl derivative are commercially available or can be synthesised according to scheme 6.

Scheme 6: Synthesis of carboxylic acid $R^1$—COOH wherein $R^1$ represents a biphen-2-yl derivative

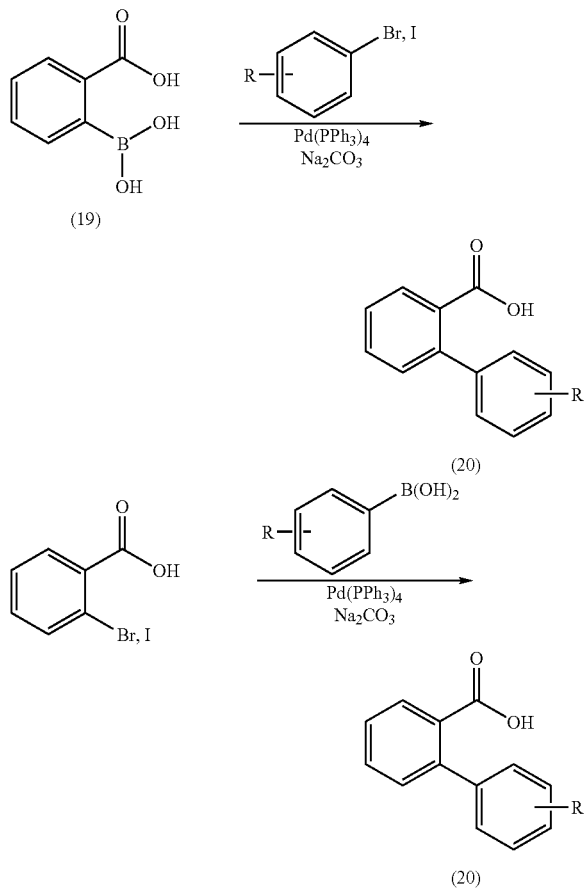

Reaction of commercially available (2-carboxyphenyl)-boronic acid derivatives (19) or esters thereof with commercially available phenyl-bromides or phenyl-iodides in presence of a catalyst such as Pd(PPh$_3$)$_4$ and a base such as Na$_2$CO$_3$ under heating in a solvent such as toluene, dioxane, THF provides, after saponification, if needed, of the ester using well known methods, the corresponding biphenyl-2-carboxylic acid derivatives (20). Alternatively, reaction of commercially available 2-bromo-, or 2-iodo-benzoic acid, or esters thereof, with commercially available phenyl-boronic acid derivatives using the conditions described before provides the corresponding biphenyl-2-carboxylic acid derivatives (20).

Synthesis of Carboxylic Acids $R^2$—COOH

Carboxylic acids of formula $R^2$—COOH are commercially available or well known in the art (Lit. e.g. WO2001/96302; T. Eicher, S. Hauptmann "The chemistry of Heterocycles: Structure, Reactions, Syntheses, and Applications", 2nd Edition 2003, Wiley, ISBN 978-3-527-30720-3).

Carboxylic acid derivatives $R^2$—COOH which represent an imidazo[2,1-b]thiazole-carboxylic acid derivative are commercially available, or can be synthesised according to the literature according to scheme 7.

Scheme 7: Synthesis of carboxylic acids $R^2$—COOH which represent an imidazo[2,1-b]thiazole-carboxylic acid derivative

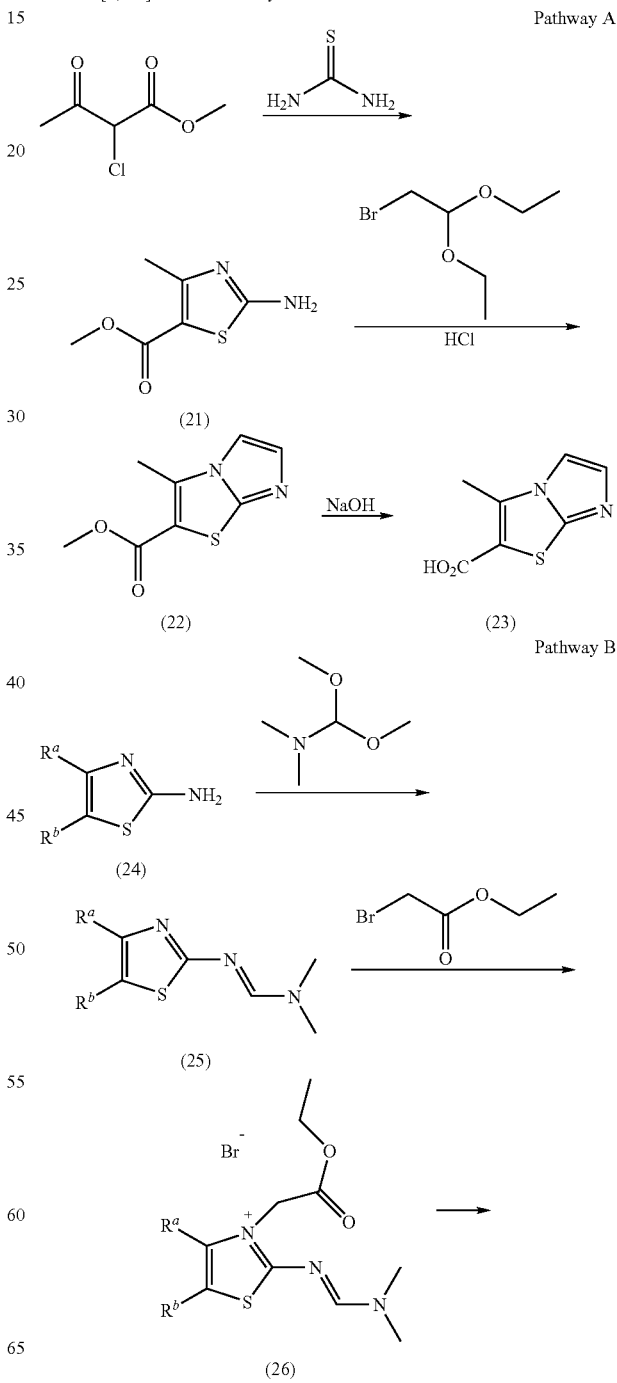

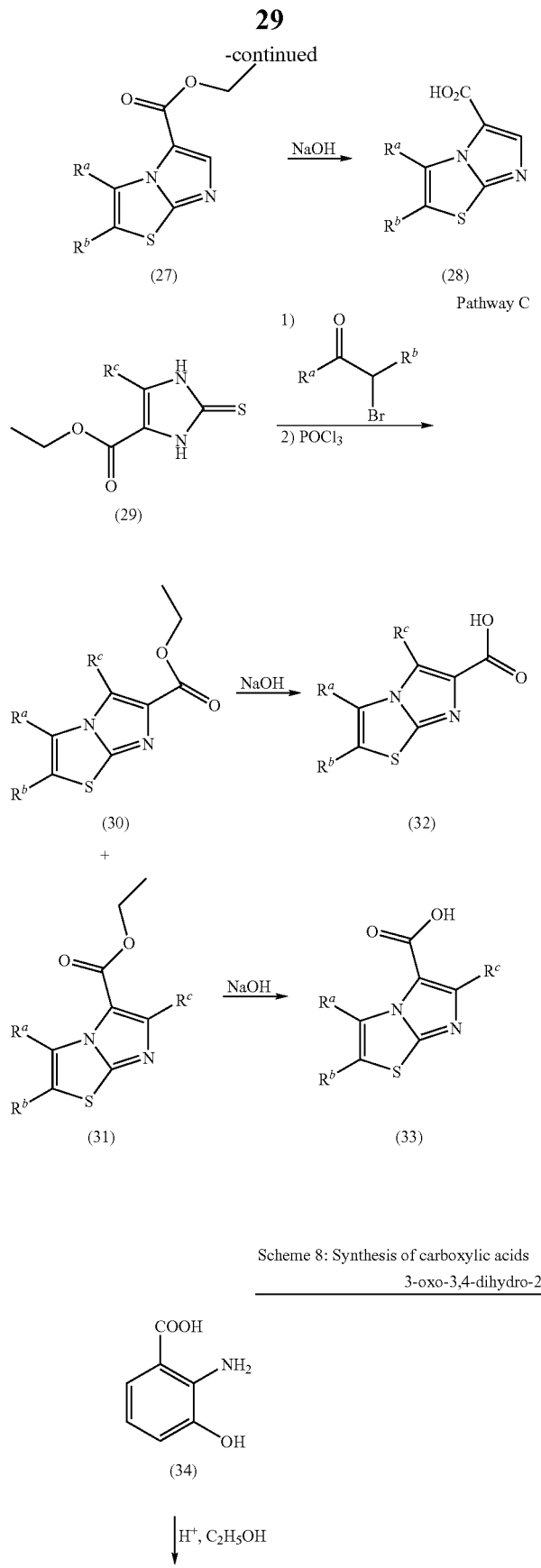

(27) (28)

Pathway C (29)

(30) (32)

+

(31) (33)

Pathway A: By reaction of commercially available 2-chloro-3-oxo-butyric acid methyl ester with thiourea the aminothiazole (21) can be obtained. Transformation to ester (22) can be accomplished with bromoacetaldehyde which can be generated in-situ from bromoacetaldehyde diethylacetal under acidic conditions. After saponification with bases such as sodium hydroxide the desired acid (23) can be obtained (WO02/46158)

Pathway B: By heating an commercially available aminothiazole derivative of structure (24) with N,N-dimethylformamide dimethylacetal in a solvent such as toluene formamidine derivatives (25) can be obtained. They can be alkylated with ethyl bromoacetate yielding the respective thiazolium bromide (26) which can be cyclised with strong bases such as DBU to the ester (27). Saponification of the ester function using methods known in the art such as treatment with a base such as NaOH in a solvent such as ethanol/water provides the corresponding imidazo[2,1-b]thiazole-5-carboxylic acid derivatives (28) (WO95/29922 and U.S. Pat. No. 6,191,124).

Pathway C: By reaction of a 4-ethoxycarbonylimidazo-2-thiol derivative (29) with a bromo-ketone derivative in EtOH followed by cyclisation with $POCl_3$ to yield a mixture of the two regioisomeric ester derivatives (30) and (31) which can be separated by FC. Saponification with a base such as NaOH in a solvent such as ethanol/water provide the desired imidazo[2,1-b]thiazole carboxylic acids (32) and (33) (U.S. Pat. No. 4,267,339 and DE2505068). 4-Ethoxycarbonylimidazo-2-thiol derivatives (29) are commercially available or, alternatively, can be synthesized from the corresponding commercially available imidazolones with Lawesson's reagent. Alternatively, acids of structure (33) wherein $R^c$ represents methyl, chloro, or trifluoromethyl can be synthesized by alkylating and cyclizing compounds of structure (24) with bromoacetone, chloroacetaldehyde, or 3-bromo-1,1,1-trifluoro-acetone, respectively, followed by formylation of the obtained imidazo[2,1-b]thiazole in position 5 with $POCl_3$/DMF and oxidation of the obtained aldehyde to the corresponding carboxylic acid according to well known methods. In scheme 7 preferably $R^a$, $R^b$ and $R^e$ independently represent hydrogen or methyl.

Carboxylic acid derivatives $R^2$—COOH which represent an 3,4-dihydro-2H-benzo[1,4]oxazinyl- or 3-oxo-3,4-dihydro-2H-benzo[1,4]oxazinyl-carboxylic acid derivative are commercially available, or can be synthesised according to the literature according to schemes 8 and 9.

Scheme 8: Synthesis of carboxylic acids $R^2$—COOH which represents an 3,4-dihydro-2H-benzo[1,4] oxazinyl- or 3-oxo-3,4-dihydro-2H-benzo[1,4] oxazinyl-carboxylic acid derivative

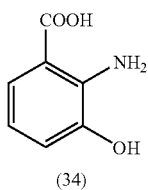

(34)

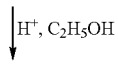

$H^+$, $C_2H_5OH$

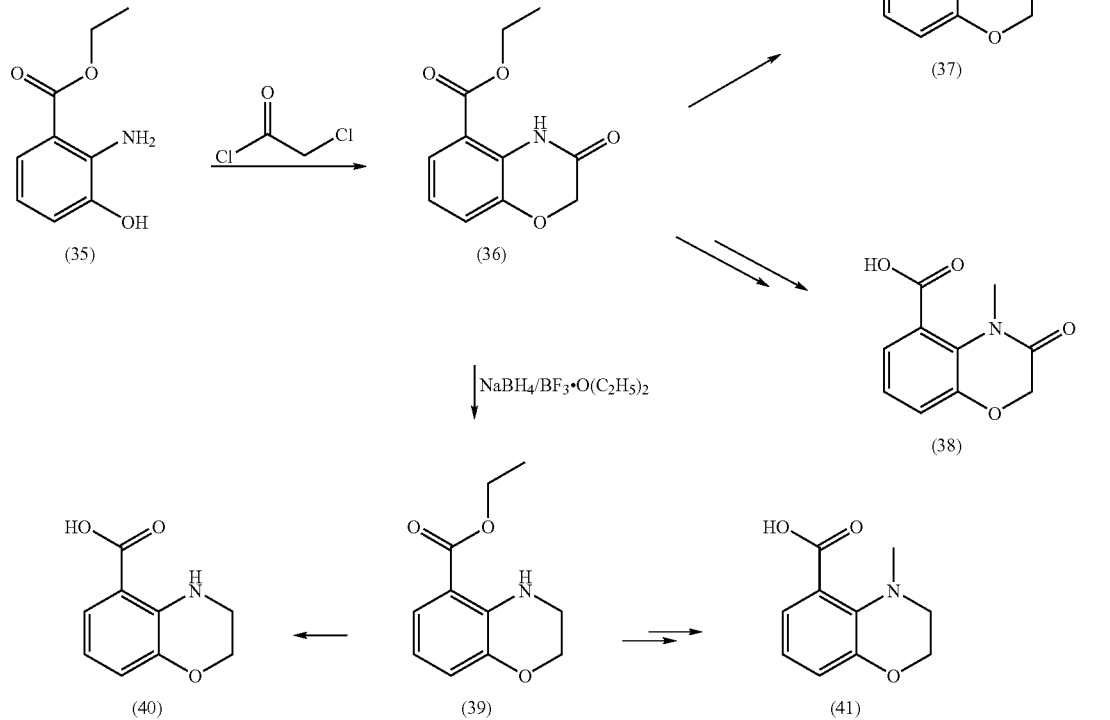
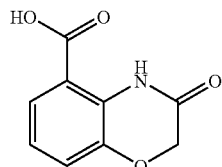
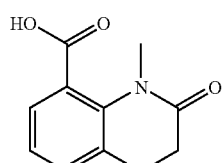

Esterification of 3-hydroxy-anthranilic acid (34) with concentrated sulphuric acid in MeOH provides the corresponding ethyl ester (35). Cyclisation with acetyl chloride in presence of a base such as $K_2CO_3$ in a solvent such as DMF provides 3-oxo-3,4-dihydro-2H-benzo[1,4]oxazine derivatives (36). Compounds of structure (36) can optionally be alkylated with alkylating reagents such as methyl iodide in presence of a base such as $K_2CO_3$. Saponification with a base such as NaOH in a solvent such as EtOH/water leads to the corresponding acids (37) or (38). Reduction of compounds of structure (36) with $NaBH_4$ in the presence of $BF_3$-diethyl etherate leads to the corresponding 3,4-dihydro-2H-benzo[1,4]oxazine derivative which can optionally be alkylated and/or saponified as described before to provide the corresponding acids (40) or (41) (Kuroita T. et al, *Chemical Pharmaceutical Bulletin* 1996, 44, 4, 756-764).

Scheme 9: Synthesis of carboxylic acids $R^2$—COOH which represent an 3,4-dihydro-2H-benzo[1,4] oxazinyl-carboxylic acid derivative

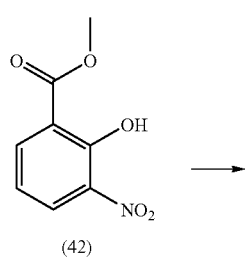

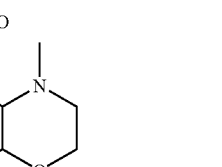

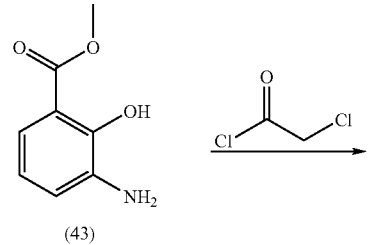

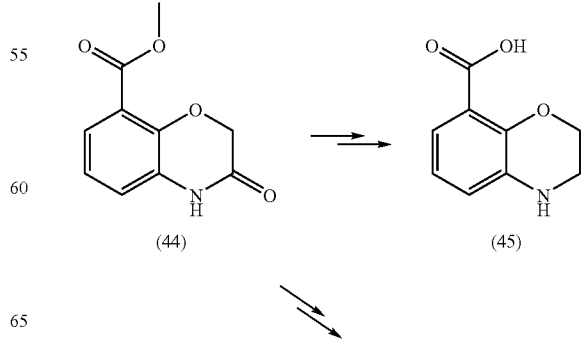

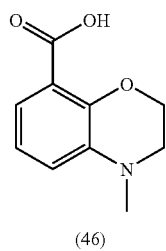

(46)

Hydrogenation of methyl 3-nitrosalicylate (42) in presence of a palladium catalyst provides the aniline derivative (43) which can be cyclized with chloroacetyl chloride as described before to the ester (44). Reduction of compounds of structure (44) with NaBH$_4$ in the presence of BF$_3$-diethyl etherate leads to the corresponding 3,4-dihydro-2H-benzo[1,4]oxazine derivative which can optionally be alkylated and/or saponified as described before to provide the corresponding acids (45) or (46) (Kuroita T. et al, *Chemical Pharmaceutical Bulletin* 1996, 44, 4, 756-764).

Carboxylic acid derivatives R$^2$—COOH which represent a chroman-carboxylic acid derivative can be synthesised according to scheme 10.

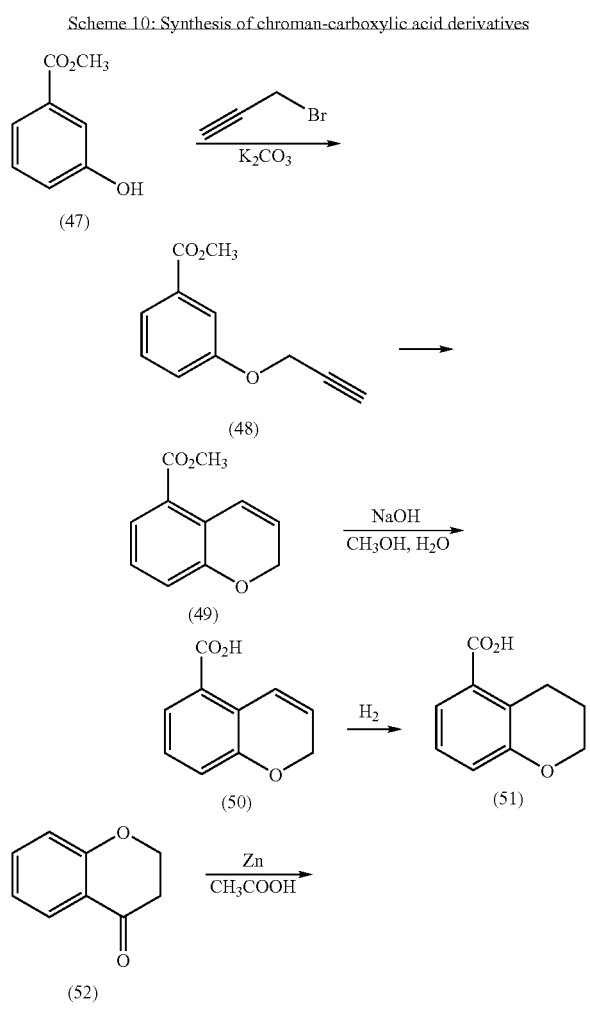

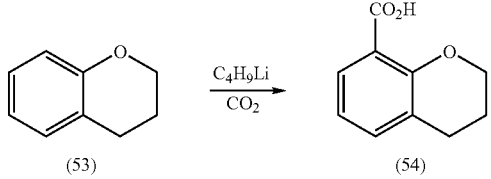

Commercially available 3-hydroxy-benzoic acid methyl ester (47) is alkylated with propargyl bromide in the presence of K$_2$CO$_3$ to give phenylether (48) which is cyclized to the chromen derivative (49) by heating to reflux in N,N-diethylaniline. The carboxylic ester is saponified by treatment of (49) with NaOH in MeOH/water and the obtained chromen derivative (50) is hydrogenated in presence of a palladium catalyst to give the desired acid (51). The corresponding chroman-8-carboxylic acid derivatives are synthesized by reduction of commercially available 4-chromanone (52) with zinc in acetic acid and subsequent ortho-metalation of the intermediate chroman derivative (53) with n-BuLi and trapping with carbon dioxide to give the desired acid (54).

Whenever the compounds of formula (I) are obtained in the form of mixtures of enantiomers, the enantiomers can be separated using methods known to the one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as NEt$_3$, diethylamine) and eluent B (hexane), at a flow rate of 0.8 to 150 mL/min.

EXPERIMENTAL SECTION

Abbrevations (As Used Herein):
aq. aqueous
anh. anhydrous
Boc tert.-butoxycarbonyl
Boc$_2$O di-tert.-butyl dicarbonate
BSA bovine serum albumine
CHO chinese hamster ovary
conc. concentrated
DBU 1,8-diazabicyclo[5.4.0]undec-7-ene
DCM dichloromethane
DIEA disopropylethylamine
DMF N,N-dimethylformamide
DMSO dimethylsulfoxide
EA ethyl acetate
eq equivalent(s)
ES electron spray
ether diethylether
EtOH ethanol
FC flash chromatography
FCS foatal calf serum
FLIPR fluorescent imaging plate reader
h hour(s)
HBSS Hank's balanced salt solution
HEPES 4-(2-hydroxyethyl)-piperazine-1-ethanesulfonic acid
HPLC high performance liquid chromatography
LC liquid chromatography
M molar(ity)
MeCN acetonitrile
MeOH methanol min minute(s)

MS mass spectroscopy org. organic prep. preparative

PyB OP (Benzotriazole-lyloxy)-tripyrrolidinophosphonium-hexafluorophosphate

RT room temperature sat. saturated sec. secundary $t_R$ retention time tert. tertiary TBTU O-benzotriazol-1-yl-N,N,N',N'-tetramethyluronium tetrafluoroborate TFA trifluoroacetic acid THF tetrahydrofuran I-Chemistry All temperatures are stated in ° C. Compounds are characterized by $^1$H-NMR (300 MHz: Varian Oxford or 400 MHz: Bruker Avance); chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, using two conditions: basic: eluent A: MeCN, eluent B: conc. NH$_3$ in water (1.0 mL/L), 5% to 95% CH$_3$CN; acidic: eluent A: MeCN, eluent B: TFA in water (0.4 mL/L), 5% to 95% CH$_3$CN), $t_R$ is given in min; by TLC (TLC-plates from Merck, Silica gel 60 F$_{254}$); or by melting point. Compounds are purified by column chromatography on silica gel or by preparative HPLC (column: X-terra RP18, 50×19 mm, 5 µm, gradient: 10-95% MeCN in water containing 0.5% of formic acid).

The following examples illustrate the preparation of pharmacologically active compounds of the invention but do not at all limit the scope thereof.

SYNTHESIS OF INTERMEDIATES

A.1. Synthesis of 2-methyl-thiazole-5-carboxylic acid Derivatives

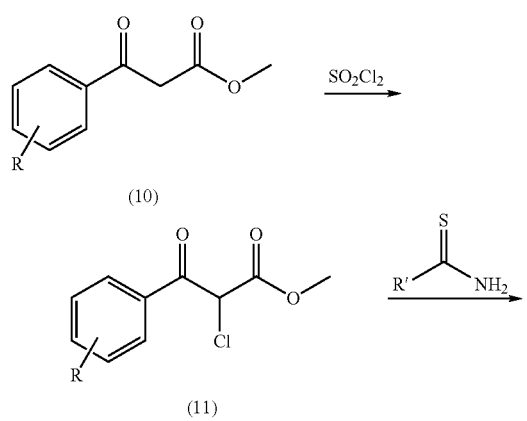

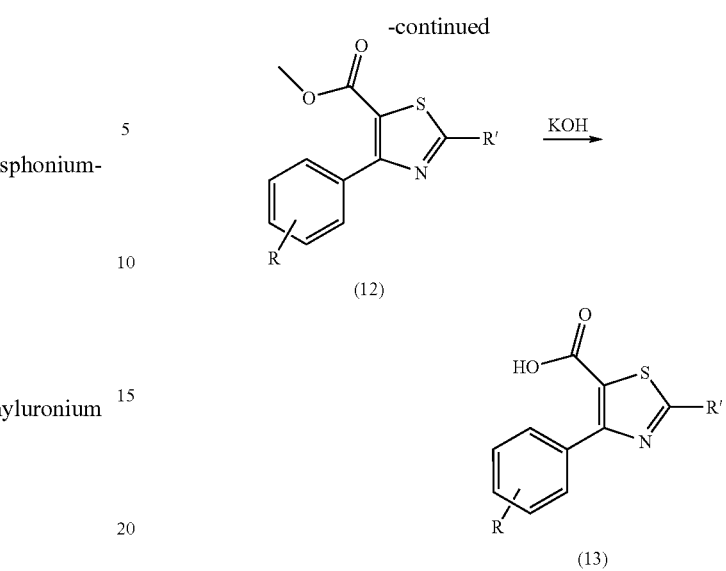

A.1.1 Synthesis of 2-methyl-4-p-tolyl-thiazole-5-carboxylic acid

A mixture of 4-methylbenzoyl acetate (5.52 mmol), sulfuryl chloride (5.52 mmol) in chloroform (3.3 ml) was held at reflux overnight. After cooling down to room temperature the organic phase was washed with water, dried over MgSO$_4$ and concentrated under reduced pressure. The crude product was dissolved in THF (12.0 ml) and thioacetamide (6.75 mmol) and solid NaHCO$_3$ (6.07 mmol) were added. The mixture was heated to reflux for 6 h and then it was filtered. The solvent was removed and the crude product purified by column chromatography using heptane/ethyl acetate as eluent system to provide 2-methyl-4-p-tolyl-thiazole-5-carboxylic acid methyl ester (2.67 mmol).

2-Methyl-4-p-tolyl-thiazole-5-carboxylic acid methyl ester (2.67 mmol) and solid KOH (5.35 mmol) were dissolved in ethanol (1.04 mL) and water (0.26 mL) and heated under reflux for 3 hours. After cooling, the solvent was evaporated under reduced pressure and ice water was added to the residue, followed by washing with hexane. The aqueous layer was acidified with 1N aq. HCl and the crystals thus precipitated were collected by filtration, washed with water and then dried to provide 2-methyl-4-p-tolyl-thiazole-5-carboxylic acid.

LC-MS: $t_R$=0.83 min; [M+H]$^+$=234.02.

A.1.2 Synthesis of 2-methyl-4-(4-methoxy-phenyl)-thiazole-5-carboxylic acid

This compound has been prepared in analogy of 2-methyl-4-p-tolyl-thiazole-5-carboxylic acid.

LC-MS: $t_R$=0.80 min; [M+H]$^+$=250.

A.1.3 Synthesis of 2-methyl-4-(4-chloro-phenyl)-thiazole-5-carboxylic acid

This compound has been prepared in analogy of 2-methyl-4-p-tolyl-thiazole-5-carboxylic acid.

LC-MS: $t_R$=0.86 min; [M+H]$^+$=252.

A.1.4 Synthesis of 2-methyl-4-(4-fluoro-phenyl)-thiazole-5-carboxylic acid

This compound has been prepared in analogy of 2-methyl-4-p-tolyl-thiazole-5-carboxylic acid.

LC-MS: $t_R$=0.81 min; [M+H]$^+$=238.

A.1.5 Synthesis of 2-methyl-4-(4-trifluoromethyl-phenyl)-thiazole-5-carboxylic acid This compound has been prepared in analogy of 2-methyl-4-p-tolyl-thiazole-5-carboxylic acid.
LC-MS: $t_R$=0.91 min; [M+H]$^+$=288.

A.1.6 Synthesis of 2-methyl-4-(3-methoxy-phenyl)-thiazole-5-carboxylic acid

This compound has been prepared in analogy of 2-methyl-4-p-tolyl-thiazole-5-carboxylic acid.
LC-MS: $t_R$=0.78 min; [M+H]$^+$=250.

A.1.7 Synthesis of 2-methyl-4-(3-chloro-phenyl)-thiazole-5-carboxylic acid

This compound has been prepared in analogy of 2-methyl-4-p-tolyl-thiazole-5-carboxylic acid.
LC-MS: $t_R$=0.85 min; [M+H]$^+$=253.

A.1.8 Synthesis of 2-methyl-4-(3-fluoro-phenyl)-thiazole-5-carboxylic acid

This compound has been prepared in analogy of 2-methyl-4-p-tolyl-thiazole-5-carboxylic acid.
LC-MS: $t_R$=0.80 min; [M+H]$^+$=238.

A.1.9 Synthesis of 2-methyl-4-m-tolyl-thiazole-5-carboxylic acid

This compound has been prepared in analogy of 2-methyl-4-p-tolyl-thiazole-5-carboxylic acid.
LC-MS: $t_R$=0.84 min; [M+H]$^+$=234

A.1.10 Synthesis of 2-methyl-4-(3-trifluoromethyl-phenyl)-thiazole-5-carboxylic acid This compound has been prepared in analogy of 2-methyl-4-p-tolyl-thiazole-5-carboxylic acid.
LC-MS: $t_R$=0.90 min; [M+H]$^+$=288.

A.2 Synthesis of 2-methyl-oxazole-4-carboxylic acid derivatives

A.2.1 Synthesis of 2-acetylamino-3-oxo-propionic acid methyl ester derivatives (General Procedure)

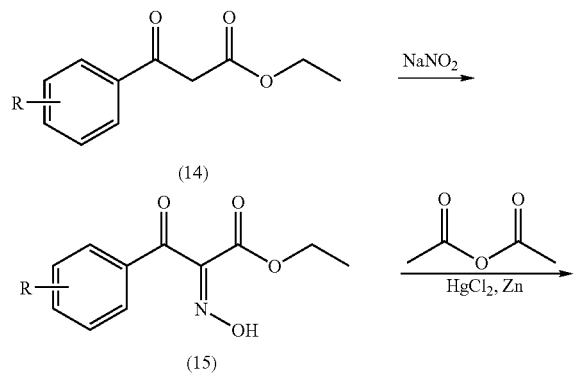

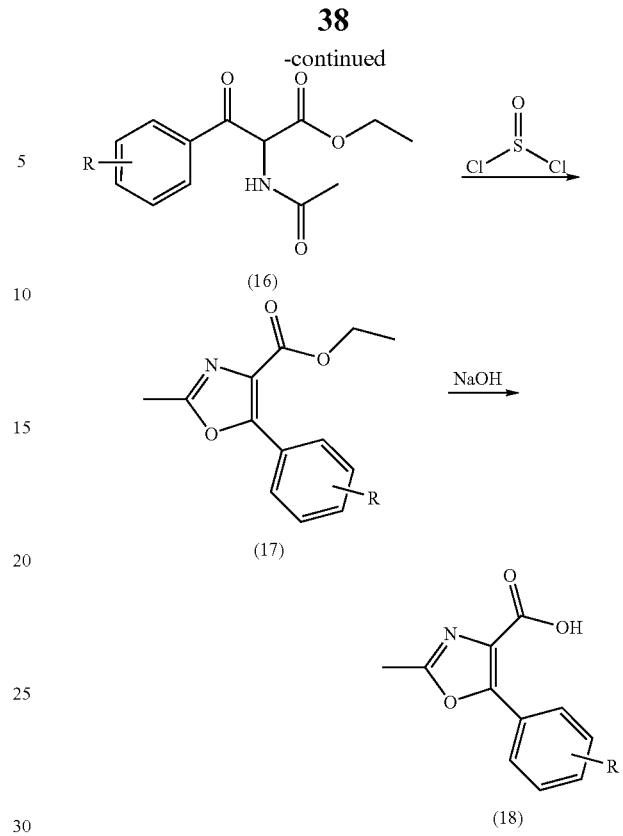

A solution of the respective 3-oxo-propionic acid methyl ester derivative (4.8 mmol, 1.0 eq.) in glacial acetic acid (1.9 mL) was cooled to 10° C. and at this temperature was added a solution of NaNO$_2$ (5.6 mmol, 1.16 eq.) in water (0.68 mL). After the addition was complete (15 min), the solution was allowed to warm to room temperature and stirred for 2 h. Then the solution was poured into water (10 mL) and after a few minutes crystals begun to appear. This suspension was cooled in an ice-bath and crystals were collected by filtration. The cake was washed several times with cold water and the water was removed by the azeotrope of toluene-water in vacuo to give 2-hydroxyimino-3-oxo-propionic acid methyl ester derivatives which were dissolved in a mixture of acetic anhydride (1.375 mL) and glacial acetic acid (1.8 mL). To this solution was added sodium acetate (0.296 mmol, 0.06 eq.) and HgCl$_2$ (0.01 mmol, 0.002 eq.). The mixture was refluxed for 1 h, then cooled to room temperature and filtered. The solid was rinsed with ether, the organic filtrate was recovered, washed 3 times with water and one time with 1M aq. K$_2$CO$_3$. The organic layer was dried over MgSO4, filtered and concentrated. The crude products were purified by flash chromatography to afford the corresponding 2-acetylamino-3-oxo-propionic acid methyl ester derivatives.

2-Acetylamino-3-oxo-3-(3-trifluoromethyl-phenyl)-propionic acid methyl ester prepared according to general procedure A.2.1 from 3-oxo-(3-trifluoromethyl-phenyl)-propionic acid methyl ester.
2-Acetylamino-3-oxo-3-m-tolyl-propionic acid methyl ester prepared according to general procedure A.2.1 from 3-oxo-3-m-tolyl-propionic acid methyl ester.
2-Acetylamino-3-oxo-3-p-tolyl-propionic acid methyl ester prepared according to general procedure A.2.1 from 3-oxo-3-p-tolyl-propionic acid methyl ester.

2-Acetylamino-3-(4-fluoro-phenyl)-3-oxo-propionic acid methyl ester
prepared according to general procedure A.2.1 from 3-oxo-3-(4-fluoro-phenyl)-propionic acid methyl ester.
2-Acetylamino-3-(4-methoxy-phenyl)-3-oxo-propionic acid methyl ester
prepared according to general procedure A.2.1 from 3-oxo-3-(4-methoxy-phenyl)-propionic acid methyl ester.

A.2.2 Synthesis of 2-methyl-oxazole-4-carboxylic acid Derivatives (General Procedure)

A solution of the respective 2-acetylamino-3-oxo-propionic acid methyl ester derivative (0.63 mmol, 1.0 eq.) in chloroform (0.4 mL) was cooled to 0° C. in an ice/NaCl bath. $SOCl_2$ (0.88 mmol, 1.4 eq.) was added to the stirred solution and the temperature was maintained at 0° C. for 30 minutes. Then the solution was stirred and refluxed for one hour. Another 0.25 eq. of $SOCl_2$ was added and the reaction mixture was refluxed for another hour.

The excess $SOCl_2$ was quenched with 1M aq. $K_2CO_3$. The aqueous layer was extracted twice with ether. The combined organic phases were washed once with water and dried over $MgSO_4$, filtered and concentrated yielding the corresponding 2-methyl-oxazole-4-carboxylic acid methyl ester derivative. The respective 2-methyl-oxazole-4-carboxylic acid methyl ester derivative was dissolved in a mixture of ethanol (0.7 ml) and 2N aq. NaOH (0.7 mL, 2.5 eq.). The mixture was stirred at RT for 2 hours.

The reaction mixture was washed once with ether and this organic layer was discarded. The aqueous layer was then acidified with conc. HCl and extracted twice with ether. Both organic layers were combined, dried over $MgSO_4$ and concentrated in vacuo to afford the corresponding 2-methyl-oxazole-4-carboxylic acid derivatives.
2-Methyl-5-m-tolyl-oxazole-4-carboxylic acid
prepared according to general procedure A.2.2 from 2-acetylamino-3-oxo-3-m-tolyl-propionic acid methyl ester.
LC-MS: $t_R$=0.51 min; [M–H]$^+$=216.33.
2-Methyl-5-(3-trifluoromethyl-phenyl)-oxazole-4-carboxylic acid
prepared according to general procedure A.2.2 from 2-acetylamino-3-oxo-3-(3-trifluoromethyl-phenyl)-propionic acid methyl ester.
LC-MS: $t_R$=0.55 min; [M–H]$^+$=270.24.
2-Methyl-5-p-tolyl-oxazole-4-carboxylic acid
prepared according to general procedure A.2.2 from 2-acetylamino-3-oxo-3-p-tolyl-propionic acid methyl ester.
LC-MS: $t_R$=0.55 min; [M–H]$^+$=216.34.
5-(4-Fluoro-phenyl)-2-methyl-oxazole-4-carboxylic acid
prepared according to general procedure A.2.2 from 2-acetylamino-3-(4-fluoro-phenyl)-3-oxo-propionic acid methyl ester.
LC-MS: $t_R$=0.49 min; [M–H]$^+$=220.30.
5-(4-Methoxy-phenyl)-2-methyl-oxazole-4-carboxylic acid
prepared according to general procedure A.2.2 from 2-acetylamino-3-(4-methoxy-phenyl)-3-oxo-propionic acid methyl ester.
LC-MS: $t_R$=0.77 min; [M+H]$^+$=234.31.
5-(3-Methoxy-phenyl)-2-methyl-oxazole-4-carboxylic acid
prepared according to general procedure A.2.2 from 2-acetylamino-3-(3-methoxy-phenyl)-3-oxo-propionic acid methyl ester.
LC-MS: $t_R$=0.49 min; [M+H]$^+$=232.30.

A.3. Synthesis of thiazole-4-carboxylic acid Derivatives

The synthesis of the required thiazole-4-carboxylic acid derivatives is described together with the corresponding examples below.

SYNTHESIS OF EXAMPLES

Example 1

(2RS)-Benzofuran-4-carboxylic acid [1-(biphenyl-2-carbonyl)-azetidin-2-ylmethyl]-amide a) Synthesis of (2RS)-[1-(biphenyl-2-carbonyl)-azetidin-2-ylmethyl]-carbamic acid tert-butyl ester To a mixture of 2-biphenylcarboxylic acid (107 mg), PyBOP (280 mg), DIEA (0.215 mL) in dry DMF (0.5 mL), was added a solution of 2-(N-Boc-aminomethyl)azetidine (100 mg) in dry DMF (0.5 mL). The resulting reaction mixture was stirred at RT for 20 h. The reaction mixture was diluted with EA, washed with water. The aqueous phase was extracted once again with EA, the combined organic extracts were dried ($MgSO_4$), filtered and concentrated to yield the crude product as light brown oil. FC (EA) gave 140 mg (71%) of the title compound as a light yellow oil.
LC-MS: rt=0.99 min, 367 [M+H]$^+$.

b) Synthesis of (2RS)-(2-aminomethyl-azetidin-1-yl)-biphenyl-2-yl-methanone

To a cold (5° C.) solution of (2RS)-[1-(biphenyl-2-carbonyl)-azetidin-2-ylmethyl]-carbamic acid tent-butyl ester (140 mg) in dry DCM (3.5 mL) was added dropwise TFA (0.15 mL). The reaction mixture was stirred at RT for 20 h.

The reaction mixture was diluted with DCM, basified with sat. $NaHCO_3$ solution. The aqueous phase was extracted with DCM, the combined organic extracts were dried ($MgSO_4$), filtered and concentrated to yield a crude light brown oil (100 mg, 98%) which was used for the next step without further purification.
LC-MS: rt=0.71 min, 267 [M+H]$^+$.

c) Synthesis of (2RS)-benzofuran-4-carboxylic acid [1-(biphenyl-2-carbonyl)-azetidin-2-ylmethyl]-amide To a mixture of benzofuran-4-carboxylic acid (Eissenstat M. A. et al, *J. Med. Chem.* 1995, 38, 16, 3094-3105 (61 mg), PyBOP (196 mg), DIEA (0.15 mL) in dry DMF (0.5 mL), was added a solution of (2RS)-(2-aminomethyl-azetidin-1-yl)-biphenyl-2-yl-methanone (100 mg) in dry DMF (0.5 mL). The resulting reaction mixture was stirred at RT for 20 h. The reaction mixture was diluted with EA, washed with water. The aqueous phase was extracted once again with EA, the combined organic extracts were dried ($MgSO_4$), filtered and concentrated to yield the crude product as light brown oil.

FC (EA) gave 140 mg (71%) of the title compound as a light yellow oil
LC-MS: rt=0.99 min, 411 [M+H]$^+$.

Example 2

(2RS)-Benzofuran-4-carboxylic acid [1-(biphenyl-2-sulfonyl)-azetidin-2-ylmethyl]-amide a) Synthesis of (2RS)-[1-(biphenyl-2-sulfonyl)-azetidin-2-ylmethyl]-carbamic acid tert-butyl ester To a cold (5° C.) solution of 2-(N-Boc-aminomethyl) azetidine (200 mg), DIEA (0.375 mL) in dry DMF (2 mL), was added portionwise biphenyl-2-sulfonyl chloride (272 mg). The reaction mixture was stirred at RT for 20 h. The reaction mixture was diluted with EA, washed with water. The organic extract was dried (MgSO$_4$), filtered and concentrated to yield the crude product as light brown oil (295 mg, 68%) which was used for the next step without further purification.

LC-MS: rt=1.05 min, 403 [M+H]$^+$.

b) Synthesis of (2RS)-[1-(biphenyl-2-sulfonyl)-azetidin-2-yl]-methylamine

To a cold (5° C.) solution of (2RS)-[1-(biphenyl-2-sulfonyl)-azetidin-2-ylmethyl]-carbamic acid tert-butyl ester (295 mg) in dry DCM (7.5 mL) was added dropwise TFA (0.281 mL). The reaction mixture was stirred at RT for 20 h. The reaction mixture was diluted with DCM, basified with sat. NaHCO$_3$ solution. The aqueous phase was extracted with DCM, the combined organic extracts were dried (MgSO$_4$), filtered and concentrated to yield the crude product as light brown oil (218 mg, 98%) which was used for the next step without further purification.

LC-MS: rt=0.72 min, 303 [M+H]$^+$.

c) Synthesis of (2RS)-benzofuran-4-carboxylic acid [1-(biphenyl-2-sulfonyl)-azetidin-2-ylmethyl]-amide To a mixture of benzofuran-4-carboxylic acid (Eissenstat M. A. et al, *J. Med. Chem.* 1995, 38, 16, 3094-3105 (63.3 mg), PyBOP (203 mg), DIEA (0.116 mL) in dry DMF (1.5 mL), was added a solution of (2RS)-[1-(biphenyl-2-sulfonyl)-azetidin-2-yl]-methylamine (118 mg) in dry DMF (0.5 mL). The resulting reaction mixture was stirred at RT for 20 h. The reaction mixture was diluted with EA, washed with water. The aqueous phase was extracted once again with EA, the combined organic extracts were dried (MgSO$_4$), filtered and concentrated to yield the crude product as light brown oil.

FC (EA) gave 118 mg (67%) of the title compound as a light yellow oil.

LC-MS: rt=1.04 min, 447 [M+H]$^+$.

Example 3

(2RS)-6-Methyl-imidazo[2,1-b]thiazole-5-carboxylic acid{1-[5-(4-fluoro-phenyl)-2-methyl-thiazole-4-carbonyl]-azetidin-2-ylmethyl}-amide a) Synthesis of 3-chloro-3-(4-fluoro-phenyl)-2-oxo-propionic acid methylester (General Procedure)

To a cold (−60° C.) stirred suspension of potassium-tert-butylate (27.77 g) in dry THF (300 mL) was added dropwise over 30 min. a solution of 4-fluorobenzaldehyde (31.03 g), methyl dichloroacetate (35.74 g) in dry THF (75 mL). The reaction mixture was stirred at −60° C. for 3 h and allowed to warm to RT overnight. The reaction mixture was then concentrated in vacuo and the residue was dissolved in DCM (300 mL) and washed with cold water. The aqueous phase was extracted twice with DCM (150 mL). The combined organic extracts were washed with cold water, dried (Na$_2$SO$_4$), filtered and concentrated to yield a crude oil. The crude product was distilled over a 40 cm Vigreux column to give 32.58 g (50%) of the title compound (bp=86° C./2.5× 10$^{-1}$ mbar).

$^1$H-NMR (CDCl$_3$): δ=3.84 (s, 3H); 6.16 (s, 1H); 7.08 (m, 2H); 7.41 (m, 2H).

b) Synthesis of 5-(4-fluoro-phenyl)-2-methyl-thiazole-4-carboxylic acid methyl ester (general procedure)

To a refluxing solution of thioacetamide (9.02 g) in dry MeOH (200 mL) was added dropwise over 10 min. a solution of 3-chloro-3-(4-fluoro-phenyl)-2-oxo-propionic acid methylester (31.30 g) in dry MeOH (50 mL). The reaction mixture was stirred at reflux for 1 h. After cooling to RT, the reaction mixture was concentrated in vacuo and the residue was diluted with DCM (500 mL) and EA (150 mL). The solution was washed with cold water (100 mL), sat. NaHCO$_3$ solution (100 mL). The organic phase was washed again with sat. NaHCO$_3$ solution (100 mL), water (2×50 mL), dried (Na$_2$SO$_4$), filtered and concentrated to yield a crude oil.

FC (EA/petroleum ether: 30/75 to 1/2) gave 17.71 g (58%) of the title compound.

$^1$H-NMR (CDCl$_3$): δ=2.75 (s, 3H); 3.84 (s, 3H); 7.10 (m, 2H); 7.47 (m, 2H).

c) Synthesis of 5-(4-fluoro-phenyl)-2-methyl-thiazole-4-carboxylic acid (General Procedure)

To a solution of 5-(4-fluoro-phenyl)-2-methyl-thiazole-4-carboxylic acid methyl ester (15 g) in a mixture of THF (60 mL) and MeOH (20 mL) was added a solution of sodium hydroxide (2.63 g) in water (60 mL). The reaction mixture was stirred at RT for 30 min. The reaction mixture was then concentrated in vacuo, and the residue was dissolved with water (100 mL) and concentrated again in vacuo. The residue was dissolved in water (250 mL), cooled to 0° C. with a ice-bath. Then was added a solution of conc.HCl (37%)(7.72 g) in water (7.72 g) and stirred at 0° C. for 15 min. The resulting precipitate was filtered off, washed with water and dried in high vacuum pump. to give the title compound as a white solid (13.16 g, 93%).

$^1$H-NMR (DMSO-d$_6$): δ=2.67 (s, 3H); 7.27 (m, 2H); 7.53 (m, 2H); 12.89 (br.s, 1H).

d) Synthesis of (2RS)-{1-[5-(4-fluoro-phenyl)-2-methyl-thiazole-4-carbonyl]-azetidin-2-ylmethyl}carbamic acid tent-butyl ester This compound was synthesised as (2RS)-[1-(biphenyl-2-carbonyl)-azetidin-2-ylmethyl]-carbamic acid tert-butyl ester but using 5-(4-fluoro-phenyl)-2-methyl-thiazole-4-carboxylic acid instead biphenyl-2-carboxylic acid.

LC-MS: rt=0.95 min, 406 [M+H]$^+$.

e) Synthesis of (2RS)-(2-aminomethyl-azetidin-1-yl)-[5-(4-fluoro-phenyl)-2-methyl-thiazol-4-yl]-methanone This compound was synthesised as (2RS)-(2-aminomethyl-azetidin-1-yl)-biphenyl-2-yl-methanone.

LC-MS: rt=0.70 min, 306 [M+H]$^+$.

f) Synthesis of (2RS)-6-methyl-imidazo[2,1-b]thiazole-5-carboxylic acid {1-[5-(4-fluoro-phenyl)-2-methyl-thiazole-4-carbonyl]-azetidin-2-ylmethyl}-amide To a mixture of 6-methylimidazo[2,1-b][1,3]thiazole-5-carboxylic acid (Acros Organics) (15 mg), PyBOP (42.7 mg), DIEA (0.035 mL) in dry DMF (0.15 mL), was added a solution of (2RS)-(2-aminomethyl-azetidin-1-yl)-[5-(4-fluorophenyl)-2-methyl-thiazol-4-yl]-methanone (25 mg) in dry DMF (0.1 mL). The resulting reaction mixture was stirred at RT for 20 h. The reaction mixture was diluted with EA, washed with water. The aqueous phase was extracted once again with EA, the combined organic extracts were dried ($MgSO_4$), filtered and concentrated to yield a crude light brown oil.

FC (EA to DCM/MeOH: 9/1) gave 22 mg (57%) of the title compound as a light brown solid.

LC-MS: rt=0.81 min, 470 $[M+H]^+$.

Example 4

(2RS)-Benzofuran-4-carboxylic acid {1-[5-(4-fluoro-phenyl)-2-methyl-thiazole-4-carbonyl]-azetidin-2-ylmethyl}-amide To a mixture of benzofuran-4-carboxylic acid (11 mg), PyBOP (35 mg), DIEA (0.030 mL) in dry DMF (0.15 mL), was added a solution of (2RS)-(2-aminomethyl-azetidin-1-yl)$_{45}$-(4-fluoro-phenyl)-2-methyl-thiazol-4-A-methanone (20 mg) in dry DMF (0.1 mL). The resulting reaction mixture was stirred at RT for 20 h. The reaction mixture was diluted with EA, washed with water. The aqueous phase was extracted once again with EA, the combined organic extracts were dried ($MgSO_4$), filtered and concentrated to yield a crude light brown oil.

FC (EA to DCM/MeOH: 98/2) gave 23 mg (78%) of the title compound as a white solid.

LC-MS: rt=0.94 min, 450 $[M+H]^+$.

Example 5

(2RS)-6-Methyl-imidazo[2,1-b]thiazole-5-carboxylic acid [1-(2-methyl-5-p-tolyl-thiazole-4-carbonyl)-azetidin-2-ylmethyl]-amide a) Synthesis of 3-chloro-2-oxo-3-p-tolyl-propionic acid methylester This compound was synthesised as 3-chloro-3-(4-fluorophenyl)-2-oxo-propionic acid methyl ester but using 4-methylbenzaldehyde instead 4-fluorobenzaldehyde. $^1$H-NMR ($CDCl_3$): δ=2.35 (s, 3H); 3.83 (s, 3H); 6.13 (s, 1H); 7.21 (d, 2H); 7.28 (d, 2H).

b) Synthesis of 2-methyl-5-p-tolyl-thiazole-4-carboxylic acid methyl ester

This compound was synthesised as 5-(4-fluoro-phenyl)-2-methyl-thiazole-4-carboxylic acid methyl ester.

$^1$H-NMR ($CDCl_3$): δ=2.40 (s, 3H); 3.07 (s, 3H); 3.91 (s, 3H); 7.27 (d, 2H); 7.39 (d, 2H).

c) Synthesis of 2-methyl-5-p-tolyl-thiazole-4-carboxylic acid

This compound was synthesised as 5-(4-fluoro-phenyl)-2-methyl-thiazole-4-carboxylic acid.

$^1$H-NMR (DMSO-$d_6$): δ=2.32 (s, 3H); 2.64 (s, 3H); 7.22 (d, 2H); 7.33 (d, 2H).

d) Synthesis of (2RS)-[1-(2-methyl-5-p-tolyl-thiazole-4-carbonyl]-azetidin-2-ylmethyl]-carbamic acid tert-butyl ester This compound was synthesised as (2RS)-[1-(biphenyl-2-carbonyl)-azetidin-2-ylmethyl]-carbamic acid tert-butyl ester but using 2-methyl-5-p-tolyl-thiazole-4-carboxylic acid instead biphenyl-2-carboxylic acid.

LC-MS: rt=0.99 min, 402 $[M+H]^+$.

e) Synthesis of (2RS)-(2-aminomethyl-azetidin-1-yl)-(2-methyl-5-p-tolyl-thiazol-4-yl]-methanone This compound was synthesised as (2RS)-(2-aminomethyl-azetidin-1-yl)-[5-(4-fluoro-phenyl)-2-methyl-thiazol-4-yl]-methanone.

LC-MS: rt=0.71 min, 302 $[M+H]^+$.

f) Synthesis of (2RS)-6-methyl-imidazo[2,1-b]thiazole-5-carboxylic acid [1-(2-methyl-5-p-tolyl-thiazole-4-carbonyl)-azetidin-2-ylmethyl]-amide To a mixture of 6-methylimidazo[2,1-b][1,3]thiazole-5-carboxylic acid (12 mg), PyBOP (34.5 mg), DIEA (0.030 mL) in dry DMF (0.15 mL), was added a solution of (2RS)-(2-aminomethyl-azetidin-1-yl)-(2-methyl-5-p-tolyl-thiazol-4-yl]-methanone (20 mg) in dry DMF (0.1 mL). The resulting reaction mixture was stirred at RT for 20 h. The reaction mixture was diluted with EA, washed with water. The aqueous phase was extracted once again with EA, the combined organic extracts were dried ($MgSO_4$), filtered and concentrated to yield a crude light brown oil.

FC (EA to DCM/MeOH: 9/1) gave 21 mg (67%) of the title compound as a light brown solid.

LC-MS: rt=0.84 min, 466 $[M+H]^+$.

Synthesis of (2S)-benzofuran-4-carboxylic acid-(azetidine-2-ylmethyl)-amide hydrochloride as intermediate a) Synthesis of (2S)-carbamoyl-azetidine-1-carboxylic acid tert-butyl ester A mixture of 1-Boc-L-azetidine-2-carboxylic acid (10 g), conc. $H_2SO_4$ (1 mL) in dry MeOH (200 mL) was stirred at RT for 2 h. The reaction mixture was then concentrated in vacuo, the residue was diluted with EA, basified with sat. $NaHCO_3$ solution. The organic extract was washed with water, dried ($MgSO_4$), filtered and concentrated to yield the crude methyl ester as a yellow oil (11 g, 102%). This crude ester was dissolved in dry MeOH (200 mL) and treated with 7M ammonia solution in MeOH (100 mL). The resulting white suspension was stirred at RT for 72 h and filtered off. The filtrate was concentrated in vacuo to give the title compound as a white solid (8.5 g, 92%).

$^1$H-NMR ($CDCl_3$): δ=1.44 (s, 9H); 2.46 (m, 2H); 3.88 (m, 2H); 4.63 (m, 1H).

b) Synthesis of (2S)-aminomethyl-azetidine-1-carboxylic acid tert-butyl ester

To a cold (0° C.) solution of (2S)-carbamoyl-azetidine-1-carboxylic acid tert-butyl ester (8 g) in dry THF (200 mL) was added dropwise 1M BH₃ solution in THF (160 mL). The reaction mixture was stirred at RT under nitrogen for 20 h and cooled to 0° C. Then was added carefully 1M HCl solution (200 mL) and brine and the mixture was extracted with EA (3×). The aqueous phase was basified with 2M NaOH solution (pH 10), extracted with EA (3×). The combined organic extracts were washed with brine, dried (Na₂SO₄), filtered and concentrated to yield the title compound light yellow oil (1.9 g, 25%).

$^1$H-NMR (CDCl₃): δ=1.42 (s, 9H); 1.93-2.17 (m, 2H); 2.91 (m, 2H); 3.80 (m, 2H); 4.21 (m, 1H).

c) Synthesis of (2S)-{[(benzofuran-4-carbonyl)-amino]-methyl}-azetidine-1-carboxylic acid tent-butyl ester To a solution of benzofuran-4-carboxylic acid (548.5 mg), TBTU (1.41 g) DIEA (1.73 mL) in dry DMF (6 mL) was added dropwise a solution of (2S)-aminomethyl-azetidine-1-carboxylic acid tert-butyl ester (630 mg) in dry DMF (2 mL). The reaction mixture was stirred under nitrogen for 72 h. The reaction mixture was diluted with EA, washed with water, the aqueous phase was extracted twice again with EA. The combined organic extracts were washed with brine, dried (Na₂SO₄), filtered and concentrated to yield a crude oil.

FC (EA/n-heptane: 1/1) gave 336 mg (30%) of the title compound as a white solid.

LC-MS: rt=0.95 min, 331 [M+H]⁺.

d) Synthesis of (2S)-benzofuran-4-carboxylic acid-(azetidine-2-ylmethyl)-amide hydrochloride To a solution of (2S)-{[(benzofuran-4-carbonyl)-amino]-methyl}-azetidine-1-carboxylic acid tert-butyl ester (170 mg) in 2-propanol (4 mL) was added 5-6M HCl in 2-propanol (2 mL). The resulting reaction mixture was stirred at RT under nitrogen for 20 h and concentrated in vacuo to yield 120 mg (85%) of the title compound as an oil.

LC-MS: rt=0.95 min, 331 [M+H]⁺.

Example 6

(2S)-Benzofuran-4-carboxylic acid [1-(biphenyl-2-carbonyl)-azetidine-2-ylmethyl]-amide A mixture of biphenyl-2-carboxylic acid (8.5 mg), TBTU (21 mg), DIEA (0.015 mL), (2S)-benzofuran-4-carboxylic acid-(azetidine-2-ylmethyl)-amide hydrochloride (10 mg) in dry DMF (0.1 mL) was stirred at RT for 20 h under nitrogen. The reaction mixture was diluted with EA, washed with water, the aqueous phase was extracted twice again with EA. The combined organic extracts were washed with brine, dried (Na₂SO₄), filtered and concentrated to yield a crude oil.

FC (EA/n-heptane: 1/1) gave 14 mg (82%) of the title compound as a white solid.

LC-MS: rt=0.98 min, 411 [M+H]⁺.

Example 7

(2S)-Benzofuran-4-carboxylic acid [1-(2-trifluoromethoxy-benzenesulfonyl)-azetidin-2-ylmethyl]-amide To a cold (5° C.) solution of (2S)-benzofuran-4-carboxylic acid-(azetidine-2-ylmethyl)-amide hydrochloride (10 mg), DIEA (0.015 mL) in dry DMF (0.1 mL), was added portionwise 2-trifluoromethoxybenzene sulfonyl chloride (11.2 mg).

The reaction mixture was stirred at RT for 20 h. The reaction mixture was diluted with EA, washed with water. The organic extract was dried (MgSO₄), filtered and concentrated to yield a crude oil.

FC (EA/n-heptane: 1/1) gave 9 mg (46%) of the title compound as a solid.

LC-MS: rt=0.87 min, 455 [M+H]⁺.

Example 8

(2S)-Benzofuran-4-carboxylic acid [1-(biphenyl-2-sulfonyl)-azetidin-2-ylmethyl]-amide To a cold (5° C.) solution of (2S)-benzofuran-4-carboxylic acid-(azetidine-2-ylmethyl)-amide hydrochloride (10 mg), DIEA (0.015 mL) in dry DMF (0.1 mL), was added portionwise biphenyl-2-sulfonyl chloride (10.9 mg). The reaction mixture was stirred at RT for 20 h. The reaction mixture was diluted with EA, washed with water. The organic extract was dried (MgSO₄), filtered and concentrated to yield a crude oil.

FC (EA/n-heptane: 1/1) gave 8 mg (42%) of the title compound as a solid.

LC-MS: rt=1.03 min, 447 [M+H]⁺.

Example 9

(2S)-benzofuran-4-carboxylic acid [1-(2-methoxy-benzoyl)-azetidin-2-ylmethyl]-amide To a cold (5° C.) solution of (2S)-benzofuran-4-carboxylic acid-(azetidine-2-ylmethyl)-amide hydrochloride (10 mg), DIEA (0.015 mL) in dry DMF (0.1 mL), was added portionwise 2-methoxy-benzoyl chloride (7.35 mg). The reaction mixture was stirred at RT for 20 h. The reaction mixture was diluted with EA, washed with water. The organic extract was dried (MgSO₄), filtered and concentrated to yield a crude oil.

FC (EA/n-heptane: 1/1) gave 7.3 mg (46%) of the title compound as a solid. LC-MS: rt=0.76 min, 365 [M+H]⁺.

Example 10

(2RS)-6-Methyl-imidazo[2,1-b]thiazole-5-carboxylic acid [1-(2-methyl-5-m-tolyl-thiazole-4-carbonyl)-azetidin-2-ylmethyl]-amide a) Synthesis of 3-chloro-2-oxo-3-m-tolyl-propionic acid methylester This compound was synthesised as 3-chloro-3-(4-fluorophenyl)-2-oxo-propionic acid methylester but using 3-methylbenzaldehyde instead 4-fluorobenzaldehyde.

$^1$H-NMR (CDCl₃): δ=2.36 (s, 3H); 3.83 (s, 3H); 6.12 (s, 1H); 7.21 (m, 4H).

b) Synthesis of 2-methyl-5-m-tolyl-thiazole-4-carboxylic acid methyl ester

This compound was synthesised as 5-(4-fluoro-phenyl)-2-methyl-thiazole-4-carboxylic acid methyl ester.

$^1$H-NMR (CDCl₃): δ=2.40 (s, 3H); 2.96 (s, 3H); 3.90 (s, 3H); 7.32 (m, 4H).

c) Synthesis of 2-methyl-5-m-tolyl-thiazole-4-carboxylic acid

This compound was synthesised as 5-(4-fluoro-phenyl)-2-methyl-thiazole-4-carboxylic acid.

$^1$H-NMR (DMSO-d₆): δ=2.31 (s, 3H); 2.64 (s, 3H); 7.25 (m, 4H).

d) Synthesis of (2RS)-[1-(2-methyl-5-m-tolyl-thiazole-4-carbonyl]-azetidin-2-ylmethyl]-carbamic acid tent-butyl ester This compound was synthesised as (2RS)-[1-(biphenyl-2-carbonyl)-azetidin-2-ylmethyl]-carbamic acid tert-butyl ester but using 2-methyl-5-m-tolyl-thiazole-4-carboxylic acid
instead biphenyl-2-carboxylic acid.
LC-MS: rt=0.99 min, 402 [M+H]$^+$.

e) Synthesis of (2RS)-(2-aminomethyl-azetidin-1-yl)-(2-methyl-5-m-tolyl-thiazol-4-A-methanone This compound was synthesised as (2RS)-(2-aminomethyl-azetidin-1-yl)-[5-(4-fluoro-phenyl)-2-methyl-thiazol-4-yl]-methanone.
LC-MS: rt=0.72 min, 302 [M+H]$^+$.

f) Synthesis of (2RS)-6-methyl-imidazo[2,1-b]thiazole-5-carboxylic acid [1-(2-methyl-5-m-tolyl-thiazole-4-carbonyl)-azetidin-2-ylmethyl]-amide This compound was synthesized as example 5.
LC-MS: rt=0.84 min, 466 [M+H]$^+$.

Example 11

(2RS)-6-Methyl-imidazo[2,1-b]thiazole-5-carboxylic acid{1-[5-(3-fluoro-phenyl)-2-methyl-thiazole-4-carbonyl]-azetidin-2-ylmethyl}-amide a) Synthesis of 3-chloro-3-(3-fluoro-phenyl)-2-oxo-propionic acid methylester This compound was synthesised as 3-chloro-3-(4-fluoro-phenyl)-2-oxo-propionic acid methylester but using 3-fluorobenzaldehyde instead 4-fluorobenzaldehyde.
$^1$H-NMR (CDCl$_3$): δ=3.95 (s, 3H); 4.44 (s, 1H); 7.13-7.40 (m, 4H).

b) Synthesis of 5-(3-fluoro-phenyl)-2-methyl-thiazole-4-carboxylic acid methyl ester This compound was synthesised as 5-(4-fluoro-phenyl)-2-methyl-thiazole-4-carboxylic acid methyl ester.
$^1$H-NMR (CDCl$_3$): δ=2.67 (s, 3H); 3.68 (s, 3H); 7.25-7.50 (m, 4H).

c) Synthesis of 5-(3-fluoro-phenyl)-2-methyl-thiazole-4-carboxylic acid

This compound was synthesised as 5-(4-fluoro-phenyl)-2-methyl-thiazole-4-carboxylic acid.
$^1$H-NMR (DMSO-d$_6$): δ=2.69 (s, 3H); 7.30-7.59 (m, 4H).

d) Synthesis of (2RS)-{1-[5-(3-fluoro-phenyl)-2-methyl-thiazole-4-carbonyl]-azetidin-2-ylmethyl}-carbamic acid tent-butyl ester This compound was synthesised as (2RS)-[1-(biphenyl-2-carbonyl)-azetidin-2-ylmethyl]-carbamic acid tert-butyl ester but using 5-(3-fluoro-phenyl)-2-methyl-thiazole-4-carboxylic acid instead biphenyl-2-carboxylic acid.
LC-MS: rt=0.97 min, 406 [M+H]$^+$.

e) Synthesis of (2RS)-(2-aminomethyl-azetidin-1-yl)-[5-(3-fluoro-phenyl)-2-methyl-thiazol-4-yl]-methanone This compound was synthesised as (2RS)-(2-aminomethyl-azetidin-1-yl)-[5-(4-fluoro-phenyl)-2-methyl-thiazol-4-yl]-methanone.
LC-MS: rt=0.69 min, 306 [M+H]$^+$.

f) (2RS)-6-Methyl-imidazo[2,1-b]thiazole-5-carboxylic acid{1-[5-(3-fluoro-phenyl)-2-methyl-thiazole-4-carbonyl]-azetidin-2-ylmethyl}-amide This compound was synthesized as example 5.
LC-MS: rt=0.83 min, 470 [M+H]$^+$.

Example 12

(2RS)-6-Methyl-imidazo[2,1-b]thiazole-5-carboxylic acid {1-[2-methyl-5-(4-trifluoromethyl-phenyl)-thiazole-4-carbonyl]-azetidin-2-ylmethyl}-amide a) Synthesis of 3-chloro-2-oxo-3-(4-trifluoromethyl-phenyl)-propionic acid methylester This compound was synthesised as 3-chloro-3-(4-fluoro-phenyl)-2-oxo-propionic acid methylester but using 4-trifluoromethylbenzaldehyde instead 4-fluorobenzaldehyde.
$^1$H-NMR (CDCl$_3$): δ=3.93 (s, 3H); 4.55 (s, 1H); 7.52 (d, 2H); 7.66 (d, 2H).

b) Synthesis of 2-methyl-5-(4-trifluoromethyl-phenyl)-thiazole-4-carboxylic acid methyl ester This compound was synthesised as 5-(4-fluoro-phenyl)-2-methyl-thiazole-4-carboxylic acid methyl ester. $^1$H-NMR (CDCl$_3$): δ=2.93 (s, 3H); 3.88 (s, 3H); 7.64 (d, 2H); 7.66 (d, 2H).

c) Synthesis of 2-methyl-5-(4-trifluoromethyl-phenyl)-thiazole-4-carboxylic acid This compound was synthesised as 5-(4-fluoro-phenyl)-2-methyl-thiazole-4-carboxylic acid.
$^1$H-NMR (DMSO-d$_6$): δ=2.68 (s, 3H); 7.76 (d, 2H); 7.80 (d, 2H).

d) Synthesis of (2RS)-{1-[2-methyl-5-(4-trifluoromethyl-phenyl)-thiazole-4-carbonyl]-azetidin-2-ylmethyl}-carbamic acid tent-butyl ester This compound was synthesised as (2RS)-[1-(biphenyl-2-carbonyl)-azetidin-2-ylmethyl]-carbamic acid tert-butyl ester but using 2-methyl-5-(4-trifluoromethyl-phenyl)-thiazole-4-carboxylic acid instead biphenyl-2-carboxylic acid.
LC-MS: rt=1.03 min, 456 [M+H]$^+$.

e) Synthesis of (2RS)-(2-aminomethyl-azetidin-1-yl)-[2-methyl-5-(4-trifluoromethyl-phenyl)-thiazol-4-yl]-methanone This compound was synthesised as (2RS)-(2-aminomethyl-azetidin-1-yl)-[5-(4-fluoro-phenyl)-2-methyl-thiazol-4-yl]-methanone.
LC-MS: rt=0.77 min, 356 [M+H]$^+$.

f) Synthesis of (2RS)-6-methyl-imidazo[2,1-b]thiazole-5-carboxylic acid{1-[5-(4-trifluoromethyl-phenyl)-2-methyl-thiazole-4-carbonyl]-azetidin-2-ylmethyl}-amide This compound was synthesized as example 5.
LC-MS: rt=0.90 min, 520 [M+H]+.

Example 13

(2RS)-6-Methyl-imidazo[2,1-b]thiazole-5-carboxylic acid{1-[5-(4-ethyl-phenyl)-2-methyl-thiazole-4-carbonyl]-azetidin-2-ylmethyl}-amide a) Synthesis of 3-chloro-3-(4-ethyl-phenyl)-2-oxo-propionic acid methylester This compound was synthesised as 3-chloro-3-(4-fluoro-phenyl)-2-oxo-propionic acid methylester but using 4-ethyl-benzaldehyde instead 4-fluorobenzaldehyde.
$^1$H-NMR (CDCl$_3$): δ=1.23 (t, 3H); 2.63 (q, 2H); 3.83 (s, 3H); 6.14 (s, 1H); 7.26 (d, 2H); 7.30 (d, 2H).

b) Synthesis of 5-(4-ethyl-phenyl)-2-methyl-thiazole-4-carboxylic acid methyl ester This compound was synthesised as 5-(4-fluoro-phenyl)-2-methyl-thiazole-4-carboxylic acid methyl ester.
$^1$H-NMR (CDCl$_3$): δ=1.27 (t, 3H); 2.69 (q, 2H); 2.89 (s, 3H); 3.89 (s, 3H); 7.26 (d, 2H); 7.41 (d, 2H).

c) Synthesis of 5-(4-ethyl-phenyl)-2-methyl-thiazole-4-carboxylic acid

This compound was synthesised as 5-(4-fluoro-phenyl)-2-methyl-thiazole-4-carboxylic acid.
$^1$H-NMR (DMSO-d$_6$): δ=1.18 (t, 3H); 2.48 (q, 2H); 2.64 (s, 3H); 7.25 (d, 2H); 7.35 (d, 2H).

d) Synthesis of (2RS)-{1-[5-(4-ethyl-phenyl)-2-methyl-thiazole-4-carbonyl]-azetidin-2-ylmethyl}-carbamic acid tent-butyl ester This compound was synthesised as (2RS)-[1-(biphenyl-2-carbonyl)-azetidin-2-ylmethyl]-carbamic acid tert-butyl ester but using 5-(4-ethyl-phenyl)-2-methyl-thiazole-4-carboxylic acid instead biphenyl-2-carboxylic acid.
LC-MS: rt=1.03 min, 416 [M+H]+.

e) Synthesis of (2RS)-(2-aminomethyl-azetidin-1-yl)-[5-(4-ethyl-phenyl)-2-methyl-thiazol-4-yl]-methanone This compound was synthesised as (2RS)-(2-aminomethyl-azetidin-1-yl)-[5-(4-fluoro-phenyl)-2-methyl-thiazol-4-yl]-methanone.
LC-MS: rt=0.75 min, 316 [M+H]+.

f) Synthesis of (2RS)-6-methyl-imidazo[2,1-b]thiazole-5-carboxylic acid{1-[5-(4-ethyl-phenyl)-2-methyl-thiazole-4-carbonyl]-azetidin-2-ylmethyl}-amide This compound was synthesized as example 5.
LC-MS: rt=0.88 min, 480 [M+H]+.

Example 14

(2S)-Benzofuran-4-carboxylic acid [1-(3-trifluoromethyl-benzoyl)-azetidin-2-ylmethyl]-amide This compound has been prepared as Example 6 but using commercially available 3-trifluoromethylbenzoic acid.
LC-MS: rt=0.83 min, 403 [M+H]+.

Example 15

(2S)-Benzofuran-4-carboxylic acid [1-(3',4'-dimethyl-biphenyl-2-carbonyl)-azetidin-2-ylmethyl]-amide This compound has been prepared as Example 6 but using commercially available 3',4'-dimethyl-biphenyl-2-carboxylic acid.
LC-MS: rt=0.89 min, 439 [M+H]+.

Example 16

(2S)-Benzofuran-4-carboxylic acid{1-[5-(4-fluoro-phenyl)-2-methyl-thiazole-4-carbonyl]-azetidin-2-ylmethyl}-amide This compound has been prepared as Example 6 but using 5-(4-fluoro-phenyl)-2-methyl-thiazole-4-carboxylic acid.
LC-MS: rt=0.85 min, 450 [M+H]+.

Example 17

(2S)-6-Methyl-imidazo[2,1-b]thiazole-5-carboxylic acid{1-[5-(3,4-dimethyl-phenyl)-2-methyl-thiazole-4-carbonyl]-azetidin-2-ylmethyl}-amide a) Synthesis of 3-chloro-3-(3,4-dimethyl-phenyl)-2-oxo-3-m-tolyl-propionic acid methyl ester This compound was synthesised as 3-chloro-3-(4-fluoro-phenyl)-2-oxo-propionic acid methyl ester but using 3,4-dimethylbenzaldehyde instead 4-fluorobenzaldehyde.

b) Synthesis of 5-(3,4-dimethyl-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.96 min, 262 [M+H]+.

c) Synthesis of 5-(3,4-dimethyl-phenyl)-2-methyl-thiazole-4-carboxylic acid

This compound was synthesised as 5-(4-fluoro-phenyl)-2-methyl-thiazole-4-carboxylic acid.
LC-MS: rt=0.86 min, 248 [M+H]+.

d) Synthesis of (2S)-2-{[(6-methyl-imidazo[2,1-b]thiazole-5-carbonyl)-amino]-methyl}-azetidine-1-carboxylic acid tent-butyl ester This compound has been prepared as in Example 6 but reaction of (2S)-aminomethyl-azetidine-1-carboxylic acid tert-butyl ester with commercially available 6-methyl-imidazo[2,1-b]thiazole-5-carboxylic acid.
LC-MS: rt=0.79 min, 351 [M+H]+.

e) Synthesis of (2S)-6-methyl-imidazo[2,1-b]thiazole-5-carbonylic acid(azetidin-2-ylmethyl)-amide hydrochloride This compound has been prepared as in Example 6. LC-MS: rt=0.40 min, 251 [M+H]$^+$.

f) Synthesis of (2S)-6-methyl-imidazo[2,1-b]thiazole-5-carboxylic acid{1-[5-(3,4-dimethyl-phenyl)-2-methyl-thiazole-4-carbonyl]-azetidin-2-ylmethyl}-amide This compound has been prepared as in Example 6 but using (2S)-6-methyl-imidazo[2,1-b]thiazole-5-carbonylic acid(azetidin-2-ylmethyl)-amide hydrochloride and 5-(3,4-dimethyl-phenyl)-2-methyl-thiazole-4-carboxylic acid.
LC-MS: rt=0.88 min, 480 [M+H]$^+$.

Example 18

(2S)-6-Methyl-imidazo[2,1-b]thiazole-5-carboxylic acid [1-(2-methyl-5-m-tolyl-thiazole-4-carbonyl)-azetidin-2-ylmethyl]-amide This compound has been prepared as in Example 6 but using (2S)-6-methyl-imidazo[2,1-b]thiazole-5-carbonylic acid(azetidin-2-ylmethyl)-amide hydrochloride and 2-methyl-5-m-tolyl-thiazole-4-carboxylic acid.
LC-MS: rt=0.88 min, 480 [M+H]$^+$.

Example 19

(2S)-6-Methyl-imidazo[2,1-b]thiazole-5-carboxylic acid [1-(3',4'-dimethyl-biphenyl-2-carbonyl)-azetidin-2-ylmethyl]-amide This compound has been prepared as in Example 6 but using (2S)-6-methyl-imidazo[2,1-b]thiazole-5-carbonylic acid(azetidin-2-ylmethyl)-amide hydrochloride and 3',4'-dimethyl-biphenyl-2-carboxylic acid.
LC-MS: rt=0.91 min, 459 [M+H]$^+$.

Example 20

(2S)-6-Methyl-imidazo[2,1-b]thiazole-5-carboxylic acid [1-(2-amino-5-m-tolyl-thiazole-4-carbonyl)-azetidin-2-ylmethyl]-amide a) Synthesis of 2-amino-5-m-tolyl-thiazole-4-carboxylic acid methyl ester This compound was synthesised as 2-methyl-5-m-tolyl-thiazole-4-carboxylic acid methyl ester but using thiourea instead thioacetamide.
LC-MS: rt=0.78 min, 249 [M+H]$^+$.

b) Synthesis of 2-amino-5-m-tolyl-thiazole-4-carboxylic acid

This compound was synthesised as 5-(4-fluoro-phenyl)-2-methyl-thiazole-4-carboxylic acid.
LC-MS: rt=0.65 min, 235 [M+H]$^+$.

c) Synthesis of (2S)-6-methyl-imidazo[2,1-b]thiazole-5-carboxylic acid [1-(2-amino-5-m-tolyl-thiazole-4-carbonyl)-azetidin-2-ylmethyl]-amide This compound has been prepared as in Example 6 but using (2S)-6-methyl-imidazo[2,1-b]thiazole-5-carbonylic acid(azetidin-2-ylmethyl)-amide hydrochloride and 2-amino-5-m-tolyl-thiazole-4-carboxylic acid.
LC-MS: rt=0.73 min, 467 [M+H]$^+$.

Example 21

(2S)-6-Chloro-imidazo[2,1-b]thiazole-5-carboxylic acid [1-(2-methyl-5-m-tolyl-thiazole-4-carbonyl)-azetidin-2-ylmethyl]-amide a) Synthesis of (2S)-2-{[(6-chloro-imidazo[2,1-b]thiazole-5-carbonyl)-amino]-methyl}-azetidine-1-carboxylic acid tent-butyl ester This compound has been prepared as in Example 6 but reaction of (2S)-aminomethyl-azetidine-1-carboxylic acid tert-butyl ester with commercially available 6-chloro-imidazo[2,1-b]thiazole-5-carboxylic acid.
LC-MS: rt=0.93 min, 371 [M+H]$^+$.

b) Synthesis of (2S)-6-chloro-imidazo[2,1-b]thiazole-5-carbonylic acid(azetidin-2-ylmethyl)-amide hydrochloride This compound has been prepared as in Example 6.
LC-MS: rt=0.55 min, 271 [M+H]$^+$.

c) Synthesis of (2S)-6-Chloro-imidazo[2,1-b]thiazole-5-carboxylic acid [1-(2-methyl-5-m-tolyl-thiazole-4-carbonyl)-azetidin-2-ylmethyl]-amide This compound has been prepared as in Example 6 but using (2S)-6-chloro-imidazo[2,1-b]thiazole-5-carbonylic acid(azetidin-2-ylmethyl)-amide hydrochloride and 2-methyl-5-m-tolyl-thiazole-4-carboxylic acid.
LC-MS: rt=0.94 min, 486 [M]$^+$.

Example 22

(2S)-6-Chloro-imidazo[2,1-b]thiazole-5-carboxylic acid [1-(2-amino-5-m-tolyl-thiazole-4-carbonyl)-azetidin-2-ylmethyl]-amide This compound has been prepared as in Example 6 but using (2S)-6-chloro-imidazo[2,1-b]thiazole-5-carbonylic acid(azetidin-2-ylmethyl)-amide hydrochloride and 2-amino-5-m-tolyl-thiazole-4-carboxylic acid.
LC-MS: rt=0.81 min, 487 [M+H]$^+$.

Example 23

(2RS)-Benzofuran-4-carboxylic acid [1-(3',4'-dimethyl-biphenyl-2-carbonyl)-azetidin-2-ylmethyl]-amide This compound has been prepared as in Example 1 but using 3',4'-dimethyl-biphenyl-2-carboxylic acid.
LC-MS: rt=0.89 min, 439 [M+H]$^+$.

53

Example 24

(2RS)-6-Methyl-imidazo[2,1-b]thiazole-5-carboxylic acid{1-[5-(3,4-dimethyl-phenyl)-2-methyl-thiazole-4-carbonyl]-azetidin-2-ylmethyl}-amide This compound has been prepared as in Example 5 but using 5-(3,4-dimethyl-phenyl)-2-methyl-thiazole-4-carboxylic acid.
LC-MS: rt=0.88 min, 480 [M+H]+.

Example 25

(2RS)-6-Methyl-imidazo[2,1-b]thiazole-5-carboxylic acid{1-[5-(3-methoxy-phenyl)-2-methyl-thiazole-4-carbonyl]-azetidin-2-ylmethyl}-amide a) Synthesis of 3-chloro-3-(3-methoxy-phenyl)-2-oxo-propionic acid methyl ester This compound was synthesised as 3-chloro-3-(4-fluoro-phenyl)-2-oxo-propionic acid methyl ester but using 3-methoxybenzaldehyde instead 4-fluorobenzaldehyde.

b) Synthesis of 5-(3-methoxy-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.90 min, 263 [M+H]+.

c) Synthesis of 5-(3-methoxy-phenyl)-2-methyl-thiazole-4-carboxylic acid

This compound was synthesised as 5-(4-fluoro-phenyl)-2-methyl-thiazole-4-carboxylic acid.
LC-MS: rt=0.80 min, 250 [M+H]+.

d) Synthesis of 6-methyl-imidazo[2,1-b]thiazole-5-carboxylic acid{1-[5-(3-methoxy-phenyl)-2-methyl-thiazole-4-carbonyl]-azetidin-2-ylmethyl}-amide This compound has been prepared as in Example 5 but using 5-(3-methoxy-phenyl)-2-methyl-thiazole-4-carboxylic acid.
LC-MS: rt=0.81 min, 482 [M+H]+.

Example 26

(2RS)-6-Methyl-imidazo[2,1-b]thiazole-5-carboxylic acid{1-[5-(3-chloro-phenyl)-2-methyl-thiazole-4-carbonyl]-azetidin-2-ylmethyl}-amide a) Synthesis of 3-chloro-3-(3-chloro-phenyl)-2-oxo-propionic acid methyl ester This compound was synthesised as 3-chloro-3-(4-fluoro-phenyl)-2-oxo-propionic acid methyl ester but using 3-chlorobenzaldehyde instead 4-fluorobenzaldehyde.

b) Synthesis of 5-(3-chloro-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.94 min, 268 [M+H]+.

54 c) Synthesis of 5-(3-chloro-phenyl)-2-methyl-thiazole-4-carboxylic acid

This compound was synthesised as 5-(4-fluoro-phenyl)-2-methyl-thiazole-4-carboxylic acid.
LC-MS: rt=0.84 min, 254 [M+H]+.

d) Synthesis of 6-methyl-imidazo[2,1-b]thiazole-5-carboxylic acid{1-[5-(3-chloro-phenyl)-2-methyl-thiazole-4-carbonyl]-azetidin-2-ylmethyl}-amide This compound has been prepared as in Example 5 but using 5-(3-chloro-phenyl)-2-methyl-thiazole-4-carboxylic acid.
LC-MS: rt=0.84 min, 486 [M+H]+.

Example 27

(2RS)-6-Methyl-imidazo[2,1-b]thiazole-5-carboxylic acid{1-[2-methyl-5-(3-trifluoromethyl-phenyl)-thiazole-4-carbonyl]-azetidin-2-ylmethyl}-amide a) Synthesis of 3-chloro-2-oxo-3-(3-trifluoromethyl-phenyl)-propionic acid methyl ester This compound was synthesised as 3-chloro-3-(4-fluoro-phenyl)-2-oxo-propionic acid methyl ester but using 3-trifluoromethylbenzaldehyde instead 4-fluorobenzaldehyde.

b) Synthesis of 2-methyl-5-(3-trifluoromethyl-phenyl)-thiazole-4-carboxylic acid methyl ester This compound was synthesised as 5-(4-fluoro-phenyl)-2-methyl-thiazole-4-carboxylic acid methyl ester
LC-MS: rt=0.98 min, 302 [M+H]+.

c) Synthesis of 2-methyl-5-(3-trifluoromethyl-phenyl)-thiazole-4-carboxylic acid This compound was synthesised as 5-(4-fluoro-phenyl)-2-methyl-thiazole-4-carboxylic acid.
LC-MS: rt=0.88 min, 288 [M+H]+.

d) Synthesis of 6-methyl-imidazo[2,1-b]thiazole-5-carboxylic acid{1-[2-methyl-5-(3-trifluoromethyl-phenyl)-thiazole-4-carbonyl]-azetidin-2-ylmethyl}-amide This compound has been prepared as in Example 5 but using 2-methyl-5-(3-trifluoromethyl-phenyl)-thiazole-4-carboxylic acid.
LC-MS: rt=0.88 min, 520 [M+H]+.

Example 28

(2RS)-6-Methyl-imidazo[2,1-b]thiazole-5-carboxylic acid{1-[5-(4-methoxy-phenyl)-2-methyl-thiazole-4-carbonyl]-azetidin-2-ylmethyl}-amide a) Synthesis of 3-chloro-3-(4-methoxy-phenyl)-2-oxo-propionic acid methyl ester This compound was synthesised as 3-chloro-3-(4-fluoro-phenyl)-2-oxo-propionic acid methyl ester but using 4-methoxybenzaldehyde instead 4-fluorobenzaldehyde.

b) Synthesis of 5-(4-methoxy-phenyl)-2-methyl-thiazole-4-carboxylic acid methyl ester This compound was synthesised as 5-(4-fluoro-phenyl)-2-methyl-thiazole-4-carboxylic acid methyl ester.

LC-MS: rt=0.91 min, 263 [M]+.

c) Synthesis of 5-(4-methoxy-phenyl)-2-methyl-thiazole-4-carboxylic acid

This compound was synthesised as 5-(4-fluoro-phenyl)-2-methyl-thiazole-4-carboxylic acid.

LC-MS: rt=0.80 min, 250 [M+H]+.

d) Synthesis of 6-methyl-imidazo[2,1-b]thiazole-5-carboxylic acid{1-[5-(4-methoxy-phenyl)-2-methyl-thiazole-4-carbonyl]-azetidin-2-ylmethyl}-amide This compound has been prepared as in Example 5 but using 5-(4-methoxy-phenyl)-2-methyl-thiazole-4-carboxylic acid.

LC-MS: rt=0.80 min, 482 [M+H]+.

Example 29

(2RS)-6-Methyl-imidazo[2,1-b]thiazole-5-carboxylic acid{1-[5-(3,5-difluoro-phenyl)-2-methyl-thiazole-4-carbonyl]-azetidin-2-ylmethyl}-amide a) Synthesis of 3-chloro-3-(3,5-difluoro-phenyl)-2-oxo-propionic acid methyl ester This compound was synthesised as 3-chloro-3-(4-fluoro-phenyl)-2-oxo-propionic acid methyl ester but using 3,5-difluorobenzaldehyde instead 4-fluorobenzaldehyde.

b) Synthesis of 5-(3,5-difluoro-phenyl)-2-methyl-thiazole-4-carboxylic acid methyl ester This compound was synthesised as 5-(4-fluoro-phenyl)-2-methyl-thiazole-4-carboxylic acid methyl ester.

LC-MS: rt=0.92 min, 270 [M]+.

c) Synthesis of 5-(3,5-difluoro-phenyl)-2-methyl-thiazole-4-carboxylic acid

This compound was synthesised as 5-(4-fluoro-phenyl)-2-methyl-thiazole-4-carboxylic acid.

LC-MS: rt=0.82 min, 256 [M+H]+.

d) Synthesis of (2RS)-6-methyl-imidazo[2,1-b]thiazole-5-carboxylic acid{1-[5-(3,5-difluoro-phenyl)-2-methyl-thiazole-4-carbonyl]-azetidin-2-ylmethyl}-amide This compound has been prepared as in Example 5 but using 5-(3,5-difluoro-phenyl)-2-methyl-thiazole-4-carboxylic acid.

LC-MS: rt=0.91 min, 488 [M+H]+.

Example 30

(2RS)-6-Methyl-imidazo[2,1-b]thiazole-5-carboxylic acid{1-[5-(3-bromo-4-fluoro-phenyl)-2-methyl-thiazole-4-carbonyl]-azetidin-2-ylmethyl}-amide a) Synthesis of 3-(3-bromo-4-fluoro-phenyl)-3-chloro-2-oxo-propionic acid methyl ester This compound was synthesised as 3-chloro-3-(4-fluoro-phenyl)-2-oxo-propionic acid methyl ester but using 3-bromo-4-fluorobenzaldehyde instead 4-fluorobenzaldehyde.

b) Synthesis of 5-(3-bromo-4-fluoro-phenyl)-2-methyl-thiazole-4-carboxylic acid methyl ester This compound was synthesised as 5-(4-fluoro-phenyl)-2-methyl-thiazole-4-carboxylic acid methyl ester.

LC-MS: rt=0.96 min, 332 [M+H]+.

c) Synthesis of 5-(3-bromo-4-fluoro-phenyl)-2-methyl-thiazole-4-carboxylic acid

This compound was synthesised as 5-(4-fluoro-phenyl)-2-methyl-thiazole-4-carboxylic acid.

LC-MS: rt=0.86 min, 316 [M+H]+.

d) Synthesis of (2RS)-6-methyl-imidazo[2,1-b]thiazole-5-carboxylic acid{1-[5-(3-bromo-4-fluoro-phenyl)-2-methyl-thiazole-4-carbonyl]-azetidin-2-ylmethyl}-amide This compound has been prepared as in Example 5 but using 5-(3-bromo-4-fluoro-phenyl)-2-methyl-thiazole-4-carboxylic acid.

LC-MS: rt=0.87 min, 550 [M+H]+.

Example 31

(2RS)-6-Methyl-imidazo[2,1-b]thiazole-5-carboxylic acid{1-[5-(4-chloro-phenyl)-2-methyl-thiazole-4-carbonyl]-azetidin-2-ylmethyl}-amide a) Synthesis of 3-chloro-3-(4-chloro-phenyl)-2-oxo-propionic acid methyl ester This compound was synthesised as 3-chloro-3-(4-fluoro-phenyl)-2-oxo-propionic acid methyl ester but using 4-chlorobenzaldehyde instead 4-fluorobenzaldehyde.

b) Synthesis of 5-(4-chloro-phenyl)-2-methyl-thiazole-4-carboxylic acid methyl ester This compound was synthesised as 5-(4-fluoro-phenyl)-2-methyl-thiazole-4-carboxylic acid methyl ester.

LC-MS: rt=0.94 min, 268 [M+H]+.

c) Synthesis of 5-(4-chloro-phenyl)-2-methyl-thiazole-4-carboxylic acid

This compound was synthesised as 5-(4-fluoro-phenyl)-2-methyl-thiazole-4-carboxylic acid.

LC-MS: rt=0.85 min, 254 [M+H]+.

d) Synthesis of (2RS)-6-methyl-imidazo[2,1-b]thiazole-5-carboxylic acid{1-[5-(4-chloro-phenyl)-2-methyl-thiazole-4-carbonyl]-azetidin-2-ylmethyl}-amide This compound has been prepared as in Example 5 but using 5-(4-chloro-phenyl)-2-methyl-thiazole-4-carboxylic acid.
LC-MS: rt=0.83 min, 486 [M]+.

Example 32

(2RS)-6-Methyl-imidazo[2,1-b]thiazole-5-carboxylic acid{1-[5-(3,4-dichloro-phenyl)-2-methyl-thiazole-4-carbonyl]-azetidin-2-ylmethyl}-amide a) Synthesis of 3-chloro-3-(3,4-dichloro-phenyl)-2-oxo-propionic acid methyl ester This compound was synthesised as 3-chloro-3-(4-fluoro-phenyl)-2-oxo-propionic acid methyl ester but using 3,4-dichlorobenzaldehyde instead 4-fluorobenzaldehyde.

b) Synthesis of 5-(3,4-dichloro-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.99 min, 302 [M]+.

c) Synthesis of 5-(3,4-dichloro-phenyl)-2-methyl-thiazole-4-carboxylic acid

This compound was synthesised as 5-(4-fluoro-phenyl)-2-methyl-thiazole-4-carboxylic acid.
LC-MS: rt=0.88 min, 288 [M]+.

d) Synthesis of (2RS)-6-methyl-imidazo[2,1-b]thiazole-5-carboxylic acid{1-[5-(3,4-dichloro-phenyl)-2-methyl-thiazole-4-carbonyl]-azetidin-2-ylmethyl}-amide This compound has been prepared as in Example 5 but using 5-(3,4-dichloro-phenyl)-2-methyl-thiazole-4-carboxylic acid.
LC-MS: rt=0.89 min, 520 [M]+.

Example 33

(2RS)-6-Chloro-imidazo[2,1-b]thiazole-5-carboxylic acid{1-[5-(3,4-dimethyl-phenyl)-2-methyl-thiazole-4-carbonyl]-azetidin-2-ylmethyl}-amide This compound has been prepared as in Example 5 but using 5-(3,4-dimethyl-phenyl)-2-methyl-thiazole-4-carboxylic acid.
LC-MS: rt=0.98 min, 500 [M]+.

Example 34

(2RS)-6-Chloro-imidazo[2,1-b]thiazole-5-carboxylic acid [1-(2-methyl-5-m-tolyl-thiazole-4-carbonyl)-azetidin-2-ylmethyl]-amide This compound has been prepared as in Example 5 but using 2-methyl-5-m-tolyl-thiazole-4-carboxylic acid.
LC-MS: rt=0.94 min, 486 [M]+.

Example 35

(2RS)-2-Methyl-benzofuran-4-carboxylic acid [1-(2-methyl-5-m-tolyl-thiazole-4-carbonyl)-azetidin-2-ylmethyl]-amide This compound has been prepared as in Example 5 but using 2-methyl-benzofuran-4-carboxylic acid which has been obtained by saponification with aqueous NaOH in MeOH of 2-methyl-benzofuran-4-carboxylic acid methyl ester (Ishikawa T. et al, *Heterocycles,* 1994, 39, 1, 371-380).
LC-MS: rt=1.01 min, 460 [M+H]+.

Example 36

(2RS)-2H-Chromene-5-carboxylic acid [1-(2-methyl-5-m-tolyl-thiazole-4-carbonyl)-azetidin-2-ylmethyl]-amide This compound has been prepared as in Example 5 but using 2H-chromene-5-carboxylic acid which has been obtained by saponification with aqueous NaOH in MeOH of 2H-chromene-5-carboxylic acid methyl ester (Ishikawa T. et al, *Heterocycles,* 1994, 39, 1, 371-380).
LC-MS: rt=0.97 min, 460 [M+H]+.

Example 37

(2RS)-Benzooxazole-4-carboxylic acid [1-(2-methyl-5-m-tolyl-thiazole-4-carbonyl)-azetidin-2-ylmethyl]-amide This compound has been prepared as in Example 5 but using benzooxazole-4-carboxylic acid (WO00/51608).
LC-MS: rt=0.92 min, 447 [M+H]+.

Example 38

(2RS)-Benzofuran-3-carboxylic acid [1-(2-methyl-5-m-tolyl-thiazole-4-carbonyl)-azetidin-2-ylmethyl]-amide This compound has been prepared as in Example 5 but using commercially available benzofuran-3-carboxylic acid.
LC-MS: rt=1.00 min, 446 [M+H]+.

Example 39

(2RS)-2-Methyl-benzofuran-3-carboxylic acid [1-(2-methyl-5-m-tolyl-thiazole-4-carbonyl)-azetidin-2-ylmethyl]-amide This compound has been prepared as in Example 5 but using 2-methyl-benzofuran-3-carboxylic acid (WO03/000649).
LC-MS: rt=1.02 min, 460 [M+H]+.

Example 40

(2RS)-3,5-Dimethyl-imidazo[2,1-b]thiazole-6-carboxylic acid [1-(2-methyl-5-m-tolyl-thiazole-4-carbonyl)-azetidin-2-ylmethyl]-amide This compound has been prepared as in Example 5 but using 3,5-dimethyl-imidazo[2,1-b]thiazole-6-carboxylic acid which has been obtained by saponification with aqueous NaOH in EtOH of 3,5-dimethyl-imidazo[2,1-b]thiazole-6-carboxylic acid ethyl ester (DE2505068).

LC-MS: rt=0.92 min, 480 [M+H]$^+$.

Example 41

(2RS)-3,4-Dihydro-2H-benzo[1,4]oxazine-5-carboxylic acid [1-(2-methyl-5-m-tolyl-thiazole-4-carbonyl)-azetidin-2-ylmethyl]-amide This compound has been prepared as in Example 5 but using 3,4-dihydro-2H-benzo[1,4]oxazine-5-carboxylic acid (EP310096).

LC-MS: rt=0.98 min, 463 [M+H]$^+$.

Example 42

(2RS)-5-Methyl-imidazo[2,1-b]thiazole-6-carboxylic acid [1-(2-methyl-5-m-tolyl-thiazole-4-carbonyl)-azetidin-2-ylmethyl]-amide This compound has been prepared as in Example 5 but using 5-methyl-imidazo[2,1-b]thiazole-6-carboxylic acid which has been obtained by saponification with aqueous NaOH in EtOH of 5-methyl-imidazo[2,1-b]thiazole-6-carboxylic acid ethyl ester (DE2505068).

LC-MS: rt=0.89 min, 466 [M+H]$^+$.

Example 43

(2RS)-4-Methyl-3-oxo-3,4-dihydro-2H-benzo[1,4]oxazine-8-carboxylic acid [1-(2-methyl-5-m-tolyl-thiazole-4-carbonyl)-azetidin-2-ylmethyl]-amide This compound has been prepared as in Example 5 but using 4-methyl-3-oxo-3,4-dihydro-2H-benzo[1,4]oxazine-8-carboxylic acid (Kawakita T. et al, *Chemical & Pharmaceutical Bulletin*, 1992, 40, 3, 624-630).

LC-MS: rt=0.91 min, 491 [M+H]$^+$.

Example 44

(2RS)-Imidazo[2,1-b]thiazole-5-carboxylic acid [1-(2-methyl-5-m-tolyl-thiazole-4-carbonyl)-azetidin-2-ylmethyl]-amide This compound has been prepared as in Example 5 but using imidazo[2,1-b]thiazole-5-carboxylic acid (Kochergin P. M. et al, *Journal of General Chemistry USSR*, 1960, 30, 1542-1547 and Mazur I. A. et al, *Chemistry of Heterocyclic Compounds*, 1970, 6, 470-473)

LC-MS: rt=0.84 min, 452 [M+H]$^+$.

Example 45

(2RS)-Imidazo[2,1-b]thiazole-5-carboxylic acid [1-(3',4'-dimethyl-biphenyl-2-carbonyl)-azetidin-2-ylmethyl]-amide This compound has been prepared as in Example 5 but using commercially available 3',4'-dimethyl-biphenyl-2-carboxylic acid.

LC-MS: rt=0.93 min, 445 [M+H]$^+$.

Example 46

(2RS)-3-Methyl-imidazo[2,1-b]thiazole-5-carboxylic acid [1-(3',4'-dimethyl-biphenyl-2-carbonyl)-azetidin-2-ylmethyl]-amide This compound has been prepared as in Example 5 but using 3-methyl-imidazo[2,1-b]thiazole-5-carboxylic acid which has been prepared by oxidation with sodium chlorite of 3-methyl-imidazo[2,1-b]thiazole-5-carboxaldehyde (WO95/029922).

LC-MS: rt=0.93 min, 459 [M+H]$^+$.

Example 47

(2RS)-3,5-Dimethyl-imidazo[2,1-b]thiazole-6-carboxylic acid [1-(3',4'-dimethyl-biphenyl-2-carbonyl)-azetidin-2-ylmethyl]-amide This compound has been prepared as in Example 5 but using 3',4'-dimethyl-biphenyl-2-carboxylic acid.

LC-MS: rt=1.00 min, 473 [M+H]$^+$.

Example 48

(2RS)-6-Chloro-imidazo[2,1-b]thiazole-5-carboxylic acid [1-(3',4'-dimethyl-biphenyl-2-carbonyl)-azetidin-2-ylmethyl]-amide This compound has been prepared as in Example 5 but using 3',4'-dimethyl-biphenyl-2-carboxylic acid.

LC-MS: rt=1.00 min, 479 [M+H]$^+$.

Example 49

(2RS)-6-Methyl-imidazo[2,1-b]thiazole-5-carboxylic acid [1-(biphenyl-2-sulfonyl)-azetidin-2-ylmethyl]-amide This compound has been prepared as in Example 2 but using 6-methyl-imidazo[2,1-b]thiazole-5-carboxylic acid.

LC-MS: rt=0.96 min, 467 [M+H]$^+$.

Example 50

(2RS)-6-Trifluoromethyl-imidazo[2,1-b]thiazole-5-carboxylic acid [1-(2-methyl-5-m-tolyl-thiazole-4-carbonyl)-azetidin-2-ylmethyl]-amide a) Synthesis of 6-trifluoromethyl-imidazo[2,1-b]thiazole-5-carbaldehyde The Vilsmeier reagent was prepared at 0-5° C. by dropping POCl$_3$ 0.262 mL (2.810 mmol) into a stirred solution of dry DMF 0.262 mL (3.383 mmol) in 0.4 mL of CHCl$_3$. 6-trifluoromethyl-imidazo[2,1-b]thiazole (Moazzam M. et al, *Indian Journal of Chemistry: Section B*, 1988, 27B(11), 1051-1053) 100 mg (0.520 mmol) in 3 mL CHCl$_3$ was added dropwise to the Vilsmeier reagent while maintaining stirring and cooling. The reaction mixture was kept for 3 h at RT and under reflux for 39 h. After cooling to RT, the reaction mixture was poured into ice-water, extracted with DCM (3×), dried over MgSO$_4$, filtered and concentrated under reduced pressure to give a crude oil.

FC (n-heptane/EA:8/2 to 1/1) gave the title compound as an oil (360 mg, 52%).

$^1$H-NMR (CDCl$_3$): δ=7.30 (d, 2H); 8.45 (s, 1H); 10.05 (s, 1H).

b) Synthesis of 6-trifluoromethyl-imidazo[2,1-b]thiazole-5-carboxylic acid

A solution of sodium chlorite 418.986 mg (4.633 mmol) and sodium dihydrogen phosphate dihydrate 553.971 mg (3.551 mmol) in water 3.94 mL (218.895 mmol) was added dropwise to a solution of 6-trifluoromethyl-imidazo[2,1-b]thiazole-5-carbaldehyde 119 mg (0.54 mmol) in t-BuOH (3.94 mL). The mixture was stirred for 2 h30 at RT. The mixture was then concentrated in vacuo to remove t-BuOH, a white precipitate was formed and filtered to give the title compound as a white solid (70 mg, 55%).

LC-MS: rt=0.74 min, 278 [M+H+MeCN]$^+$.

c) Synthesis of (2RS)-6-trifluoromethyl-imidazo[2,1-b]thiazole-5-carboxylic acid [1-(2-methyl-5-m-tolyl-thiazole-4-carbonyl)-azetidin-2-ylmethyl]-amide This compound has been prepared as in Example 5 but using 6-trifluoromethyl-imidazo[2,1-b]thiazole-5-carboxylic acid.

LC-MS: rt=0.98 min, 520 [M+H]$^+$.

Example 51

(2RS)-6-Methyl-imidazo[2,1-b]thiazole-5-carboxylic acid [1-(2-methyl-5-phenyl-thiazole-4-carbonyl)-azetidin-2-ylmethyl]-amide a) Synthesis of 3-chloro-2-oxo-3-phenyl-propionic acid methyl ester This compound was synthesised as 3-chloro-3-(4-fluoro-phenyl)-2-oxo-propionic acid methyl ester but using benzaldehyde instead 4-fluorobenzaldehyde.

b) Synthesis of 2-methyl-5-phenyl-thiazole-4-carboxylic acid methyl ester

This compound was synthesised as 5-(4-fluoro-phenyl)-2-methyl-thiazole-4-carboxylic acid methyl ester.

LC-MS: rt=0.86 min, 234 [M+H]$^+$.

c) Synthesis of 2-methyl-5-phenyl-thiazole-4-carboxylic acid

This compound was synthesised as 5-(4-fluoro-phenyl)-2-methyl-thiazole-4-carboxylic acid.

LC-MS: rt=0.78 min, 220 [M+H]$^+$.

d) Synthesis of (2RS)-6-methyl-imidazo[2,1-b]thiazole-5-carboxylic acid [1-(2-methyl-5-phenyl-thiazole-4-carbonyl)-azetidin-2-ylmethyl]-amide This compound has been prepared as in Example 5 but using 2-methyl-5-phenyl-thiazole-4-carboxylic acid.

LC-MS: rt=0.80 min, 452 [M+H]$^+$.

Example 52

(2RS)-3,4-Dihydro-2H-benzo[1,4]oxazine-5-carboxylic acid [1-(2-amino-5-m-tolyl-thiazole-4-carbonyl)-azetidin-2-ylmethyl]-amide This compound has been prepared as in Example 5 but using 3,4-dihydro-2H-benzo[1,4]oxazine-5-carboxylic acid (EP310096).

LC-MS: rt=0.89 min, 464 [M+H]$^+$.

Example 53

(2RS)-3-Methyl-imidazo[2,1-b]thiazole-2-carboxylic acid [1-(3',4'-dimethyl-biphenyl-2-carbonyl)-azetidin-2-ylmethyl]-amide This compound has been prepared as in Example 5 but using 5-methyl-imidazo[2,1-b]thiazole-6-carboxylic acid which has been obtained by saponification with aqueous NaOH in EtOH of 3-methyl-imidazo[2,1-b]thiazole-2-carboxylic acid ethyl ester (WO02/46158).

LC-MS: rt=0.83 min, 459 [M+H]$^+$.

Example 54

(2RS)-4-Methyl-3,4-dihydro-2H-benzo[1,4]oxazine-8-carboxylic acid [1-(2-methyl-5-m-tolyl-thiazole-4-carbonyl)-azetidin-2-ylmethyl]-amide This compound has been prepared as in Example 5 but using 4-methyl-3,4-dihydro-2H-benzo[1,4]oxazine-8-carboxylic acid (Kuroita T. et al, *Chemical & Pharmaceutical Bulletin,* 1996, 44, 4, 756-764).

LC-MS: rt=0.96 min, 477 [M+H]$^+$.

Example 55

(2RS)-3-Methyl-imidazo[2,1-b]thiazole-2-carboxylic acid [1-(2-methyl-5-m-tolyl-thiazole-4-carbonyl)-azetidin-2-ylmethyl]-amide This compound has been prepared as in Example 5 but using 5-methyl-imidazo[2,1-b]thiazole-6-carboxylic acid which has been obtained by saponification with aqueous NaOH in EtOH of 3-methyl-imidazo[2,1-b]thiazole-2-carboxylic acid ethyl ester (WO02/46158).

LC-MS: rt=0.77 min, 466 [M+H]$^+$.

Example 56

(2RS)-Chroman-5-carboxylic acid [1-(2-methyl-5-m-tolyl-thiazole-4-carbonyl)-azetidin-2-ylmethyl]-amide This compound has been prepared as in Example 5 but using chroman-5-carboxylic acid which has been obtained by catalytic hydrogenation with Pd—C 10% and saponification with NaOH of methyl 2H-chromene-5-carboxylate (Ishikawa T. et al *Heterocycles,* 1994, 39, 1, 371-380).

LC-MS: rt=0.97 min, 462 [M+H]$^+$.

Example 57

(2RS)-Chroman-8-carboxylic acid [1-(2-methyl-5-m-tolyl-thiazole-4-carbonyl)-azetidin-2-ylmethyl]-amide This compound has been prepared as in Example 5 but using chroman-8-carboxylic acid (WO94/19344).
LC-MS: rt=0.99 min, 462 [M+H]$^+$.

Example 58

(2RS)-3-Oxo-3,4-dihydro-2H-benzo[1,4]oxazine-5-carboxylic acid [1-(2-methyl-5-m-tolyl-thiazole-4-carbonyl)-azetidin-2-ylmethyl]-amide This compound has been prepared as in Example 5 but using 3-oxo-3,4-dihydro-2H-benzo[1,4]oxazine-5-carboxylic acid (Ceccarelli S. et al, *Bioorganic & Medicinal Chemistry Letters* 2007, 17, 5, 1302-1306).
LC-MS: rt=0.95 min, 477 [M+H]$^+$.

Example 59

(2RS)-2-Methyl-imidazo[2,1-b]thiazole-5-carboxylic acid [1-(3',4'-dimethyl-biphenyl-2-carbonyl)-azetidin-2-ylmethyl]-amide This compound has been prepared as in Example 5 but using 2-methyl-imidazo[2,1-b]thiazole-5-carboxylic acid.
LC-MS: rt=0.94 min, 459 [M+H]$^+$.

Example 60

(2RS)-6-Methyl-imidazo[2,1-b]thiazole-5-carboxylic acid{1-[5-(2,4-dimethyl-phenyl)-2-methyl-thiazole-4-carbonyl]-azetidin-2-ylmethyl}-amide a) Synthesis of 3-chloro-3-(2,4-dimethyl-phenyl)-2-oxo-propionic acid methyl ester This compound was synthesised as 3-chloro-3-(4-fluoro-phenyl)-2-oxo-propionic acid methyl ester but using 2,4-dimethylbenzaldehyde instead 4-fluorobenzaldehyde.

b) Synthesis of 5-(2,4-dimethyl-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.96 min, 262 [M+H]$^+$.

c) Synthesis of 5-(2,4-dimethyl-phenyl)-2-methyl-thiazole-4-carboxylic acid

This compound was synthesised as 5-(4-fluoro-phenyl)-2-methyl-thiazole-4-carboxylic acid.
LC-MS: rt=0.85 min, 248 [M+H]$^+$.

d) Synthesis of (2RS)-6-methyl-imidazo[2,1-b]thiazole-5-carboxylic acid{1-[5-(2,4-dimethyl-phenyl)-2-methyl-thiazole-4-carbonyl]-azetidin-2-ylmethyl}-amide This compound has been prepared as in Example 5 but using 5-(2,4-dimethyl-phenyl)-2-methyl-thiazole-4-carboxylic acid.
LC-MS: rt=0.86 min, 480 (M+1, ES+).

Example 61

(2RS)-3-Methyl-imidazo[2,1-b]thiazole-5-carboxylic acid [1-(2-methyl-5-m-tolyl-thiazole-4-carbonyl)-azetidin-2-ylmethyl]-amide This compound has been prepared as in Example 5 but using 3-methyl-imidazo[2,1-b]thiazole-5-carboxylic acid.
LC-MS: rt=0.83 min, 466 [M+H]$^+$.

Example 62

(2RS)-2-Methyl-benzooxazole-4-carboxylic acid [1-(2-methyl-5-m-tolyl-thiazole-4-carbonyl)-azetidin-2-ylmethyl]-amide This compound has been prepared as in Example 5 but using 2-methyl-benzooxazole-4-carboxylic acid which has been prepared by saponification with NaOH in MeOH of 2-methyl-benzooxazole-4-carboxylic acid methyl ester (Goldstein S. W. et al, *Journal of Heterocyclic Chemistry* 1990, 27, 335-336).
LC-MS: rt=0.95 min, 461 [M+H]$^+$.

Example 63

(2RS)-3,6-Dimethyl-imidazo[2,1-b]thiazole-5-carboxylic acid [1-(3',4'-dimethyl-biphenyl-2-carbonyl)-azetidin-2-ylmethyl]-amide This compound has been prepared as in Example 5 but using 3,6-dimethyl-imidazo[2,1-b]thiazole-5-carboxylic acid.
LC-MS: rt=0.87 min, 473 [M+H]$^+$.

Example 64

(2RS)-6-Methyl-imidazo[2,1-b]thiazole-5-carboxylic acid{1-[5-(2-fluoro-phenyl)-2-methyl-thiazole-4-carbonyl]-azetidin-2-ylmethyl}-amide a) Synthesis of 3-chloro-3-(2-fluoro-phenyl)-2-oxo-propionic acid methyl ester This compound was synthesised as 3-chloro-3-(4-fluoro-phenyl)-2-oxo-propionic acid methyl ester but using 2-fluorobenzaldehyde instead 4-fluorobenzaldehyde.

b) Synthesis of 5-(2-fluoro-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.91 min, 252 [M+H]$^+$.

c) Synthesis of 5-(2-fluoro-phenyl)-2-methyl-thiazole-4-carboxylic acid

This compound was synthesised as 5-(4-fluoro-phenyl)-2-methyl-thiazole-4-carboxylic acid.
LC-MS: rt=0.82 min, 238 [M+H]$^+$.

d) Synthesis of (2RS)-6-methyl-imidazo[2,1-b]thiaz-ole-5-carboxylic acid{1-[5-(2-fluoro-phenyl)-2-methyl-thiazole-4-carbonyl]-azetidin-2-ylmethyl}-amide This compound has been prepared as in Example 5 but using 5-(2-fluoro-phenyl)-2-methyl-thiazole-4-carboxylic acid.
LC-MS: rt=0.81 min, 470 [M+H]$^+$.

Example 65

(2S)-Benzofuran-4-carboxylic acid [1-(naphthalene-1-sulfonyl)-azetidin-2-ylmethyl]-amide This compound has been prepared as in Example 2 but using benzofuran-4-carboxylic acid.
LC-MS: rt=1.00 min, 421 [M+H]$^+$.

Example 66

(2RS)-Benzofuran-4-carboxylic acid [1-(3'-fluoro-biphenyl-2-carbonyl)-azetidin-2-ylmethyl]-amide This compound has been prepared as in Example 2 but using 3'-fluoro-biphenyl-2-carboxylic acid and benzofuran-4-carboxylic acid.
LC-MS: rt=0.97 min, 429 [M+H]$^+$.

Example 67

(2RS)-6-Methyl-imidazo[2,1-b]thiazole-5-carboxylic acid{1-[5-(3,4-difluoro-phenyl)-2-methyl-thiazole-4-carbonyl]-azetidin-2-ylmethyl}-amide a) Synthesis of 3-chloro-3-(3,4-difluoro-phenyl)-2-oxo-propionic acid methyl ester This compound was synthesised as 3-chloro-3-(4-fluoro-phenyl)-2-oxo-propionic acid methyl ester but using 3,4-difluorobenzaldehyde instead 4-fluorobenzaldehyde.

b) Synthesis of 5-(3,4-difluoro-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.92 min, 270 [M+H]$^+$.

c) Synthesis of 5-(3,4-difluoro-phenyl)-2-methyl-thiazole-4-carboxylic acid

This compound was synthesised as 5-(4-fluoro-phenyl)-2-methyl-thiazole-4-carboxylic acid.
LC-MS: rt=0.82 min, 256 [M+H]$^+$.

d) Synthesis of (2RS)-6-methyl-imidazo[2,1-b]thiaz-ole-5-carboxylic acid{1-[5-(3,4-difluoro-phenyl)-2-methyl-thiazole-4-carbonyl]-azetidin-2-ylmethyl}-amide This compound has been prepared as in Example 5 but using 5-(3,4-difluoro-phenyl)-2-methyl-thiazole-4-carboxylic acid.
LC-MS: rt=0.85 min, 488 [M+H]$^+$.

Example 68

(2RS)-6-Methyl-imidazo[2,1-b]thiazole-5-carboxylic acid{1-[4-(4-chloro-phenyl)-2-methyl-thiazole-5-carbonyl]-azetidin-2-ylmethyl}-amide This compound has been prepared as in Example 5 but using 2-methyl-4-(4-chloro-phenyl)-thiazole-5-carboxylic acid.
LC-MS: rt=0.82 min, 486 [M+H]$^+$.

Example 69

(2RS)-2,6-Dimethyl-imidazo[2,1-b]thiazole-5-carboxylic acid [1-(3',4'-dimethyl-biphenyl-2-carbonyl)-azetidin-2-ylmethyl]-amide This compound has been prepared as in Example 5 but using 2,6-dimethyl-imidazo[2,1-b]thiazole-5-carboxylic acid.
LC-MS: rt=0.92 min, 473 [M+H]$^+$.

Example 70

(2RS)-2-Methyl-imidazo[2,1-b]thiazole-5-carboxylic acid [1-(2-methyl-5-m-tolyl-thiazole-4-carbonyl)-azetidin-2-ylmethyl]-amide This compound has been prepared as in Example 5 but using 2-methyl-imidazo[2,1-b.]thiazole-5-carboxylic acid.
LC-MS: rt=0.85 min, 466 [M+H]$^+$.

Example 71

(2RS)-Benzofuran-4-carboxylic acid [1-(2'-fluoro-biphenyl-2-carbonyl)-azetidin-2-ylmethyl]-amide This compound has been prepared as in Example 2 but using 2'-fluoro-biphenyl-2-carboxylic acid and benzofuran-4-carboxylic acid.
LC-MS: rt=0.97 min, 429 [M+H]$^+$.

Example 72

(2RS)-Benzofuran-4-carboxylic acid [1-(3'-trifluoromethyl-biphenyl-2-carbonyl)-azetidin-2-ylmethyl]-amide This compound has been prepared as in Example 2 but using 3'-trifluoromethyl-biphenyl-2-carboxylic acid and benzofuran-4-carboxylic acid.
LC-MS: rt=1.02 min, 479 [M+H]$^+$.

Example 73

(2RS)-6-Methyl-imidazo[2,1-b]thiazole-5-carboxylic acid{1-[4-(4-methoxy-phenyl)-2-methyl-thiazole-5-carbonyl]-azetidin-2-ylmethyl}-amide This compound has been prepared as in Example 5 but using 2-methyl-4-(4-methoxy-phenyl)-thiazole-5-carboxylic acid.
LC-MS: rt=0.77 min, 482 [M+H]$^+$.

Example 74

(2RS)-6-Methyl-imidazo[2,1-b]thiazole-5-carboxylic acid{1-[5-(2,3-dichloro-phenyl)-2-methyl-thiazole-4-carbonyl]-azetidin-2-ylmethyl}-amide a) Synthesis of 3-chloro-3-(2,3-dichloro-phenyl)-2-oxo-propionic acid methyl ester This compound was synthesised as 3-chloro-3-(4-fluoro-phenyl)-2-oxo-propionic acid methyl ester but using 2,3-dichlorobenzaldehyde instead 4-fluorobenzaldehyde.

b) Synthesis of 5-(2,3-dichloro-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.99 min, 302 [M]$^+$.

c) Synthesis of 5-(2,3-dichloro-phenyl)-2-methyl-thiazole-4-carboxylic acid

This compound was synthesised as 5-(4-fluoro-phenyl)-2-methyl-thiazole-4-carboxylic acid.
LC-MS: rt=0.88 min, 288 [M]$^+$.

d) Synthesis of (2RS)-6-methyl-imidazo[2,1-b]thiazole-5-carboxylic acid{1-[5-(2,3-dichloro-phenyl)-2-methyl-thiazole-4-carbonyl]-azetidin-2-ylmethyl}-amide This compound has been prepared as in Example 5 but using 5-(2,3-dichloro-phenyl)-2-methyl-thiazole-4-carboxylic acid.
LC-MS: rt=0.90 min, 520 [M+H]$^+$.

Example 75

(2RS)-6-Methyl-imidazo[2,1-b]thiazole-5-carboxylic acid{1-[5-(2,3-dimethyl-phenyl)-2-methyl-thiazole-4-carbonyl]-azetidin-2-ylmethyl}-amide a) Synthesis of 3-chloro-3-(2,3-dimethyl-phenyl)-2-oxo-propionic acid methyl ester This compound was synthesised as 3-chloro-3-(4-fluoro-phenyl)-2-oxo-propionic acid methyl ester but using 2,3-dimethylbenzaldehyde instead 4-fluorobenzaldehyde.

b) Synthesis of 5-(2,3-dimethyl-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.94 min, 262 [M+H]$^+$.

c) Synthesis of 5-(2,3-dimethyl-phenyl)-2-methyl-thiazole-4-carboxylic acid

This compound was synthesised as 5-(4-fluoro-phenyl)-2-methyl-thiazole-4-carboxylic acid.
LC-MS: rt=0.84 min, 248 [M+H]$^+$.

d) Synthesis of (2RS)-6-methyl-imidazo[2,1-b]thiazole-5-carboxylic acid{1-[5-(2,3-dimethyl-phenyl)-2-methyl-thiazole-4-carbonyl]-azetidin-2-ylmethyl}-amide This compound has been prepared as in Example 5 but using 5-(2,3-dimethyl-phenyl)-2-methyl-thiazole-4-carboxylic acid.
LC-MS: rt=0.86 min, 480 [M+H]$^+$.

Example 76

(2RS)-Benzofuran-4-carboxylic acid [1-(4'-fluoro-biphenyl-2-carbonyl)-azetidin-2-ylmethyl]-amide This compound has been prepared as in Example 2 but using 4'-fluoro-biphenyl-2-carboxylic acid and benzofuran-4-carboxylic acid.
LC-MS: rt=0.97 min, 429 [M+H]$^+$.

Example 77

(2RS)-Benzofuran-4-carboxylic acid [1-(4'-methyl-biphenyl-2-carbonyl)-azetidin-2-ylmethyl]-amide This compound has been prepared as in Example 2 but using 4'-methyl-biphenyl-2-carboxylic acid and benzofuran-4-carboxylic acid.
LC-MS: rt=1.00 min, 425 [M+H]$^+$.

Example 78

(2RS)-Cinnoline-4-carboxylic acid{1-[5-(4-fluoro-phenyl)-2-methyl-thiazole-4-carbonyl]-azetidin-2-ylmethyl}-amide This compound has been prepared as in Example 5 but using commercially available cinnoline-4-carboxylic acid.
LC-MS: rt=0.87 min, 462 [M+H]$^+$.

Example 79

(2RS)-1-Methyl-1H-indazole-3-carboxylic acid{1-[5-(4-fluoro-phenyl)-2-methyl-thiazole-4-carbonyl]-azetidin-2-ylmethyl}-amide This compound has been prepared as in Example 5 but using commercially available 1-methyl-1H-indazole-3-carboxylic acid.
LC-MS: rt=0.93 min, 464 [M+H]$^+$.

Example 80

(2RS)-Benzofuran-4-carboxylic acid [1-(3'-methyl-biphenyl-2-carbonyl)-azetidin-2-ylmethyl]-amide This compound has been prepared as in Example 2 but using 3'-methyl-biphenyl-2-carboxylic acid and benzofuran-4-carboxylic acid.
LC-MS: rt=1.00 min, 425 [M+H]$^+$.

Example 81

(2RS)-6-Methyl-imidazo[2,1-b]thiazole-5-carboxylic acid{1-[5-(2-chloro-phenyl)-2-methyl-thiazole-4-carbonyl]-azetidin-2-ylmethyl}-amide a) Synthesis of 3-chloro-3-(2-chloro-phenyl)-2-oxo-propionic acid methyl ester This compound was synthesised as 3-chloro-3-(4-fluoro-phenyl)-2-oxo-propionic acid methyl ester but using 2-chlorobenzaldehyde instead 4-fluorobenzaldehyde.

b) Synthesis of 5-(2-chloro-phenyl)-2-methyl-thiazole-4-carboxylic acid methyl ester This compound was synthesised as 5-(4-fluoro-phenyl)-2-methyl-thiazole-4-carboxylic acid methyl ester.
LC-MS: rt=0.92 min, 268 [M+H]$^+$.

c) Synthesis of 5-(2-chloro-phenyl)-2-methyl-thiazole-4-carboxylic acid

This compound was synthesised as 5-(2-chloro-phenyl)-2-methyl-thiazole-4-carboxylic acid.
LC-MS: rt=0.82 min, 253 [M+H]$^+$.

d) Synthesis of (2RS)-6-methyl-imidazo[2,1-b]thiazole-5-carboxylic acid{1-[5-(2-chloro-phenyl)-2-methyl-thiazole-4-carbonyl]-azetidin-2-ylmethyl}-amide This compound has been prepared as in Example 5 but using 5-(2-chloro-phenyl)-2-methyl-thiazole-4-carboxylic acid.
LC-MS: rt=0.86 min, 486 [M+H]$^+$.

Example 82

(2RS)-6-Methyl-imidazo[2,1-b]thiazole-5-carboxylic acid{1-[2-methyl-4-(3-trifluoromethyl-phenyl)-thiazole-5-carbonyl]-azetidin-2-ylmethyl}-amide This compound has been prepared as in Example 5 but using 2-methyl-4-(3-trifluoromethyl-phenyl)-thiazole-5-carboxylic acid.
LC-MS: rt=0.87 min, 520 [M+H]$^+$.

Example 83

(2RS)-6-Methyl-imidazo[2,1-b]thiazole-5-carboxylic acid [1-5-(2-methyl-5-m-tolyl-oxazole-4-carbonyl)-azetidin-2-ylmethyl]-amide This compound has been prepared as in Example 5 but using 2-methyl-5-m-tolyl-oxazole-4-carboxylic acid.
LC-MS: rt=0.85 min, 450 [M+H]$^+$.

Example 84

(2RS)-6-Methyl-imidazo[2,1-b]thiazole-5-carboxylic acid [1-(2-methyl-4-m-tolyl-thiazole-5-carbonyl)-azetidin-2-ylmethyl]-amide This compound has been prepared as in Example 5 but using 2-methyl-4-m-tolyl-thiazole-5-carboxylic acid.
LC-MS: rt=0.81 min, 466 [M+H]$^+$.

Example 85

(2RS)-6-Methyl-imidazo[2,1-b]thiazole-5-carboxylic acid{1-[4-(3-chloro-phenyl)-2-methyl-thiazole-5-carbonyl]-azetidin-2-ylmethyl}-amide This compound has been prepared as in Example 5 but using 2-methyl-4-(3-chloro-phenyl)-thiazole-5-carboxylic acid.
LC-MS: rt=0.82 min, 486 [M+H]$^+$.

Example 86

(2RS)-Benzo[d]isothiazole-3-carboxylic acid{1-[5-(4-fluoro-phenyl)-2-methyl-thiazole-4-carbonyl]-azetidin-2-ylmethyl}-amide This compound has been prepared as in Example 5 but using benzo[d]isothiazole-3-carboxylic acid (Hrib N. J. et al *Journal of Medicinal Chemistry* 1994, 37, 15, 2308-2314).
LC-MS: rt=0.97 min, 467 [M+H]$^+$.

Example 87

(2RS)-6-Methyl-imidazo[2,1-b]thiazole-5-carboxylic acid{1-[2-methyl-5-(3-trifluoromethyl-phenyl)-oxazole-4-carbonyl]-azetidin-2-ylmethyl}-amide This compound has been prepared as in Example 5 but reaction with 2-methyl-5-(3-trifluoromethyl-phenyl)-oxazole-4-carboxylic acid.
LC-MS: rt=0.91 min, 504 [M+H]$^+$.

Example 88

(2RS)-6-Methyl-imidazo[2,1-b]thiazole-5-carboxylic acid{1-[5-(3-methoxy-phenyl)-2-methyl-oxazole-4-carbonyl]-azetidin-2-ylmethyl}-amide This compound has been prepared as in Example 5 but reaction with 2-methyl-5-(3-methoxy-phenyl)-oxazole-4-carboxylic acid.
LC-MS: rt=0.81 min, 466 [M+H]$^+$.

Example 89

(2RS)-2,3,6-Trimethyl-imidazo[2,1-b]thiazole-5-carboxylic acid [1-(3',4'-dimethyl-biphenyl-2-carbonyl)-azetidin-2-ylmethyl]-amide This compound has been prepared as in Example 5 but using 2,3,6-trimethyl-imidazo[2,1-b]thiazole-5-carboxylic acid.
LC-MS: rt=0.88 min, 487 [M+H]$^+$.

Example 90

(2RS)-2,3-Dimethyl-imidazo[2,1-b]thiazole-5-carboxylic acid [1-(3',4'-dimethyl-biphenyl-2-carbonyl)-azetidin-2-ylmethyl]-amide This compound has been prepared as in Example 5 but using 2,3-dimethyl-imidazo[2,1-b]thiazole-5-carboxylic acid.
LC-MS: rt=0.92 min, 473 [M+H]$^+$.

Example 91

(2RS)-3-Methyl-imidazo[2,1-b]thiazole-6-carboxylic acid [1-(3',4'-dimethyl-biphenyl-2-carbonyl)-azetidin-2-ylmethyl]-amide This compound has been prepared as in Example 5 but using 3-methyl-imidazo[2,1-b]thiazole-6-carboxylic acid.
LC-MS: rt=0.96 min, 459 [M+H]$^+$.

Example 92

(2RS)-2,6-Dimethyl-imidazo[2,1-b]thiazole-5-carboxylic acid [1-(2-methyl-5-m-tolyl-thiazole-4-carbonyl)-azetidin-2-ylmethyl]-amide This compound has been prepared as in Example 5 but using 2,6-dimethyl-imidazo[2,1-b]thiazole-5-carboxylic acid.
LC-MS: rt=0.85 min, 480 [M+H]$^+$.

Example 93

(2RS)-2,3-Dihydro-benzofuran-7-carboxylic acid{1-[5-(4-fluoro-phenyl)-2-methyl-thiazole-4-carbonyl]-azetidin-2-ylmethyl}-amide This compound has been prepared as in Example 5 but using commercially available 2,3-dihydro-benzofuran-7-carboxylic acid.
LC-MS: rt=0.91 min, 452 [M+H]$^+$.

Example 94

(2RS)-3,4-Dihydro-2H-benzo[1,4]oxazine-8-carboxylic acid [1-(2-methyl-5-m-tolyl-thiazole-4-carbonyl)-azetidin-2-ylmethyl]-amide This compound has been prepared as in Example 5 but using 3,4-dihydro-2H-benzo[1,4]oxazine-8-carboxylic acid which has been prepared by saponification of the corresponding methyl ester with a base such as NaOH in a solvent MeOH/water (Kuroita T. et al, *Chemical Pharmaceutical Bulletin* 1996, 44, 4, 756-764).
LC-MS: rt=0.88 min, 463 [M+H]$^+$.

Example 95

(2RS)-6-Methyl-imidazo[2,1-b]thiazole-5-carboxylic acid [1-(2-methyl-4-p-tolyl-thiazole-5-carbonyl)-azetidin-2-ylmethyl]-amide This compound has been prepared as in Example 5 but using 2-methyl-4-p-tolyl-thiazole-5-carboxylic acid.
LC-MS: rt=0.80 min, 466 [M+H]$^+$.

Example 96

(2RS)-4-Methyl-3-oxo-3,4-dihydro-2H-benzo[1,4]oxazine-5-carboxylic acid [1-(2-methyl-5-m-tolyl-thiazole-4-carbonyl)-azetidin-2-ylmethyl]-amide This compound has been prepared as in Example 5 but using 4-methyl-3-oxo-3,4-dihydro-2H-benzo[1,4]oxazine-5-carboxylic acid which has been prepared by saponification of the corresponding ethyl ester with a base such as NaOH in a solvent EtOH/water (Kuroita T. et al, *Chemical Pharmaceutical Bulletin* 1996, 44, 4, 756-764).
LC-MS: rt=0.91 min, 491 [M+H]$^+$.

Example 97

(2RS)-3,6-Dimethyl-imidazo[2,1-b]thiazole-5-carboxylic acid [1-(2-methyl-5-m-tolyl-thiazole-4-carbonyl)-azetidin-2-ylmethyl]-amide This compound has been prepared as in Example 5 but using 3,6-dimethyl-imidazo[2,1-b]thiazole-5-carboxylic acid.
LC-MS: rt=0.80 min, 480 [M+H]$^+$.

Example 98

(2RS)-Benzo[1,2,5]thiadiazole-4-carboxylic acid{1-[5-(4-fluoro-phenyl)-2-methyl-thiazole-4-carbonyl]-azetidin-2-ylmethyl}-amide This compound has been prepared as in Example 5 but using commercially available benzo[1,2,5]thiadiazole-4-carboxylic acid.
LC-MS: rt=0.90 min, 468 [M+H]$^+$.

Example 99

(2RS)-2-Methyl-benzo[d]thiophene-3-carboxylic acid [1-(2-methyl-5-m-tolyl-thiazole-4-carbonyl)-azetidin-2-ylmethyl]-amide This compound has been prepared as in Example 5 but using 2-methyl-benzo[d]thiophene-3-carboxylic acid (WO04/081010).
LC-MS: rt=1.03 min, 476 [M+H]$^+$.

Example 100

(2RS)-4-Methyl-3,4-dihydro-2H-benzo[1,4]oxazine-5-carboxylic acid [1-(2-methyl-5-m-tolyl-thiazole-4-carbonyl)-azetidin-2-ylmethyl]-amide This compound has been prepared as in Example 5 but using 4-methyl-3,4-dihydro-2H-benzo[1,4]oxazine-5-carboxylic acid which has been prepared by reduction with sodium borohydride in the presence of boron trifluoride diethyl etherate and saponification of 4-methyl-3-oxo-3,4-dihydro-2H-benzo[1,4]oxazine-5-carboxylic acid ethyl ester which with a base such as NaOH in a solvent EtOH/water (Kuroita T. et al, *Chemical Pharmaceutical Bulletin* 1996, 44, 4, 756-764).
LC-MS: rt=0.93 min, 477 [M+H]$^+$.

Example 101

(2RS)-N-{1-[5-(4-fluoro-phenyl)-2-methyl-thiazole-4-carbonyl]-azetidin-2-ylmethyl}-3-methyl-benzamide This compound has been prepared as in Example 5 but using commercially available 3-methylbenzoic acid.
LC-MS: rt=0.97 min, 424 [M+H]$^+$.

Example 102

(2RS)-6-Methyl-imidazo[2,1-b]thiazole-5-carboxylic acid{1-[5-(4-methoxy-phenyl)-2-methyl-oxazole-4-carbonyl]-azetidin-2-ylmethyl}-amide This compound has been prepared as in Example 5 but using 2-methyl-5-(4-methoxy-phenyl)-oxazole-4-carboxylic acid.
LC-MS: rt=0.81 min, 466 [M+H]$^+$.

Example 103

(2RS)-Benzofuran-4-carboxylic acid [1-(2'-methyl-biphenyl-2-carbonyl)-azetidin-2-ylmethyl]-amide This compound has been prepared as in Example 2 but using 2'-methyl-biphenyl-2-carboxylic acid and benzofuran-4-carboxylic acid.
LC-MS: rt=0.99 min, 425 [M+H]$^+$.

Example 104

(2RS)-6-Methyl-imidazo[2,1-b]thiazole-5-carboxylic acid{1-[4-(3-methoxy-phenyl)-2-methyl-thiazole-5-carbonyl]-azetidin-2-ylmethyl}-amide This compound has been prepared as in Example 5 but using 2-methyl-4-(3-methoxy-phenyl)-thiazole-5-carboxylic acid.
LC-MS: rt=0.77 min, 482 [M+H]$^+$.

Example 105

(2RS)-2,3,5-Trimethyl-imidazo[2,1-b]thiazole-6-carboxylic acid [1-(3',4'-dimethyl-biphenyl-2-carbonyl)-azetidin-2-ylmethyl]-amide This compound has been prepared as in Example 5 but using 2,3,5-trimethyl-imidazo[2,1-b]thiazole-6-carboxylic acid.
LC-MS: rt=1.02 min, 487 [M+H]$^+$.

Example 106

(2RS)-3-Chloro-N-{1-[5-(4-fluoro-phenyl)-2-methyl-thiazole-4-carbonyl]-azetidin-2-ylmethyl}-2-methyl-benzamide This compound has been prepared as in Example 5 but using commercially available 3-chloro-2-methylbenzoic acid.
LC-MS: rt=0.99 min, 458 [M+H]$^+$.

Example 107

(2RS)-6-Methyl-imidazo[2,1-b]thiazole-5-carboxylic acid{1-[4-(4-fluoro-phenyl)-2-methyl-thiazole-5-carbonyl]-azetidin-2-ylmethyl}-amide This compound has been prepared as in Example 5 but using commercially available 6-methyl-imidazo[2,1-b]thiazole-5-carboxylic acid.
LC-MS: rt=0.78 min, 470 [M+H]$^+$.

Example 108

(2RS)-N-{1-[5-(4-Fluoro-phenyl)-2-methyl-thiazole-4-carbonyl]-azetidin-2-ylmethyl}-2-methoxy-benzamide This compound has been prepared as in Example 5 but using commercially available 2-methoxybenzoic acid.
LC-MS: rt=0.93 min, 440 [M+H]$^+$.

Example 109

(2RS)-1-Methyl-1H-indole-3-carboxylic acid{1-[5-(4-fluoro-phenyl)-2-methyl-thiazole-4-carbonyl]-azetidin-2-ylmethyl}-amide This compound has been prepared as in Example 5 but using commercially available 1-methyl-1H-indole-3-carboxylic acid.
LC-MS: rt=0.95 min, 463 [M+H]$^+$.

Example 110

(2RS)-6-Methyl-imidazo[2,1-b]thiazole-5-carboxylic acid{1-[4-(3-fluoro-phenyl)-2-methyl-thiazole-5-carbonyl]-azetidin-2-ylmethyl}-amide This compound has been prepared as in Example 5 but using 2-methyl-4-(3-fluoro-phenyl)-thiazole-5-carboxylic acid.
LC-MS: rt=0.79 min, 470 [M+H]$^+$.

Example 111

(2RS)-2-Bromo-N-{1-[5-(4-fluoro-phenyl)-2-methyl-thiazole-4-carbonyl]-azetidin-2-ylmethyl}-5-methyl-benzamide This compound has been prepared as in Example 5 but using commercially available 2-bromo-5-methylbenzoic acid.
LC-MS: rt=0.98 min, 502 [M+H]$^+$.

Example 112

(2RS)-6-Methyl-imidazo[2,1-b]thiazole-5-carboxylic acid{1-[2-methyl-4-(4-trifluoromethyl-phenyl)-thiazole-5-carbonyl]-azetidin-2-ylmethyl}-amide This compound has been prepared as in Example 5 but using 2-methyl-4-(4-trifluoromethyl-phenyl)-thiazole-5-carboxylic acid.
LC-MS: rt=0.87 min, 520 [M+H]$^+$.

II. Biological Assays
In vitro Assay
The orexin receptor antagonistic activity of the compounds of formula (I) is determined in accordance with the following experimental method.
Experimental Method:
Intracellular Calcium Measurements:
Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% inactivated fetal calf serum (FCS). The cells are seeded at 80'000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% $CO_2$.

Human orexin-A as an agonist is prepared as 1 mM stock solution in methanol:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 µl HBSS containing 2.5 mM probenecid, 0.1% BSA, 2 mM HEPES. 100 µl of that same buffer is left in each well. Within the Fluorescent Imaging Plate Reader (FLIPR, Molecular Devices), antagonists are added to the plate in a volume of 50 µl, incubated for 20 min and finally 100 µl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined.

Antagonistic activities ($IC_{50}$ values) of compounds of formula (I) are below 10000 nM with respect to the $OX_1$ and/or the $OX_2$ receptor (preferred compounds: <1000 nM, more preferred compounds: <100 nM, most preferred compounds: <10 nM). $IC_{50}$ values of 89 from 112 exemplified compounds are in the range of 4.7-8788 nM with an average of 1743 nM with respect to the $OX_1$ receptor. $IC_{50}$ values of 112 from 112 exemplified compounds are in the range of 1.9-988 nM with an average of 217 nM with respect to the $OX_2$ receptor. Antagonistic activities of selected compounds are displayed in Table 1.

TABLE 1

| Compound of Example | $OX_1$ $IC_{50}$ (nM) | $OX_2$ $IC_{50}$ (nM) |
| --- | --- | --- |
| 9 | 88 | 122 |
| 11 | 196 | 66 |
| 15 | 70 | 11 |
| 21 | 41 | 7 |
| 22 | 10 | 5 |
| 28 | 89 | 11 |
| 32 | 75 | 25 |
| 40 | 11 | 39 |
| 42 | 85 | 41 |
| 50 | 391 | 57 |
| 54 | 3098 | 13 |
| 57 | 1199 | 19 |
| 61 | 1916 | 43 |
| 67 | 2013 | 102 |
| 83 | 1643 | 406 |

The invention claimed is:
1. A compound of formula (I)

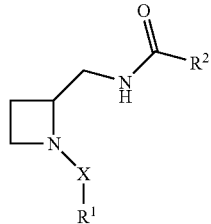

Formula (I)

wherein
X represents C(O) or $SO_2$;
$R^1$ represents mono-substituted phenyl, wherein the substituent is selected from the group consisting of ($C_{1-4}$) alkoxy, trifluoromethoxy and unsubstituted, or mono-, di-, or tri-substituted phenyl wherein the substituents are independently selected from the group consisting of ($C_{1-4}$)alkyl, ($C_{1-4}$)alkoxy, halogen, cyano, trifluoromethyl and trifluoromethoxy;
or $R^1$ represents five-membered heteroaryl, wherein said five-membered heteroaryl is disubstituted, wherein the substituents are independently selected from the group consisting of ($C_{1-4}$)alkyl, $NR^3R^4$ and unsubstituted, or mono-, di-, or tri-substituted phenyl wherein the substituents are independently selected from the group consisting of ($C_{1-4}$)alkyl, ($C_{1-4}$alkoxy, halogen, cyano, trifluoromethyl and trifluoromethoxy;
$R^2$ represents aryl, wherein the aryl is unsubstituted, or mono-, di-, or tri-substituted wherein the substituents are independently selected from the group consisting of ($C_{1-4}$)alkyl, ($C_{1-4}$)alkoxy, halogen and $NR^3R^4$, or heteroaryl, wherein said heteroaryl is a group selected from the group consisting of indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, cinnolinyl, and imidazo[2,1-b]thiazolyl; wherein the heteroaryl is unsubstituted, or mono-, or disubstituted wherein the substituents are independently ($C_{1-4}$)alkyl or halogen; or
$R^2$ represents heterocyclyl, wherein said heterocyclyl is a group selected from the group consisting of 3,4-dihydro-2H-benzo[1,4]oxazinyl, 2,3-dihydro-benzofuranyl, benzo[1,3]dioxolyl, 2,3-dihydro-benzo[1,4]dioxinyl, 4H-benzo[1,3]dioxinyl, chromanyl, and chromenyl; wherein said heterocyclyl is unsubstituted, or mono-substituted with ($C_{1-4}$)alkyl or oxo;
$R^3$ represents hydrogen or ($C_{1-4}$)alkyl; and
$R^4$ represents hydrogen or ($C_{1-4}$)alkyl;
in free or salt form.

2. The compound according to claim 1, wherein the azetidine moiety has the (S)-configuration:

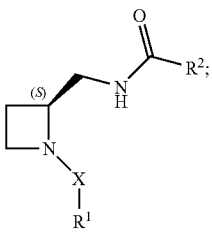

in free or salt form.

3. The compound according to claim 1, wherein X represents C(O); in free or salt form.

4. The compound according to claim 3, wherein
$R^1$ represents mono-substituted phenyl, wherein the substituent is selected from the group consisting of $(C_{1-4})$ alkoxy, trifluoromethoxy, and unsubstituted, or mono-, di- or tri-substituted phenyl wherein the substituents are independently selected from the group consisting of $(C_{1-4})$alkyl, $(C_{1-4})$ alkoxy, halogen, cyano, trifluoromethyl and trifluoromethoxy; or
$R^1$ represents di-substituted five-membered heteroaryl, wherein the substituents are independently selected from the group consisting of $(C_{1-4})$alkyl, —NH$_2$, and unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy; in free or salt form.

5. The compound according to claim 3, wherein
$R^2$ represents heteroaryl, wherein said heteroaryl is a group selected from the group consisting of indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, cinnolinyl, and imidazo[2,1-b]thiazolyl; wherein the heteroaryl is unsubstituted, or mono-, or di-substituted wherein the substituents are independently selected from the group consisting of $(C_{1-4})$alkyl, and halogen; or
$R^2$ represents heterocyclyl, wherein said heterocyclyl is a group selected from the group consisting of 3,4-dihydro-2H-benzo[1,4]oxazinyl, 2.3-dihydro-benzofuranyl, benzo[1,3]dioxolyl, 2,3-dihydro-benzo[1,4]dioxinyl, 4H-benzo[1,3]dioxinyl, chromanyl, and chromenyl; wherein said heterocyclyl is unsubstituted, or mono-substituted with $(C_{,1-4})$alkyl or oxo; in free or salt form.

6. The compound according to claim 3, wherein, in case $R^1$ represents heteroaryl, said heteroaryl is thiazol-4-yl, which is di-substituted in positions 2 and 5, wherein the substituent in position 2 is selected from $(C_{1-4})$alkyl and —NH$_2$ and the substituent in position 5 is unsubstituted, or mono-, or di-substituted phenyl, wherein the substituents are independently selected from the group consisting of $(C_{1-4})$alkyl, $(C_{1-4})$alkoxy, halogen, cyano, trifluoromethyl and trifluoromethoxy; in free or salt form.

7. The compound according to claim 3, wherein, in case $R^1$ represents heteroaryl, said heteroaryl is a group selected from benzofuran-4-yl, 2-methyl-benzofuran-4-yl, 2-methyl-benzofuran-3-yl, benzoxazol-4-yl, imidazo[2,1-b]-thiazole-5-yl, 6-methyl-imidazo[2,1-b]-thiazole-5-yl, 6-chloro-imidazo[2,1-b]-thiazole-5-yl, 3-methyl-imidazo[2,1-b]-thiazole-2-yl;
in free or salt form.

8. The compound according to claim 3, wherein, in case $R^2$ represents heterocyclyl, said heterocyclyl is a group selected from 3,4-dihydro-2H-benzo[1,4]oxazine-5-yl, 3,4-dihydro-2H-benzo[1,4]oxazine-8-yl, 4-methyl-3,4-dihydro-2H-benzo[1,4]oxazine-5-yl, 4-methyl-3,4-dihydro-2H-benzo[1,4]oxazine-8-yl, 3-oxo-3,4-dihydro-2H-benzo[1,4]oxazine-5-yl, 4-methyl-3-oxo-3,4-dihydro-2H-benzo[1,4]oxazine-5-yl, 4-methyl-3-oxo-3,4-dihydro-2H-benzo[1,4]oxazine-8-yl, 2,3-dihydro-benzofuran-7-yl, chroman-8-yl, chroman-5-yl, and 2H-chromene-5-yl;
in free or salt form.

9. A compound according to claim 1 selected from the group consisting of:
Benzofuran-4-carboxylic acid [1-(biphenyl-2-carbonyl)-azetidin-2-ylmethyl]-amide;
(2S)-Benzofuran-4-carboxylic acid [1-(biphenyl-2-carbonyl)-azetidin-2-ylmethyl]-amide;
Benzofuran-4-carboxylic acid [1-(biphenyl-2-sulfonyl)-azetidin-2-ylmethyl]-amide;
(2S)-Benzofuran-4-carboxylic acid [1-(biphenyl-2-sulfonyl)-azetidin-2-ylmethyl]-amide;
(2S)-Benzofuran-4-carboxylic acid [1-(2-trifluoromethoxy-benzenesulfonyl)-azetidin-2-ylmethyl]-amide;
(2S)-Benzofuran-4-carboxylic acid [1 -(2-methoxy-benzenesulfonyl)-azetidin-2-ylmethyl]-amide;
Benzofuran-4-carboxylic acid{1-(4-fluoro-phenyl)-2-methyl-thiazole-4-carbonyl]-azetidin-2-ylmethyl}-amide;
6-Methyl-imidazo[2,1-b]thiazole-5-carboxylic acid [1-(2-methyl-5-p-tolyl-thiazole-4-carbonyl)-azetidin-2-ylmethyl]-amide;
6-Methyl-imidazo[2,1-b]thiazole-5-carboxylic acid{1-[5-(4-fluoro-phenyl)-2-methyl-thiazole-4-carbonyl]-azetidin-2-ylmethyl}-amide;
6-Methyl-imidazo[2,1-b]thiazole-5-carboxylic acid [1-(2-methyl-5-m-tolyl-thiazole-4-carbonyl)-azetidin-2-ylmethyl]-amide;
6-Methyl-imidazo[2,1-b]thiazole-5-carboxylic acid{1-[5 -(3-fluoro-phenyl)-2-methyl-thiazole-4-carbonyl]-azetidin-2-ylmethyl}-amide;
6-Methyl-imidazo[2,1-b]thiazole-5-carboxylic acid{1 -[5-(4-trifluoromethyl-phenyl)-2-methyl-thiazole-4-carbonyl]-azetidin-2-ylmethyl}-amide;
6-Methyl-imidazo[2,1-b]thiazole-5-carboxylic acid{1 -[5-(4-ethyl-phenyl)-2-methyl-thiazole-4-carbonyl]-azetidin-2-ylmethyl}-amide;
(2S)-Benzofuran-4-carboxylic acid [1 -(3 -trifluoromethyl-benzoyl)-azetidin-2-ylmethyl]-amide;
(2S)-Benzofuran-4-carboxylic acid [1-(3',4'-dimethyl-biphenyl-2-carbonyl)-azetidin-2-ylmethyl]-amide;
(2S)-Benzofuran-4-carboxylic acid{1-[5-(4-fluoro-phenyl)-2-methyl-thiazole-4-carbonyl]-azetidin-2-ylmethyl}-amide;
(2S)-6-Methyl-imidazo[2,1-b]thiazole-5-carboxylic acid{1-[5-(3,4-dimethyl-phenyl)-2-methyl-thiazole-4-carbonyl]azetidin-2-ylmethyl}-amide;
(2S)-6-Methyl-imidazo[2,1-b]thiazole-5-carboxylic acid [1 -(2-methyl-5-m-tolyl-thiazole-4-carbonyl)-azetidin-2-ylmethyl]-amide;
(2S)-6-Methyl-imidazo[2,1-b]thiazole-5-carboxylic acid [1 -(3',4'-dimethyl-biphenyl-2-carbonyl)-azetidin-2-ylmethyl]-amide;
(2S)-6-Methyl-imidazo[2,1-b]thiazole-5-carboxylic acid [1-(2-amino-5-m-tolyl-thiazole-4-carbonyl)-azetidin-2-ylmethyl]-amide;
(2S)-6-Chloro-imidazo[2,1-b]thiazole-5-carboxylic acid [1-(2-methyl-5-m-tolyl-thiazole-4-carbonyl)-azetidin-2-ylmethyl]-amide;
(2S)-6-Chloro-imidazo[2,1-b]thiazole-5-carboxylic acid [1 -(2-amino-5-m-tolyl-thiazole-4-carbonyl)-azetidin-2-ylmethyl]-amide;
Benzofuran-4-carboxylic acid [1-(3',4'-dimethyl-biphenyl-2-carbonyl)-azetidin-2-ylmethyl]-amide;
6-Methyl-imidazo[2,1-b]thiazole-5-carboxylic acid{1-[5-(3,4-dimethyl-phenyl)-2-methyl-thiazole-4-carbonyl]-azetidin-2-ylmethyl}-amide;
6-Methyl-imidazo[2,1-b]thiazole-5-carboxylic acid{1-[5-(3-methoxy-phenyl)-2-methyl-thiazole-4-carbonyl]-azetidin-2-ylmethyl}-amide;
6-Methyl-imidazo[2,1-b]thiazole-5-carboxylic acid{1-[5-(3-chloro-phenyl)-2-methyl-thiazole-4-carbonyl]-azetidin-2-ylmethyl}-amide;

6-Methyl-imidazo[2,1-b]thiazole-5-carboxylic acid {1-[2-methyl-5-(3-trifluoromethyl-phenyl)-thiazole-4-carbonyl]-azetidin-2-ylmethyl}-amide;
6-Methyl-imidazo[2,1-b]thiazole-5-carboxylic acid {1-[5-(4-methoxy-phenyl)-2-methyl-thiazole-4-carbonyl]-azetidin-2-ylmethyl}-amide;
6-Methyl-imidazo[2,1-b]thiazole-5-carboxylic acid {1-[5-(3,5-difluoro-phenyl)-2-methyl-thiazole-4-carbonyl] azetidin-2-ylmethyl}-amide;
6-Methyl-imidazo[2,1-b]thiazole-5-carboxylic acid {1-[5-(3-bromo-4-fluoro-phenyl)-2-methyl-thiazole-4-carbonyl]-azetidin-2-ylmethyl}-amide;
6-Methyl-imidazo[2,1-b]thiazole-5-carboxylic acid {1-[5-(4-chloro-phenyl)-2-methyl-thiazole-4-carbonyl]-azetidin-2-ylmethyl}-amide;
6-Methyl-imidazo[2,1-b]thiazole-5-carboxylic acid {1-[5-(3,4-dichloro-phenyl)-2-methyl-thiazole-4-carbonyl] azetidin-2-ylmethyl}-amide;
6-Chloro-imidazo[2,1-b]thiazole-5-carboxylic acid {1-[5-(3,4-dimethyl-phenyl)-2-methyl-thiazole-4-carbonyl] azetidin-2-ylmethyl}-amide;
6-Chloro-imidazo[2,1-b]thiazole-5 -carboxylic acid [1-(2-methyl-5-m-tolyl-thiazole-4-carbonyl)-azetidin-2-ylmethyl]-amide;
2-Methyl-benzofuran-4-carboxylic acid [1-(2-methyl-5-m-tol yl-thiazole-4-carbonyl)-azetidin-2-ylmethyl]-amide;
2H-Chromene-5 -carboxylic acid [1-(2-methyl-5-m-tolyl-thiazole-4-carbonyl)-azetidin-2-ylmethyl]-amide;
Benzooxazole-4-carboxylic acid [1-(2-methyl-5-m-tolyl-thiazole-4-carbonyl)-azetidin-2-ylmethyl]-amide;
Benzofuran-3-carboxylic acid [1-(2-methyl-5-m-tolyl-thiazole-4-carbonyl)-azetidin-2-ylmethyl]-amide;
2-Methyl-benzofuran-3-carboxylic acid [1-(2-methyl-5-m-tolyl-thiazole-4-carbonyl)-azetidin-2-ylmethyl]-amide;
3,5-Dimethyl-imidazo[2,1-b]thiazole-6-carboxylic acid [1-(2-methyl-5-m-tolyl-thiazole-4-carbonyl)-azetidin-2-ylmethyl]-amide;
3,4-Dihydro-2H-benzo [1,4]oxazine-5-carboxylic acid [1-(2-methyl-5-m-tolyl-thiazole-4-carbonyl)-azetidin-2-ylmethyl]-amide;
5-Methyl-imidazo[2,1-b]thiazole-6-carboxylic acid [1-(2-methyl-5-m-tolyl-thiazole-4-carbonyl)-azetidin-2-ylmethyl]-amide;
4-Methyl-3-oxo-3,4-dihydro-2H-benzo [1,4]oxazine-8-carboxylic acid [1-(2-methyl-5-m-tolyl-thiazole-4-carbonyl)-azetidin-2-ylmethyl]-amide;
Imidazo[2,1-b]thiazole-5-carboxylic acid [1-(2-methyl-5-m-tolyl-thiazole-4-carbonyl)-azetidin-2-ylmethyl]-amide;
Imidazo [2,1-b]thiazole-5-carboxylic acid [1-(3',4'-dimethyl-biphenyl-2-carbonyl)-azetidin-2-ylmethyl]-amide;
3-Methyl-imidazo[2,1-b]thiazole-5-carboxylic acid [1-(3',4'-dimethyl-biphenyl-2-carbonyl)-azetidin-2-ylmethyl]-amide;
3,5-Dimethyl-imidazo[2,1-b]thiazole-6-carboxylic acid [1-(3', 4'dimethyl-biphenyl-2-carbonyl)-azetidin-2-ylmethyl]-amide;
6-Chloro-imidazo[2,1-b]thiazole-5 -carboxylic acid [1-(3',4'-dimethyl-biphenyl-2-carbonyl)-azetidin-2-ylmethyl]-amide;
6-Methyl-imidazo[2,1-b]thiazole-5 -carboxylic acid [1-(biphenyl-2-sulfonyl)-azetidin-2-ylmethyl]-amide;

6-Trifluoromethyl-imidazo[2,1-b]thiazole-5-carboxylic acid [1-(2-methyl-5-m-tolyl-thiazole-4-carbonyl)-azetidin-2-ylmethyl]-amide;
6-Methyl-imidazo[2,1-b]thiazole-5-carboxylic acid [1-(2-methyl-5-phenyl-thiazole-4-carbonyl)-azetidin-2-ylmethyl]-amide;
3,4-Dihydro-2H-benzo [1,4]oxazine-5-carboxylic acid [1-(2-amino-5-m-tolyl-thiazole-4-carbonyl)-azetidin-2-ylmethyl]-amide;
3-Methyl-imidazo[2,1-b]thiazole-2-carboxylic acid [1-(3',4'-dimethyl-biphenyl-2-carbonyl)-azetidin-2-ylmethyl]-amide;
4-Methyl-3,4-dihydro-2H-benzo [1,4]oxazine-8-carboxylic acid [1-(2-methyl-5-m-tolyl-thiazole-4-carbonyl)-azetidin-2-ylmethyl]-amide;
3-Methyl-imidazo[2,1-b]thiazole-2-carboxylic acid [1-(2-methyl-5-m-tolyl-thiazole-4-carbonyl)-azetidin-2-ylmethyl]-amide;
Chroman-5-carboxylic acid [1-(2-methyl-5-m-tolyl-thiazole-4-carbonyl)-azetidin-2-ylmethyl]-amide;
Chroman-8-carboxylic acid [1-(2-methyl-5 -m-tolyl -thiazole-4-carbonyl)-azetidin-2-ylmethyl]-amide ;
3-Oxo-3,4-dihydro-2H-benzo[1,4]oxazine-5-carboxylic acid [1-(2-methyl-5-m-tolyl-thiazole-4-carbonyl)-azetidin-2-ylmethyl]-amide;
2-Methyl-imidazo[2,1-b]thiazole-5 -carboxylic acid [1-(3',4'-dimethyl-biphenyl-2-carbonyl)-azetidin-2-ylmethyl]-amide;
6-Methyl-imidazo[2,1-b]thiazole-5 -carboxylic acid {-1-[5-(2,4-dimethyl-phenyl)-2-methyl-thiazole-4-carbonyl]-azetidin-2-ylmethyl}-amide;
3-Methyl-imidazo[2,1-b]thiazole-5 -carboxylic acid [1-(2-methyl-5-m-tolyl-thiazole-4-carbonyl)-azetidin-2-ylmethyl]-amide;
2-Methyl-benzooxazole-4-carboxylic acid [1-(2-methyl-5-m-tolyl-thiazole-4-carbonyl)-azetidin-2-ylmethyl]-amide;
3,6-Dimethyl-imidazo[2,1-b]thiazole-5-carboxylic acid [1-(3',4'-dimethyl-biphenyl-2-carbonyl)-azetidin-2-ylmethyl]-amide;
6-Methyl-imidazo[2,1-b]thiazole-5-carboxylic acid {1-[5-(2-fluoro-phenyl)-2-methyl-thiazole-4-carbonyl]-azetidin-2-ylmethyl}-amide; and
(2S)-Benzofuran-4-carboxylic acid [1-(naphthalene-1-sulfonyl)-azetidin-2-ylmethyl]-amide; in free or salt form.

10. A pharmaceutical composition comprising a compound according to claim 1 in free or pharmaceutically acceptable salt form, and a pharmaceutically acceptable carrier material.

11. A method for the prevention or treatment of an insomnia comprising administering to a patient in need thereof a therapeutically effective amount of a compound according to claim 1 in free or pharmaceutically acceptable salt form.

12. The compound according to claim 3, wherein, in case $R^1$ represents five-membered heteroaryl, wherein said five-membered heteroaryl is an oxazolyl or thiazolyl group, which groups independently are mono- or disubstituted, wherein the substituents are independently selected from the group consisting of $(C_{1-4})$alkyl, $NR^3R^4$, and unsubstituted, or mono-, di-, or tri-substituted phenyl, wherein the substituents are independently selected from the group consisting of $(C_{1-4})$alkyl, $(C_{1-4})$alkoxy, halogen, cyano, trifluoromethyl and trifluoromethoxy;
in free or salt form.

13. The compound according to claim 3, wherein, in case $R^1$ represents five-membered heteroaryl, wherein said five-membered heteroaryl is a group selected from the group consisting of:

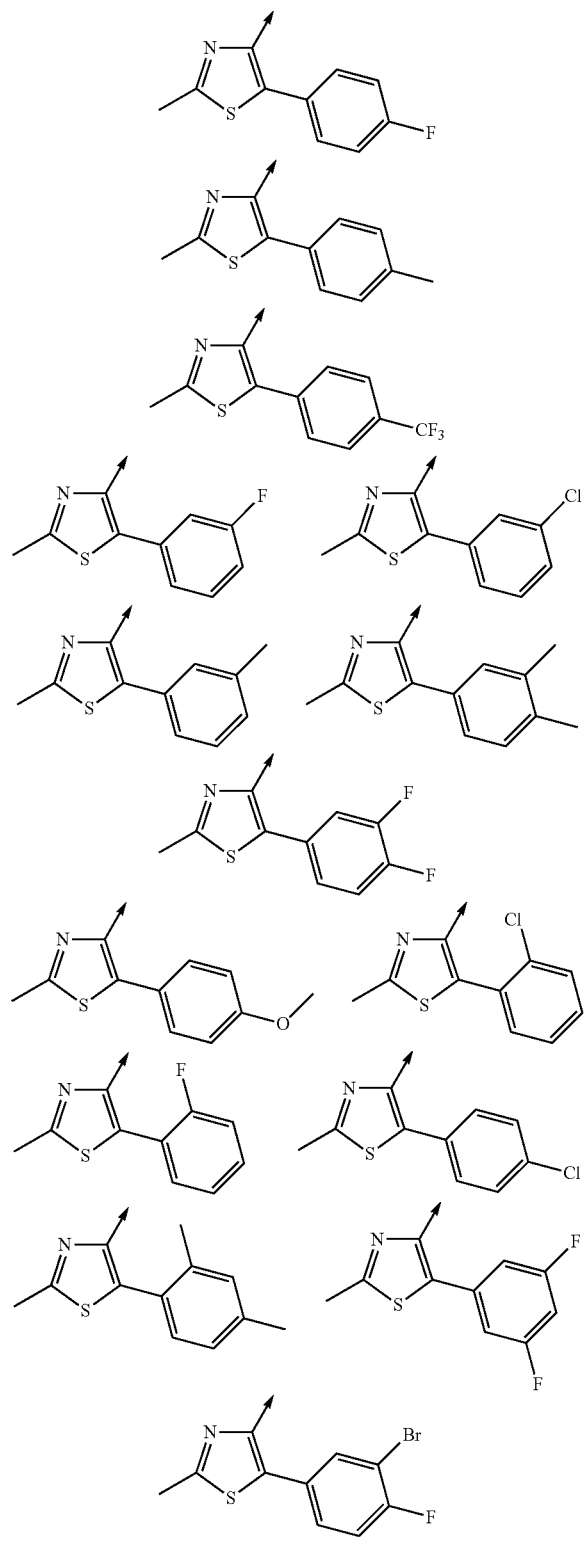

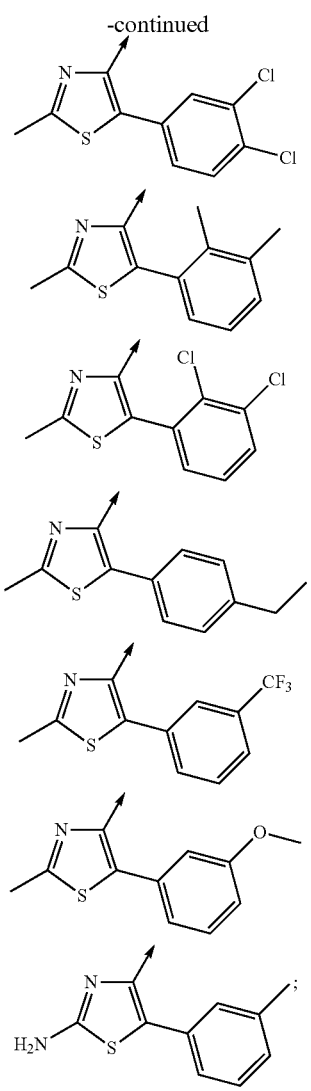

in free or salt form.

14. The compound according to claim 3, wherein, in case $R^1$ represents mono-substituted phenyl, said phenyl is substituted with unsubstituted, or mono-, di-, or tri-substituted phenyl wherein the substituents are independently selected from the group consisting of $(C_{1-4})$alkyl, $(C_{1-4})$alkoxy, halogen, cyano, trifluoromethyl and trifluoromethoxy;

in free or salt form.

15. The compound according to claim 3, wherein, in case $R^1$ represents mono-substituted phenyl, said mono-substituted phenyl is a group selected from biphen-2-yl, 2-trifluoromethoxyphenyl, 2-methoxyphenyl, 3-trifluoromethyl-phenyl, naphthalene-1-yl, 2'-fluoro-biphen-2-yl, 3'-fluoro-biphen-2-yl, 4'-fluoro-biphen-2-yl, 2'-methyl-biphen-2-yl, 3'-methyl-biphen-2-yl, 4'-methyl-biphen-2-yl, 3',4'-dimethyl-biphen-2-yl, and 3'-trifluoromethyl-biphen-2-yl;

in free or salt form.

\* \* \* \* \*